United States Patent [19]

Berger

[11] Patent Number: 4,480,009
[45] Date of Patent: Oct. 30, 1984

[54] SILOXANE-CONTAINING POLYMERS

[75] Inventor: Abe Berger, Summit, N.J.

[73] Assignee: M&T Chemicals Inc., Woodbridge, N.J.

[21] Appl. No.: 466,986

[22] Filed: Feb. 16, 1983

Related U.S. Application Data

[60] Division of Ser. No. 216,599, Dec. 14, 1980, Pat. No. 4,395,527, which is a continuation-in-part of Ser. No. 158,056, Jun. 9, 1980, abandoned, Ser. No. 174,400, Aug. 1, 1980, abandoned, Ser. No. 126,666, Mar. 3, 1980, abandoned, Ser. No. 205,120, Nov. 10, 1980, abandoned, and Ser. No. 051,699, Jun. 25, 1979, abandoned, said Ser. No. 158,050, is a continuation-in-part of Ser. No. 958,358, Nov. 6, 1978, abandoned, said Ser. No. 174,400, is a continuation-in-part of Ser. No. 907,155, May 17, 1978, abandoned, said Ser. No. 126,666, is a continuation-in-part of Ser. No. 011,901, Feb. 13, 1979, abandoned, which is a continuation-in-part of Ser. No. 906,877, May 17, 1980, Pat. No. 4,139,547, said Ser. No. 205,120, is a continuation of Ser. No. 016,412, Mar. 1, 1979, abandoned, which is a continuation-in-part of Ser. No. 907,155, May 17, 1978, abandoned, said Ser. No. 051,699, is a continuation-in-part of Ser. No. 907,155, May 17, 1978, abandoned.

[51] Int. Cl.$^3$ .............................................. B32B 9/04
[52] U.S. Cl. .................................... 428/447; 427/82; 427/86; 427/93; 427/387; 357/7; 357/8; 357/65; 428/450; 528/23; 528/26
[58] Field of Search ................... 357/7, 8, 65; 427/82, 427/86, 93, 387; 528/23, 26; 428/447, 450

[56] References Cited

U.S. PATENT DOCUMENTS

| | | | |
|---|---|---|---|
| 3,282,897 | 11/1966 | Angelo | 528/23 |
| 3,435,002 | 3/1969 | Holub | 528/23 |
| 3,526,544 | 9/1970 | Scala et al. | 428/450 |
| 3,673,145 | 6/1972 | Minami et al. | 528/26 |
| 3,740,305 | 6/1973 | Hoback et al. | 428/450 |
| 3,926,911 | 12/1975 | Greber et al. | 528/26 |
| 4,011,279 | 3/1977 | Berger et al. | 528/23 |
| 4,051,163 | 9/1977 | Berger | 528/26 |
| 4,139,547 | 2/1979 | Berger | 528/26 |
| 4,200,724 | 4/1980 | Darms et al. | 528/26 |
| 4,331,970 | 5/1982 | Yerman | 427/82 |
| 4,338,426 | 7/1982 | Sato et al. | 528/23 |

FOREIGN PATENT DOCUMENTS 1062418  3/1967  United Kingdom .

*Primary Examiner*—Melvyn I. Marquis
*Attorney, Agent, or Firm*—S. A. Marcus; S. H. Parker; J. Matalon

[57] ABSTRACT

The properties of polymeric compositions can be improved by the presence of a polysiloxane unit of formula $$-Q-Z-D-\underset{R^1}{\overset{R^1}{\underset{|}{\overset{|}{Si}}}}-\left[O-\underset{R^2}{\overset{R^2}{\underset{|}{\overset{|}{Si}}}}\right]_x\left[O-\underset{R^4}{\overset{R^3}{\underset{|}{\overset{|}{Si}}}}\right]_y$$

$$\left[O-\underset{R^6}{\overset{R^5}{\underset{|}{\overset{|}{Si}}}}\right]_z-O-\underset{R^1}{\overset{R^1}{\underset{|}{\overset{|}{Si}}}}-D-Z-Q-$$

where
Q is a substituted or unsubstituted aromatic group,
Z is $$-O-, -S-, -\underset{O}{\overset{O}{\underset{\|}{\overset{\|}{S}}}}-, -\underset{O}{\overset{O}{\underset{\|}{\overset{\|}{S}}}}-, -\overset{O}{\underset{\|}{S}}NH-, -HN\overset{O}{\underset{\|}{S}}-, -\overset{O}{\underset{\|}{C}}NH-,$$

$$-HN\overset{O}{\underset{\|}{C}}-, -\overset{O}{\underset{\|}{C}}-O- \text{ or } -O-\overset{O}{\underset{\|}{C}}-;$$

D is unsubstituted or substituted hydrocarbylene $R^1$, $R^2$, $R^3$, $R^4$, $R^5$ and $R^6$ each, independently, is unsubstituted or substituted hydrocarbyl. x, y and z each independently has a value from 0 to 100.

Polyimides containing these units display improved solubility and adhesion; they are useful, among other things, as protective coatings.

32 Claims, No Drawings

SILOXANE-CONTAINING POLYMERS

CROSS REFERENCE TO RELATED APPLICATIONS

This is a divisional of application Ser. No. 216,599, filed Dec. 14, 1980, now, U.S. Pat. No. 4,395,527, which is a continuation-in-part of the following applications:

Application Ser. No. 158,056, filed June 9, 1980, now abandoned, which, in turn, is a continuation-in-part of Application Ser. No. 958,358, filed Nov. 6, 1978, now abandoned;

Application Ser. No. 174,400, filed Aug. 1, 1980, now abandoned, which, in turn, is a continuation-in-part of Application Ser. No. 907,155, filed May 17, 1978, now abandoned;

Application Ser. No. 126,666, filed Mar. 3, 1980, now abandoned, which, in turn, is a continuation-in-part of Application Ser. No. 011,901, filed Feb. 13, 1979, now abandoned and which, in turn, is a continuation-in-part of Application Ser. No. 906,877, filed May 17, 1980, now U.S. Pat. No. 4,139,547;

Application Ser. No. 205,120, filed Nov. 10, 1980, now abandoned, which is a continuation of Application Ser. No. 016,412, filed Mar. 1, 1979, now abandoned, and which, in turn, is a continuation-in-part of Application Ser. No. 907,155, filed May 17, 1978, now abandoned;

Application Ser. No. 051,699, filed June 25, 1979, now abandoned, which, in turn, is a continuation-in-part of Application Ser. No. 907,155, filed May 17, 1978, now abandoned.

FIELD OF THE INVENTION

This invention relates to polymeric compositions containing a polysiloxane unit of formula

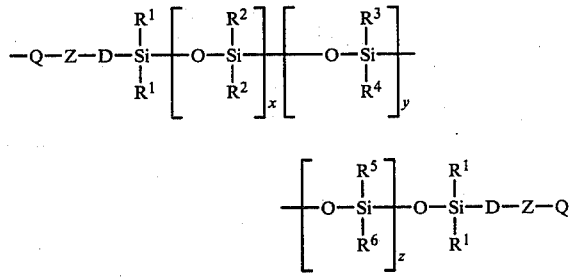

where the substituents are all as defined below.

The invention also relates to precursors of said polysiloxane unit and to methods of making those precursor compounds.

BACKGROUND OF THE INVENTION

Attempts have been made to modify the properties of various polymers by the incorporation of a polysiloxane. These polysiloxanes have typically been alpha-omega-bis (alkylene) polysiloxanes and the results obtained therewith have not been entirely acceptable. These polysiloxanes are sensitive to elevated temperatures, which makes the synthesis of high molecular weight materials difficult and high temperature fabrication techniques unavailable. Further, alpha-omega-bis (alkylene) polysiloxanes are not readily compatible with many polymers.

DESCRIPTION OF THE INVENTION

It has been found that the properties of polymers can be improved by the presence of a unit of formula

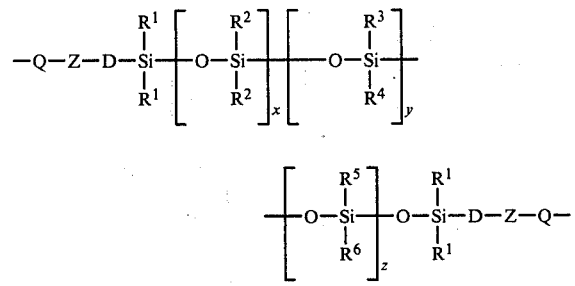

where
Q is a substituted or unsubstituted aromatic group.
Z is

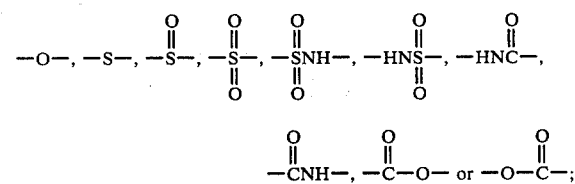

D is unsubstituted or substituted hydrocarbylene $R^1$, $R^2$, $R^3$, $R^4$, $R^5$ and $R^6$ each independently unsubstituted or substituted hydrocarbyl. x, y and z each independently has a value from 0 to 100.

and that polymers containing these units are suited for a variety of applications.

In one aspect, the invention relates to polymeric compositions containing said polysiloxane. These compositions include polyamide, polyimide, poly (amide-imide), polyphenylene sulfide, polyepoxide, polyphenolic, polycarbonate, polyester, polyurethane and polysulfone. In an embodiment of this aspect, the invention relates to the reaction product of a bis (amino) polysiloxane with an acid or anhydride to form part of a polyamide, polyimide or poly (amide-imide), to the reaction product of a bis (amino) polysiloxane with an isocyanate to form part of a polyurethane and to the reaction of a bis (amino) polysiloxane or an anhydride with an oxirane group to form part of a polyepoxide. Additionally, the invention relates to the reaction product of a bis (hydroxy) polysiloxane with phosgene to form part of a polycarbonate, with a polycarboxylic acid to form part of a polyester, with dichlorodiphenyl sulfone to form part of a polysulfone and with formaldehyde to form part of a polyphenolic polymer. This aspect is also embodied in the reaction of a bis (chloro) polysiloxane with sodium sulfide to form part of a polyphenylene sulfide and in a bis (chlorosulfonyl) poly siloxane reacted via the Friedel-Crafts reaction to form part of a polyarylsulfone or part of a polyether sulfone.

In another aspect, the invention relates to solutions of polymers containing said polysiloxane and to coatings applied, films cast and to fibers spun from solutions of these polymers. The invention also relates to molding, extruding, laminating and calendering compositions containing said polysiloxane, as well as to formed, shaped, laminated and coated articles.

In still another aspect the invention relates to bis(functionally-substituted) polysiloxanes and to methods for making these compounds.

The unit of formula

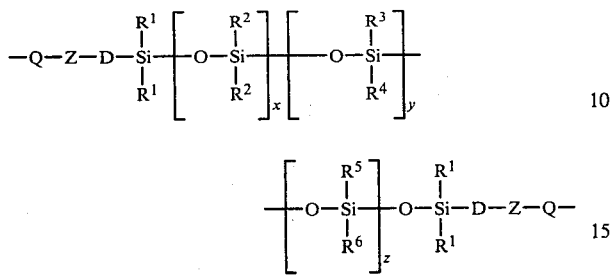

is derived from a bis(functional) polysiloxane of formula

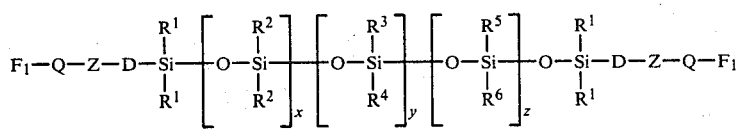

where
$F_1$ is a functional group attached directly to Q or bonded via an intermediate aliphatic group
Q is a substituted or unsubstituted aromatic group
Z is

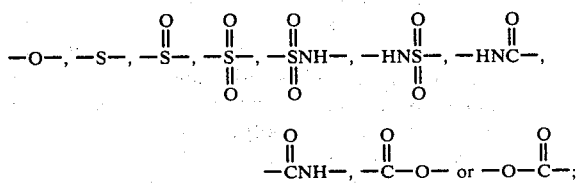

D is unsubstituted or substituted hydrocarbylene $R^1$, $R^2$, $R^3$, $R^4$, $R^5$ and $R^6$ each independently unsubstituted or substituted hydrocarbyl; x, y and z each independently has a value from 0 to 100.

$F_1$ can be hydrogen, chlorine, bromine, iodine, fluorine,

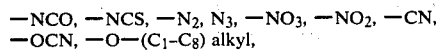

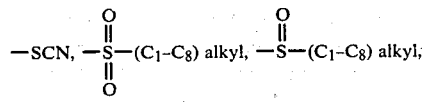

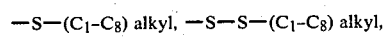

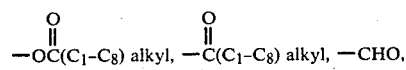

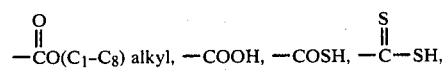

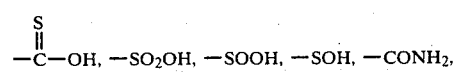

-continued
—OH, —SH, —$NR_aR_b$ where $R_a$ and $R_b$ each independently is hydrogen or lower alkyl or together with N form part of a heterocyclic group; or $F_1$ is alpha-oxirane or

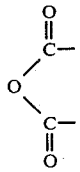

where the carbonyl groups are located ortho to each other. F can be directly bonded to Q or bonded via an intermediate alkyl or alkoxy group of from 1 to 8 carbon atoms, an aryl group, or via an intermediate Q—Z— group.

Q is an aromatic nucleus and can be carbocyclic or heterocyclic; it can contain one or more rings and can be unsubstituted or substituted by one or more groups that do not interfere with the use to which the unit will be put. Thus, Q can be carbocyclic aromatic of 6 to 18 ring carbon atoms such as phenylene, naphthylene, anthracenylene and phenanthrylene. Q can be unsubstituted or substituted by from 1 to 4 of: alkyl of 1 to 12 carbon atoms, alkenyl of 2 to 12 carbon atoms, alkynyl of 2 to 12 carbon atoms, cycloalkyl of 4 to 8 carbon atoms, alkoxy of 1 to 12 carbon atoms, alkylthio of 1 to 12 carbon atoms, phenyl, alkylphenylene having 1 to 12 carbon atoms in the alkyl group, phenoxy, phenylthio, alkylcarbonyloxy of 2 to 12 carbon atoms, phenylalkylene of 1 to 12 carbon atoms in the alkylene group, alkylcarbonyl of 2 to 12 carbon atoms, alkoxycarbonyl of 2 to 12 carbon atoms, bromo, chloro, fluoro, iodo, nitro, cyano, cyanothio, carboxy, carbonyl, hydroxy, mercapto, formyl, thioformyl and mercaptocarbonyl.

Q can also be substituted or unsubstituted heterocyclic aromatic of 5 to 18 ring atoms, where the hetero atoms are selected from N, O and S, such as pyridinyl, pyridazinyl, pyrimidinyl, pyrazinyl, furanyl, thiofuranyl, pyrrolinyl, indenyl, benzofuranyl, benzothiofuranyl, indolinyl, quinolinyl and isoquinolinyl; substituents on the heterocyclic aromatic nucleus are selected from the same group as the carbocyclic aromatic nuclei.

Q can also be an aliphatic group; these tend to result in lower thermal resistance and are thus useful where thermal properties are not essential.

D is substituted or unsubstituted hydrocarbylene such as branched or linear alkylene of up to 12 carbon atoms or said alkylene interrupted in the chain by phenylene. $R^1$, $R^2$, $R^3$, $R^4$, $R^5$ and $R^6$ each independently is unsubstituted or substituted hydrocarbyl such as alkyl of 1 to 12 carbon atoms, alkenyl of 2 to 12 carbon atoms, alkynyl of 2 to 12 carbon atoms, cycloalkyl of 4 to 8 carbon atoms, phenyl, alkylphenylene where the alkyl group contains 1 to 12 carbon atoms, phenylalkylene where the alkylene group contains 1 to 12 carbon atoms, alkenylphenylene with 2 to 12 carbon atoms in the alkenyl group. When substituted, these hydrocarbyl groups can be substituted by Br, Cl, I, F, —NC, —NO$_2$, —OCN, alkoxy of 1 to 8 carbon atoms, —S—(C$_1$-C$_8$) alkyl,

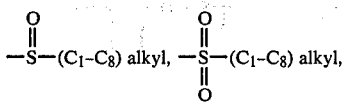

—S—S—(C$_1$-C$_8$) alkyl, —COOH, —COSH, —CSOH, —CONH$_2$, —CN, —CHO, —CHS, —OH, —SH and —NR$_7$R$_8$ where R$_7$ and R$_8$ independently are hydrogen or lower alkyl.

x, y and z each independently has a value from 0 to 100.

In a narrower embodiment, x, y and z are all zero, Q is mono-carbocyclic aromatic and the polysiloxane unit has the formula

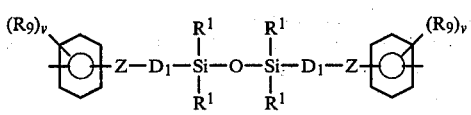

where
v is 0 to 4
R$_9$ is lower alkyl, lower alkenyl, lower alkynyl, cycloalkyl of 4 to 8 carbon atoms, lower alkoxy, lower alkylthio, phenyl, loweralkylphenylene, phenylloweralkylene, loweralkenylphenylene, phenoxy, phenylthio, loweralkylcarbonyl, loweralkylcarbonyloxy, loweralkoxycarbonyl, bromo, chloro, fluoro, iodo, nitro, cyano, cyanthio, carboxyl, carbonyl, hydroxyl, mercapto, and mercaptocarbonyl;
Z is

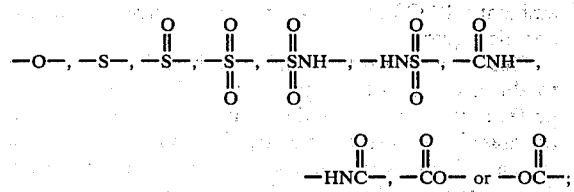

D$_1$ is methylene or alkylene of 3 to 8 carbon atoms;
R$^1$ is lower alkyl, lower alkenyl, lower alkynyl, phenyl, loweralkylphenylene, phenylloweralkylene, or loweralkenylphenylene.

In this embodiment the units of particular interest are those units where
v is 0 or 1
D$_1$ is methylene or alkylene of 3 to 8 carbon atoms and notably those where
v is 0 or 1
D$_1$ is methylene or alkylene of 3 to 8 carbon atoms and
R$_1$ is lower alkyl In a particularly preferred configuration of this embodiment,
v is 0
D is methylene, propylene or butylene, and
R$^1$ is alkyl of 1 to 3 carbon atoms.

In a specific embodiment, polymers contain the unit of formula:

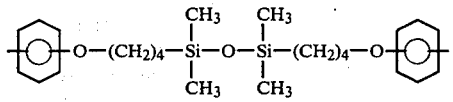

In another embodiment, the unit has the formula:

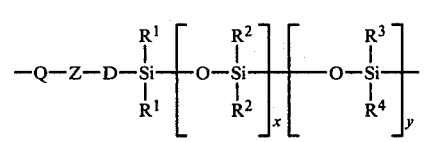

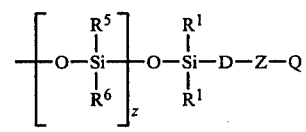

where Q, Z and D are as previously defined and
x has a value from 0 to 100
y has a value from 0 to 20
z has a value from 0 to 20
R$^1$ is unsubstituted hydrocarbyl of 1 to 18 carbon atoms;
R$^2$ is alkyl of 1 to 12 carbon atoms;
R$^3$ is phenyl or alkylphenylene of 7 to 18 carbon atoms;
R$^4$ is alkyl of 1 to 12 carbon atoms, phenyl or alkylphenylene of 7 to 18 carbon atoms;
R$^5$ is alkenyl of 2 to 12 carbon atoms or substituted alkyl of 1 to 12 carbon atoms;
R$^6$ is alkyl of 1 to 12 carbon atoms, phenyl, alkylphenylene of 7 to 18 carbon atoms, alkenyl of 2 to 12 carbon atoms or substituted alkyl of 1 to 12 carbon atoms.

In the narrower embodiments, Q is mono-carbocyclic aromatic and the polysiloxane unit has the formula

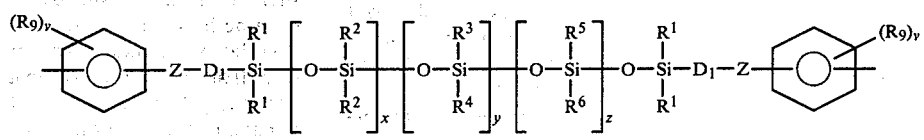

where
v is 0 to 4
R$_9$ is as previously defined
Z is

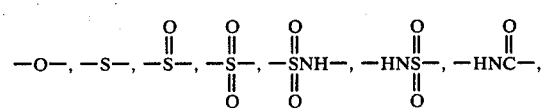

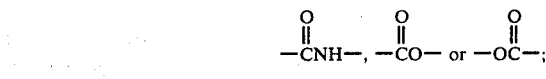

D$_1$ is methylene or alkylene of 3 to 8 carbon atoms;

$R^1$ is lower alkyl, lower alkenyl, lower alkynyl, phenyl, lower alkylphenylene or phenyl lower alkylene;

$R^2$ is alkyl of 1 to 12 carbon atoms;

$R^3$ is phenyl, alkyl phenylene of 7 to 18 carbon atoms or alkyl of 1 to 12 carbon atoms;

$R^4$ is alkyl of 1 to 12 carbon atoms, phenyl, alkylphenylene of 7 to 18 carbon atoms, alkenyl of 2 to 12 carbon atoms or substituted alkyl;

$R^5$ is alkenyl of 2 to 12 carbon atoms or substituted alkyl of 1 to 12 carbon atoms;

$R^6$ is alkyl of 1 to 12 carbon atoms, phenyl, alkylphenylene of 7 to 18 carbon atoms, alkenyl of 2 to 12 carbon atoms or substituted alkyl of 1 to 12 carbon atoms, where the substituents are as previously indicated;

x has a value from 0 to 100 y has a value from 0 to 20 and z has a value from 0 to 20.

In a narrower embodiment, v is 0 or 1

$D_1$ is methylene or alkylene of 3 to 8 carbon atoms.

$R^1$ is lower alkyl $R^2$ is lower alkyl $R^3$ is lower alkyl or phenyl $R^4$ is lower alkyl, phenyl, lower alkenyl or substituted lower alkyl.

$R^5$ is lower alkenyl or substituted lower alkyl.

$R^6$ is lower alkyl, lower alkenyl or substituted lower alkyl, the substituents on $R_4$, $R_5$ and $R_6$ lower alkyls being independently selected from halogen, amino, cyano, $-CONH_2$, hydroxyl, and mercapto;

x has a value from 0 to 100 y has a value from 0 to 20 and z has a value from 0 to 20.

In a still narrower embodiment, v is 0 or 1

Z is $-O-$ or $-S-$ $D_1$ is methylene, propylene or butylene;

$R_1$ is alkyl of 1 to 3 carbon atoms;

$R_2$ is alkyl of 1 to 3 carbon atoms;

$R^3$ is alkyl of 1 to 3 carbon atoms or phenyl;

$R^4$ is alkyl of 1 to 3 carbon atoms, alkenyl of 2 to 4 carbon atoms or said alkyl substituted by amino, cyano, hydroxyl or $-CONH_2$;

$R^5$ is alkenyl of 2 to 4 carbon atoms or alkyl of 1 to 3 carbon atoms substituted by amino, cyano, hydroxyl or $-CONH_2$;

$R^6$ is alkyl of 1 to 3 carbon atoms, alkenyl of 2 to 4 carbon atoms or alkyl of 1 to 3 carbon atoms substituted by amino, cyano, hydroxyl or $-CONH_2$; and x, y and z are as previously defined.

The preparation of some compounds of general formula

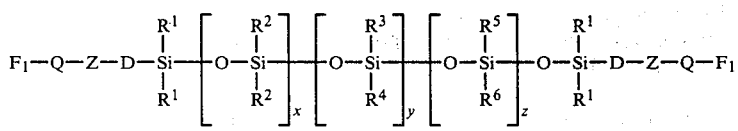

is known in the prior art. Thus, British Pat. No. 1,062,418, published March, 1967 discloses that linear polysiloxanes of formula

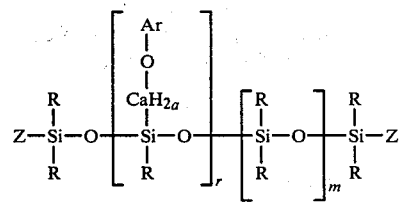

where the R groups, which may be the same or different, are mono-valent organic groups, Z is a mono-valent organic group, a nitroaryloxyalkyl group, an aminoaryloxyalkyl group or an aminonitroaryloxyalkyl group and r and m, which may be the same or different, are zero or positive integers, can be prepared by reacting together the sodium salt of a suitably substituted phenol or naphthol with a haloalkylsiloxane of suitable formula such as γ-haloalkyl siloxane. The reaction is conducted at a temperature of 20° to 200° C. in a solvent such as methanol or ethanol at pressures ranging from atmospheric to 40 atmospheres.

It has been found that yields on the order of 85% or greater can be can be achieved when a compound of formula $$F_1\text{-}Q\text{-}Z\text{-}M$$

where $F_1$, Q and Z are all as previously defined and M is an alkali or alkaline earth metal is reacted with a bis (halohydrocarbyl) disiloxane of formula

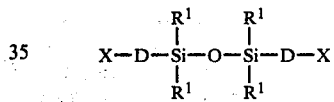

where D and $R^1$ are as previously defined and X is Cl, Br or I at ambient pressure, at a temperature of from ambient (20° C.) to 200° C. in the presence of a dipolar aprotic liquid.

This reaction is often highly exothermic and sensitive to the presence of oxygen. The reaction is therefore preferably conducted under an inert atmosphere and in the absence of even trace amounts of water if one of the reactants is an alkoxy- or aryloxysilane or -polysiloxane. The reaction medium contains a dipolar, aprotic liquid such as dimethyl sulfoxide, N,N-dimethylformamide, tetramethylurea, N-methyl-2-pyrrolidone or hexamethylphosphoramide. The dipolar, aprotic liquid constitutes from 1 to 100% by weight of the reaction medium, preferably from 20 to 50% by weight. Any remaining portion of the reaction medium consists essentially of at least one liquid hydrocarbon boiling from 40° to about 200° C. under atmospheric pressure. The purpose of the liquid hydrocarbon is to facilitate the removal, by azeotropic distillation, of any water present in the reaction mixture. Preferably, the bis (haloalkyl) siloxane is gradually added under anhydrous conditions to a reaction mixture containing the aforementioned metal salt and a dipolar, aprotic solvent. When the addition is complete and any exothermic reaction has subsided, it is often desirable to heat the reaction mixture at from 70° to about 150° C. for several hours to ensure substantially complete conversion of the reactants to the desired product. The present compounds, many of which are colorless, high-boiling, viscous oils, are soluble in the reaction medium and readily isolatable by removal of the aforementioned dipolar aprotic liquid and any liquid hydrocarbon present. Some of the compounds may darken if exposed to light or air for extended periods of time.

It is believed that the dipolar aprotic liquids function by their ability to solvate both salts and organic substrates. Further, these materials being cationic solvating compounds, leave the anion associated with the cation unencumbered and reactive. The dipolar aprotic liquids, while effective, are often costly, frequently hard to purify, dry and maintained in an anhydrous state, and they are difficult to recover once the reaction is complete. It has been found that the dipolar aprotic solvents can be eliminated and the disiloxanes can be prepared in virtually any non-polar solvent, such as a straight hydrocarbon solvent, in the presence of a phase transfer catalyst.

Thus, the reaction can be conducted in aliphatic hydrocarbon liquids such as hexane, heptane and octane, and aromatic hydrocarbon liquids such as the alkylated aromatics including toluene, xylene and mixtures thereof. The reaction can also be conducted in chlorinated hydrocarbon solvents such as chlorobenzene and dichlorobenzene.

The phase transfer catalyst is believed to proceed as follows. There are two immiscible phases, a hydrocarbon phase containing the disiloxane and a solid phase comprising the salt. Because the salt is insoluble in the hydrocarbon phase, there will be no reaction in the absence of interfacial phenomena. In the presence of a phase transfer catalyst, however, an exchange of anions between the catalyst and salt takes place; the anion capable of functioning as a nucleophile is brought into the hydrocarbon phase, where reaction can take place with product formation. Thus, the phase transfer process relies on the catalytic effect of certain compounds to solubilize, in organic solutions, otherwise insoluble anionic nucleophiles. The increased reactivity and solubility in nonpolar media allows the reaction to proceed at relatively moderate conditions.

Known phase transfer catalysts include the quaternary onium compounds, macrocyclic crown ethers and cryptates. The quaternary onium compounds are derivatives of phosphorous, arsenic, nitrogen, antimony or bismuth and have the general formula:

$(R_4M)_y^+(X)^{-y}$ where
each R is independently selected from alkyl of 1 to 20 carbon atoms, alkenyl of 2 to 20 carbon atoms aryl of 6 to 20 carbon atoms arylalkylene or alkylarylene of 7 to 40 carbon atoms;
M is P, As, N, Sb or Bi;
X is an anion; and
y is 1 or more, to balance the electron charge.

Quaternary phosphonium and ammonium compounds are generally the most available and therefore are preferred.

Typical anions include halide, sulfonate, sulfate, borate, fluoroborate, phosphate, bisulfate and fluorophosphate. The halides are most generally available.

Representative quaternary onium compounds include
tetrabutylammonium chloride
tetrabutylammonium bisulfate
cetyltrimethylammonium bromide
triphenylbenzylphosphonium chloride
tetrabutylammonium cyanide
tetrabutylammonium fluoride
tetrabutylammonium iodide
tetrabutylammonium hydrogen sulfate
tetrabutylphosphonium chloride
benzyltriethylammonium bromide
benzyltriethylammonium chloride
benzyltrimethylammonium chloride
benzyltrimethylammonium fluoride
hexadecyltriethylammonium bromide
hexadecyltriethylphosphonium bromide
hexadecyltrimethylammonium bromide
hexadecyltrimethylammonium chloride
dibutyldimethylammonium chloride
decyltriethylammonium bromide
hexadecyltributylphosphonium bromide
hexyltriethylammonium bromide
dodecyltriethylammonium bromide
methyltrinonylammonium chloride
methyltriphenylammonium bromide
octyltriethylammonium bromide
tricapylmethylammonium chloride
tetraethylammonium chloride
trioctylethylphosphonium bromide
trioctylmethylammonium chloride
trioctylpropylammonium chloride
tetrapropylammonium bromide
tetraphenylarsonium chloride
tetraphenylphosphonium chloride
tetraphenylphosphonium iodide
benzyltrimethylammonium hydroxide
tetradecyltrimethylammonium bromide
tetraethylammonium p-toluene sulfonate
tetramethylammonium tetrafluoroborate
tetrapropylammonium hexafluorophosphate The phase transfer catalyst can be a macrocyclic crown ether.

Macrocyclic crown ethers are well-known to those skilled in the art. C. J. Peterson in an article entitled "Cyclic Polyethers And Their Complexes With Metal Salts", *Journal of the American Chemical Society*, 89: 26, December, 1967, Pages 7017-36, describes macrocyclic crown ethers which are cyclic structures having 12 to 30 ring members. Many of the ring members are oxygen. Macrocyclic crown ethers are known to complex cations, such as alkali metals.

Other articles describing macrocyclic crown ethers are "Chemistry of the Preparation of Some Macrocycles", M. R. Crawford, S. E. Drewes and D. A. Scitton, *Chemistry and Industry*, Oct. 17, 1970, Pages 1351-1352 and "Synthesis of New Macrocycles Part 1, Monomeric and Dimeric O-Phthalate Esters", S. E. Drewes and P. C. Coleman, *Journal Chemical Society Parkin I*, 1972, Pages 2148-53.

The three crown ethers which have been most widely used are:

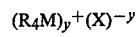

dibenzo-18-crown-6:

-continued

[structure: dibenzo-18-crown-6]

dicyclohexyl-18-crown-6:

[structure: dicyclohexyl-18-crown-6]

and 18-crown-6:

[structure: 18-crown-6]

Other crown ethers include benzo-15-crown-5, 12-crown-4, cyclohexyl-15-crown-5 and octamethylcyclotetrafurfurylene.

The phase transfer catalyst can also be a macrotricyclic diaminopolyether such as the 2.2.2-cryptate of formula

[structure: 2.2.2-cryptate]

The amount of phase transfer catalyst material required to effect the desired chemical reaction may vary from as little as 0.01 mole percent of the total starting material to 100 mole percent or greater. There is no benefit derived by the employment of molar quantities of 100 percent or greater, and such usage often becomes economically impractical. It is preferred to use from about 0.1 mole percent to 10 mole percent of phase transfer catalytic materials.

In practicing this process, the alkali metal salt $$F_1\text{-}Q\text{-}Z\text{-}M$$

is formed by reacting an appropriate precursor with an alkali metal hydroxide solution. Then an azeotroping solvent is added, the mixture refluxed and water removed to provide an anhydrous system. When no more water is being produced, the temperature is reduced to about 20° C. below the boiling point of the reaction mixture. At this point the phase transfer catalyst is added and the siloxane-containing halide is added dropwise to accomplish the coupling reaction. After addition is complete, the mixture is maintained at a temperature of 60° to 200° C. for from 3 to 12 hours to complete the reaction. The mixture is filtered to remove salts and the product recovered by distillation.

The preparation techniques discussed to this point are related to disiloxanes, i.e., the case where x, y and z is each 0. It is possible however to open the disiloxane chain and insert a plurality of $$\begin{array}{c} R^{2-6} \\ | \\ -\text{SiO}- \\ | \\ R^{2-6} \end{array}$$

units, where $R^{2-6}$ indicates a member selected from the group defining, $R^2$, $R^3$, $R^4$, $R^5$ and $R^6$.

The technique is of interest where it is desired to modify the properties of the disiloxane unit. For example, as the value of x, y and z increases, the siloxane unit becomes more elastomeric and polymers containing the same will become more flexible. Further, by incorporating an alkenyl or alkynyl-containing siloxy unit, the polysiloxane can be cross-linked to provide a tougher, less elastomeric polymer.

The siloxy groups of formula $$\begin{array}{c} R^{2-6} \\ | \\ -\text{Si}-\text{O}- \\ | \\ R^{2-6} \end{array}$$

are obtained from cyclic polysiloxanes of general formula $$\left[ \left( \begin{array}{c} R^{2-6} \quad R^{2-6} \\ \diagdown \diagup \\ \text{Si}-\text{O} \end{array} \right)_s \right]_t$$

where
$R^{2-6}$ is as previously defined
s is 3 or greater
t is 0 or an integer between 1 and 100
When t is 2 or more, the R groups on any silicon atom are independent of any other R groups. Since a siloxy group of formula $$\begin{array}{c} R^{2-6} \\ | \\ -\text{Si}-\text{O} \\ | \\ R^{2-6} \end{array}$$

is being inserted into the disiloxane and these groups are obtained from a cyclic polysiloxane, it is apparent that the cyclic polysiloxane undergoes scission to become a source of the groups. Thus, for example, the molecule hexamethylcyclotrisiloxane cleaves according to the following pattern to provide three dimethylsiloxy groups:

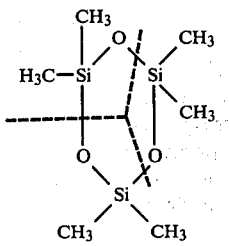

In practice, the disiloxane is simply heated at a temperature of from about 85° to about 250° C. with an appropriate source of siloxy groups, or mixture, in the presence of a catalyst. When the substituents on Q are basic, such as amino, or neutral such as halogen, the catalyst will be an alkali metal hydroxide, a quaternary ammonium hydroxide, a quaternary phosphonium hydroxide, a quaternary ammonium or phosphonium silanolate with or without the incorporation of a macrocyclic crown ether. Typical catalysts include potassium and sodium hydroxide, tetramethyl ammonium hydroxide and tetrabutyl phosphonium hydroxide.

When the substituents on Q are acidic in character, such as carboxyl and phenolic hydroxyl, the catalyst will be a strong acid such as hydrogen chloride, sulfuric, trifluoroacetic, trifluoromethanesulfonic and other organosulfonic acids.

The catalyst can be used in an amount ranging from 30 to 50 parts of catalyst per million parts by weight of silicon compounds present to form 3 to 5 percent by weight of the silicon compounds.

To obtain a unit of given value for x, y and z one reacts one mole of disiloxane with that amount of a compound capable of yielding x moles of the siloxy group:

with that amount of a compound capable of yielding y moles of the siloxy group

and with that amount of a compound capable of yielding z moles of the siloxy group

The chemical reaction is complete when the viscosity of the reaction mixture reaches a constant level or when the temperature of the reaction mixture can be raised to a level above that of the highest boiling cyclic polysiloxane starting material. Another indication of complete reaction is the change in the solution from a two-phase or multi-phase mixture to a single phase reaction mixture.

When the reaction is complete, the catalyst is neutralized. Where the catalyst is a quaternary ammonium or phosphonium silanolate, heating to about 160°–170° C. will effect decomposition. The basic catalysts can be neutralized with mineral acid while the acid catalysts can be neutralized with an alkali metal hydroxide or carbonate.

The reaction mixture is thereafter cooled, filtered and, if desired, distilled under reduced pressure to recover the product in pure form.

The percentage of functional groups in the final product is determined by titration, in known manner.

As indicated previously, the disiloxane is reacted with a compound capable of generating a desired siloxy group. Such compounds include:
hexamethylcyclotrisiloxane
octaphenylcyclotetrasiloxane
octamethylcyclotetrasiloxane
1,3,5,7-tetramethyl-1,3,5,7-tetravinylcyclotetrasiloxane and
1,3,5,7-tetramethyl-1,3,5,7-tetraphenylcyclotetrasiloxane.

The polysiloxanes can be incorporated into a variety of polymeric compositions to modify the properties thereof. The polysiloxanes impart flexibility, elongation and impact resistance; they impart resistance to U.V. and other radiation, resistance to ozone, resistance to corona discharge and resistance to oxidation; they lower the glass transition temperature (Tg) which facilitates processing and fabrication of high molecular weight materials; they lower the surface tension and reduce the coefficient of friction; they increase solubility, increase resistance to acid and increase permeability to gases.

Among the more significant properties contributed by these polysiloxane units is their surprising heat resistance. As a consequence of their thermal stability, one can obtain higher molecular weight compositions than is possible using prior art materials; further, these polysiloxanes and compositions containing them can be processed at elevated temperatures. In addition, the presence of the aromatic group imparts improved resistance to corrosion because there is a reduced tendency to form salts with metals and corrode or contaminate a given system.

The relationship of the present polysiloxane units to various polymeric compositions will be discussed in detail with respect to each of these compositions.

1. Polyamides

Polyimides are prepared by reacting a dianhydride with a diamine:

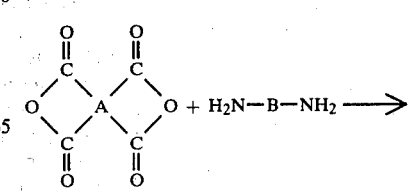

-continued

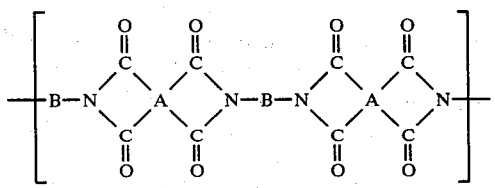

Polyimides containing silicon have been prepared using bis-aminoalkylene siloxanes as part or all of the diamine; such polyimides are illustrated by U.S. Pat. Nos. 3,740,305 and 4,030,948. These polyimides, while useful as protective coatings for semiconductors and other electronic devices, suffer from the defect that they are insoluble in virtually all of the common organic solvents. The half-amide, however, is soluble and so it has been the practice to form the half-amide:

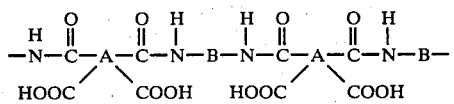

and to provide the half-amide, in suitable solvent such as dimethyl sulfoxide or N-methyl pyrrolidone to the ultimate user. This solution is applied to the substrate and the coated substrate is thereafter heated to evaporate the solvent and to convert the half-amide to the corresponding polyimide:

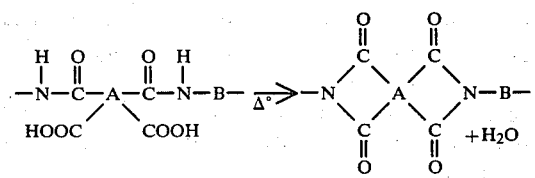

This procedure has several significant drawbacks. First, is the requirement that the substrate be exposed to temperatures on the order of 150° to 300° C. required to convert the half-amide to the imide; many semiconductor devices cannot accept these temperatures. Second is the proposition that if imidization is not complete, the amide linkages will gradually hydrolyze, causing degradation of the protective coating; this is particularly so under acid conditions. Third is the requirement that a protective coating be built up gradually from a succession of very thin coatings. If a thick coating is applied and heated to effect conversion of the half-amide to the imide, the water formed during the reaction can be converted to steam, which tends to produce voids in the coating. Further, as the imidization proceeds from the surface downward, the bottom of the coating is insulated from the heat; this makes completion of the imidization reaction difficult to achieve, or even to identify. Thus, it is necessary for the ultimate user to engage in a series of coating, heating and cooling cycles in order to develop an acceptable protective coating. Additionally, incomplete imidization presents usage problems in connection with electrical and electronic devices; the poly (half-amide), because of the free carboxylic acid group, will conduct electricity and can contribute to leakage and to deterioration of a device. Stated another way, the electrical dissipation factor is higher for the poly (half-amide) than for the corresponding polyimide. Finally, the presence of water produced by the imidization reaction is unacceptable in a semiconductor environment, where moisture can drastically reduce the useful life of a component.

It is now possible to have a polyimide capable of being applied as a protective coating in the form of an imide rather than in the form of a polyhalf-amide so as to eliminate the problems associated with applying and reacting the half-amide.

Polyimides containing the unit

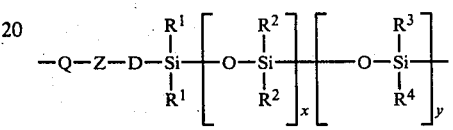

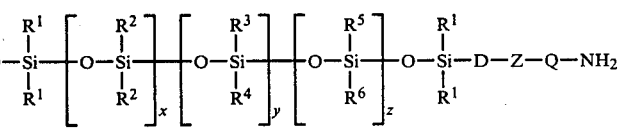

display unexpected properties that make them suited for a variety of applications.

In one aspect, the invention relates to polyimide compositions containing said polysiloxane. In one embodiment of this aspect, the invention relates to the polyimide reaction product of a dianhydride with a bis-(amino)polysiloxane of formula

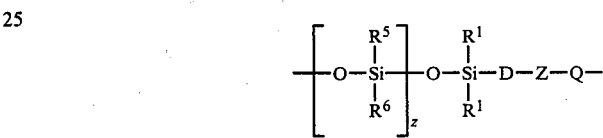

in another embodiment of this aspect, the invention relates to the polyimide reaction product of a dianhydride, an organic diamine and the indicated bis(amino)-polysiloxane.

In another aspect, it has been found that polyimides containing the siloxane unit described above are soluble in conventional solvents, such as halogenated aromatic hydrocarbons and dipolar solvents. In an embodiment of this aspect, the invention relates to solutions of polyimides, to polyimide coatings applied by evaporation of solvents, to films cast and to fibers spun from solutions of these polyimides.

In another aspect of the invention, the siloxane-containing polyimides have been found to be thermoplastic, capable of being formed and shaped as by molding, extruding or calendering. In an embodiment of this aspect, the invention relates to molding compositions comprising a siloxane-containing polyimide.

In yet another aspect of this invention, the siloxane containing polyimides have been found to possess improved adhesion to a variety of substrates. In one embodiment of this aspect the polyimides are employed as wire coatings and as coatings for filaments of metal, glass and ceramic. In another embodiment, the polyimides are used as adhesives. In still another embodiment, the polyimides are used as primers or adhesion promoters between a substrate, such as glass, metal and ceramic, and a matrix such as epoxy, polyester, phenolic and rubber. They are also used as hot melt adhesives.

The reaction between the diamine and dianhydride proceeds stepwise, with the formation of the poly (half-amide) being the first step and cyclization to the polyimide being the second step. As indicated, the half-amide is more soluble than the polyimide and for certain coatings applications, where the polyimide has been formulated to be highly resistant to solvents or even thermoset, it is necessary to apply the half-amide and thereafter cure in situ. One aspect of the invention therefore relates to the poly (half-amide) intermediate containing the indicated siloxane unit.

The siloxane-containing polyimides of this invention include the reaction product of an aromatic or aliphatic tetracarboxylic acid dianhydride with a polysiloxane of formula

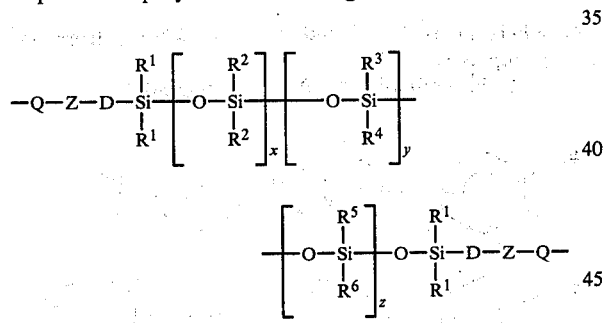

where the various elements are all as previously defined to provide a polyimide containing the unit

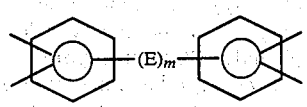

As indicated, Q can be carbocyclic aromatic, such as phenylene, naphthylene, anthracenylene and phenanthrylene, that is optionally substituted. The substituents on Q can be any that do not interfere with the ability to react to form an imide. Thus, Q can be substituted by from 1 to 4 substituents, as previously defined.

As indicated, polyimides are prepared by the reaction of a dianhydride with a diamine. The dianhydride can be represented by the formula

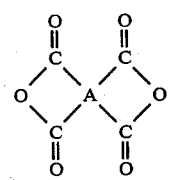

where A is the tetravalent residue of a tetracarboxylic acid anhydride. Thus, the polyimide will contain at least one unit of formula:

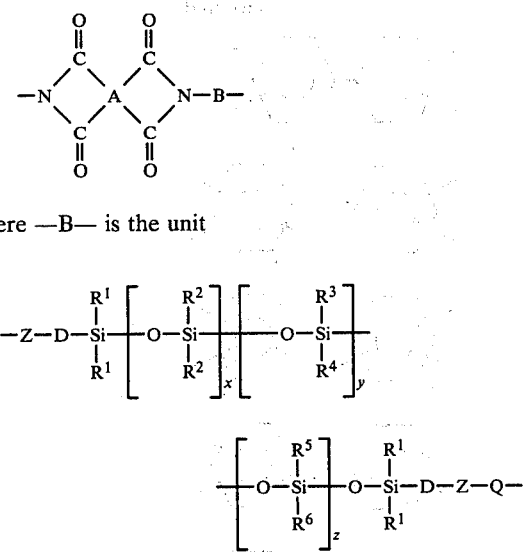

where —B— is the unit

In the dianhydride of general formula

A is a tetravalent radical selected from substituted and unsubstituted aliphatic, cycloaliphatic, heterocyclic, aromatic groups and combinations thereof. Thus, A, can be a tetravelent benzene or naphthalene nucleus or a tetravalent group of formula

where m is 0 or 1 and E is —O—, —S—, $$-S-, -\underset{\underset{O}{\overset{O}{\|}}}{S}-, -\overset{O}{\underset{\|}{C}}-,$$

or —C$_y$H$_{2y}$— where y is an integer from 1 to 8.
In this embodiment, A is illustrated by:

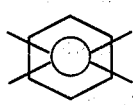

-continued

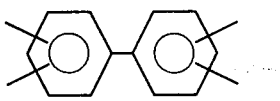
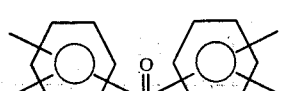
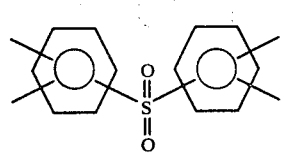
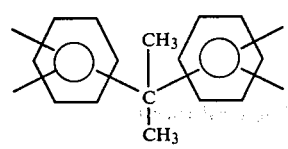
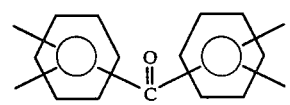

and specific anhydrides include
pyromellitic dianhydride,
3,3',4,4'-benzophenone tetracarboxylic dianhydride
2,2',3,3',-benzophenone tetracarboxylic dianhydride,
3,3',4,4',-diphenyl tetracarboxylic dianhydride,
2,2',3,3'-diphenyl tetracarboxylic dianhydride,
2,2-bis-(3,4-dicarboxyphenyl) propane dianhydride,
2,2-bis-(2,3-dicarboxyphenyl) porpane dianhydride,
Bis-(3,4-dicarboxyphenyl) ether dianhydride,
Bis-(3,4-dicarboxyphenyl) sulfone dianhydride
Bis-(3,4-dicarboxyphenyl) sulfide dianhydride
1,1-bis-(2,3-dicarboxyphenyl) ethane dianhydride,
1,1-bis-(3,4-dicarboxyphenyl) ethane dianhydride,
Bis-(2,3-dicarboxyphenyl) methane dianhydride
Bis-(3,4-dicarboxyphenyl) methane dianhydride,
2,3,6,7-naphthalene tetracarboxylic dianhydride,
1,2,4,5-naphthalene tetracarboxylic dianhydride,
1,2,5,6-naphthalene tetracarboxylic dianhydride,
Benzene-1,2,3,4-tetracarboxylic dianhydride
Perylene-3,4,9,10-tetracarboxylic dianhydride
Pyrazine-2,3,5,6-tetracarboxylic dianhydride
Thiophene-2,3,4,5-tetracarboxylic dianhydride
naphthalene-1,4,5,8-tetracarboxylic dianhydride
decahydronaphthalene-1,4,5,8-tetracarboxylic dianhydride
4,8-dimethyl-1,2,3,5,6,7-hexahydronaphthalene-1,2,5,6-tetracarboxylic dianhydride
2,6-dichloronaphthalene-1,4,5,8-tetracarboxylic dianhydride
2,7-dichloronaphthalene-1,4,5,8-tetracarboxylic dianhydride
2,3,6,7-tetrachloronaphthalene-1,4,5,8-tetracarboxylic dianhydride
phenanthrene-1,8,9,10-tetracarboxylic dianhydride
cyclopentane-1,2,3,4-tetracarboxylic dianhydride
pyrrolidine-2,3,4,5-tetracarboxylic dianhydride
pyrazine-2,3,5,6-tetracarboxylic dianhydride
1,2,3,4-butane tetracarboxylic dianhydride
3,4,3',4'-benzophenone tetracarboxylic dianhydride
azobenzene tetracarboxylic dianhydride
2,3,4,5-tetrahydrofuran dianhydride
p-phenylenebis(trimellitate) anhydride
1,2-ethylenebis(trimellitate) anhydride
2,2-propanebis(p-phenylene trimellitate) anhydride
4,4'-{p-phenylenebis(phenylimino)carbonyl diphthalic}anhydride
4,4'-diphenylmethanebis(trimellitamide) anhydride and mixtures thereof.

A can also be the tetravalent residue of formula

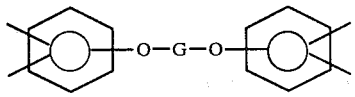

where G is phenylene or a group of formula

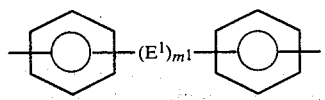

where $m^1$ is 0 or 1 and $E^1$ is selected from the same group as E.

In this embodiment, A is illustrated by

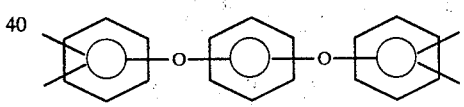

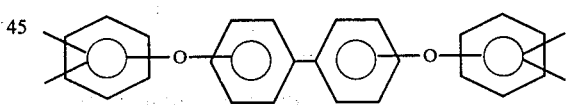

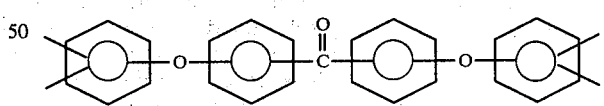

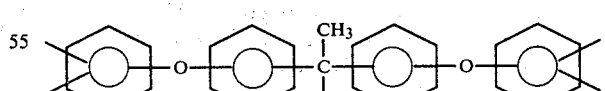

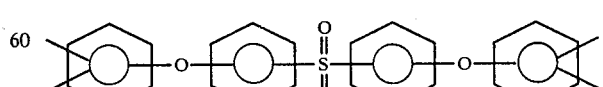

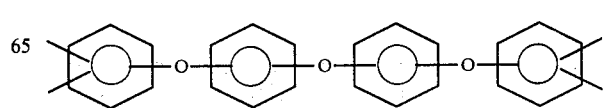

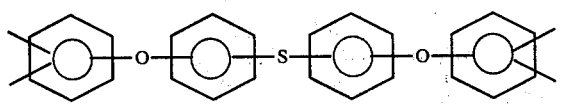

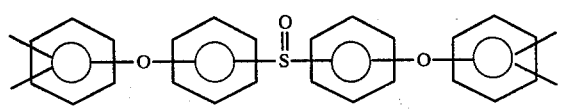

Similarly, and by analogy, the ether linkage can be replaced by

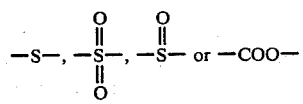

to provide useful dianhydrides.

Because of relative availability, some of the preferred species of aromatic dianhydrides are:
pyromellitic dianhydride
benzophenone tetracarboxylic acid dianhydride
diphenyl tetracarboxylic acid dianhydride
bis (3,4-dicarboxyphenyl) sulfone dianhydride
2,2-bis(3,4-dicarboxyphenyl) propane dianhydride
2,2-bis[4,4'-di(3,4-dicarboxyphenoxy)phenyl]propane dianhydride
p-bis(3,4-dicarboxypenoxy) phenyl dianhydride
4,4'-bis(3,4-dicarboxyphenoxy) diphenyl dianhydride
bis-[4,4'-di(3,4-dicarboxyphenoxy)phenol]sulfone dianhydride
bis[4,4'-di(3,4-dicarboxyphenoxy)phenyl]sulfide dianhydride The anhydride can also be aliphatic in nature, such as cyclopentane tetracarboxylic acid dianhydride, cyclohexane tetracarboxylic acid dianhydride and butane tetracarboxylic acid dianhydride.

The ether containing anhydrides can be prepared by coupling an appropriate xylene derivative, such as 4-bromoxylene or the alkali metal phenoxide of 4-xylenol, with an appropriate halide or aryloxide, via the Ullman Synthesis, using copper catalyst, followed by oxidation of the aromatic methyl groups and dehydration to effect ring closure.

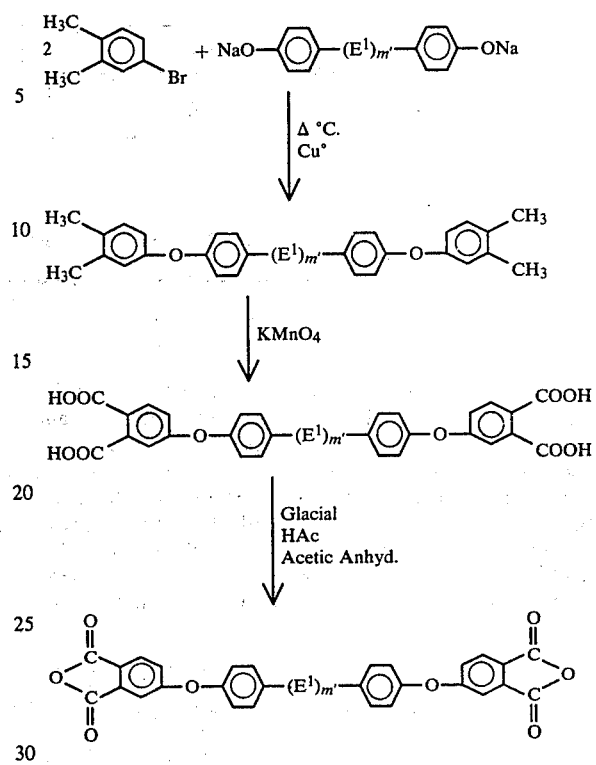

The anhydride component can be used alone or in combination with one or more other anhydrides.

The anhydride can also contain a siloxane and in another embodiment wherein A is a tetravalent residue of formula

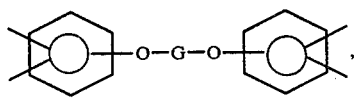

G can be a polysiloxane-containing group of formula

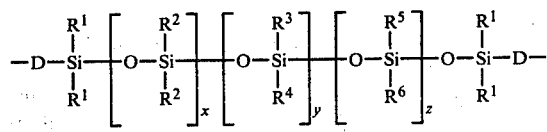

or.

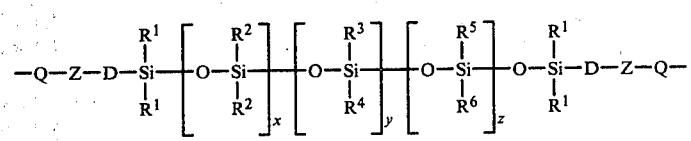

where the various elements are as previously described.

There is thus provided a variety of polysiloxane-containing dianhydrides of formulae

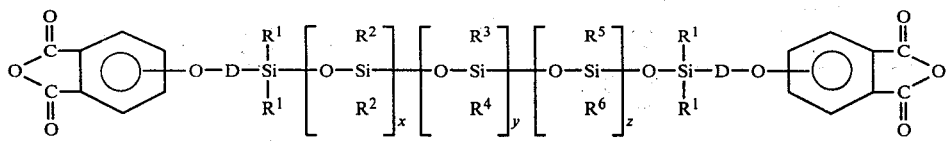

and

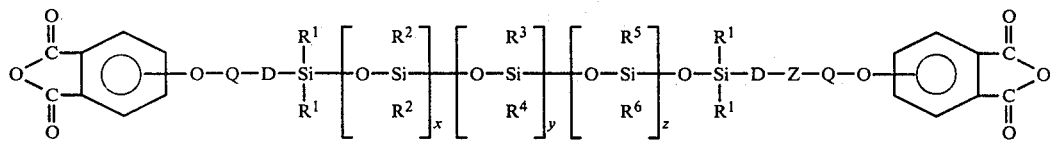

capable of incorporating the polysiloxane into a polyimide to provide the beneficial aspects of the siloxane unit therein, and capable of incorporating the polysiloxane unit into such other polymers as epoxy resins, where their presence provides for greater flexibility than is now possible, together with the surprising temperature stability previously discussed. These anhydrides are believed to be new, and in connection therewith the anhydrides may be presented by the formula

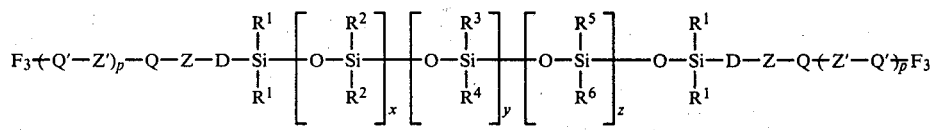

where
p=0 or 1;
Q' is selected from the same group as Q;
Z' is selected from the same group as Z; and
$F_3$ is

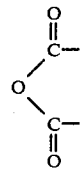

where the carbonyl groups are located ortho to each other on Q' or Q, and the other elements are as previously defined.

The preferred embodiments, because of relative ease of synthesis are these dianhydrides where
p=0 or 1
Q and Q', each, is a phenyl group
Z and Z', each, is oxygen or sulfur
D is methylene, propylene, or butylene
x has a value from 0 to 100
y has a value from 0 to 20
z has a value from 0 to 20
$R^1$ is lower alkyl;
$R^2$ is lower alkyl;
$R^3$ is lower alkyl or phenyl;
$R^4$ is lower alkyl, phenyl, lower alkenyl or substituted lower alkyl;
$R^5$ is lower alkenyl or substituted lower alkyl;
$R^6$ is lower alkyl, lower alkenyl or substituted lower alkyl; the substituents on $R_4$, $R_5$ and $R_6$ lower alkyls being independently selected from halogen, amino, cyano, —$CONH_2$, hydroxyl, and mercapto.

As described, the polyimides are formed from the reaction of a dianhydride and a diamine. The diamine can comprise solely one or more bis-amino polysiloxanes, as described, or it can comprise one or more organic diamines in addition to a bis-aminopolysiloxane. The organic diamine can have the general formula $H_2N$—Y—$NH_2$ where Y is the divalent residue. Y can be aliphatic, including alkylene of 1 to 20 carbon atoms or cycloalkylene of 4 to 8 carbon atoms. In the preferred embodiment, to provide superior properties, Y is the residue of an aromatic diamine. Thus, Y can be phenylene, diphenylene, naphthylene or a group of formula

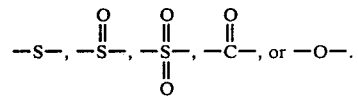

where $R^5$ is branched or linear alkylene of 1 to 20 carbon atoms,

The aryl nuclei can be substituted by lower alkyl, lower alkoxy or ther noninterfering groups.

Among the organic diamines that are useful are:
m-phenylenediamine;
p-phenylenediamine;
4,4'-diaminodiphenylpropane;
4,4'-diaminodiphenylmethane (hereinafter referred to as "methylenedianiline");
benzidine;
4,4'-diaminodiphenyl sulfide;
4,4'-diaminodiphenyl sulfone;
4,4'-diaminodiphenyl ether;
1,5-diaminonaphthalene;
3,3'-dimethylbenzidine;
3,3'-dimethoxybenzidine;
2,4-bis($\beta$-amino-t-butyl)toluene;
bis(p-$\beta$-amino-t-butyl)phenyl ether;

bis(p-β-methyl-o-aminopentyl)benzene;
1,3-diamino-4-isopropylbenzene;
1,2-bis(3-aminopropoxy)ethane;
m-xylylenediamine;
p-xylylenediamine;
bis(4-aminocyclohexyl)methane;
decamethylenediamine;
3-methylheptamethylenediamine;
4,4'-dimethylheptamethylenediamine;
2,11-dodecanediamine;
2,2-dimethylpropylenediamine;
octamethylenediamine;
3-methoxyhexamethylenediamine;
2,5-dimethylhexamethylenediamine;
2,5-dimethylheptamethylenediamine;
3-methylheptamethylenediamine;
5-methylnonamethylenediamine;
1,4-cyclohexanediamine;
1,12-octadecanediamine;
bis(3-aminopropyl)sulfide;
N-methyl-bis-(3-aminopropyl)amine;
hexamethylenediamine;
heptamethylenediamine;
nonamethylenediamine; and mixtures thereof.

$R_5$ can also be the group of formula —O—G'—O— where G' is phenylene or a group of formula

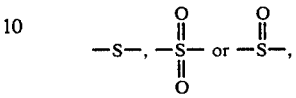

where $m^3$ is 0 or 1 and $E^3$ is $$-O-, -S-, -\overset{O}{\underset{}{S}}-, -\overset{O}{\underset{O}{S}}-, -\overset{O}{\underset{}{C}}-$$

or linear or branched alkylene of 1 to 8 carbon atoms.

This embodiment, which is believed to be novel, is illustrated by the following diamines:

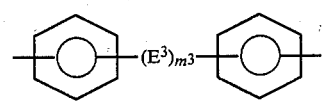

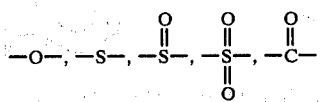

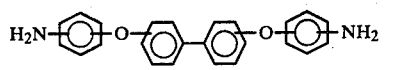

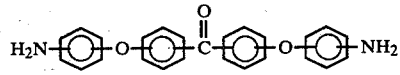

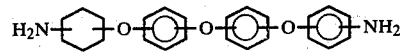

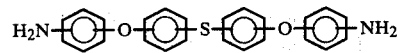

-continued

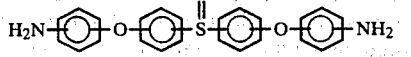

Similarly, and by analogy, the ether linkage can be replace by $$-S-, -\overset{O}{\underset{}{S}}- \text{ or } -\overset{O}{\underset{O}{S}}-,$$

to provide amines.

The diamines impart solubility to polyimides fabricated with them. They can be used as the sole amine component of a polyimide, they can be used in conjunction with other diamines and can be used in conjunction with the bis(amino) polysiloxane, with or without other diamines, to provide polyimides whose properties such as Tg and solubility can be tailored for specific applications.

Y can also be the residue of a diamine macrocyclic crown ether.

Additionally, one can use a functionally substituted diamine as part of the diamine component to provide functional sites for grafting and cross-linking, for modifying the polyimide to become photosensitive, hydrophilic, antiseptic, fungicidal and the like.

The functionally substituted amine will have the general formula $$NH_2-Y-NH_2 \text{ or}$$
$$\underset{F^3}{|}$$

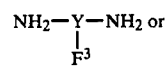

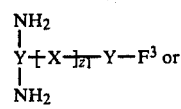

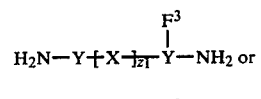

where Y is an aromatic nucleus, X and $X_a$, independently, are $$-O-, -S-, -\overset{O}{\underset{O}{S}}-,$$

linear or branched alkylene of 1 to 20 atoms, or a carbocyclic or heterocyclic group containing from 6 to 14 atoms in the nucleus and the hetero atoms are selected from N, S and O.

$z_1$ and $z_2$, each independently, is 0 or 1 and when $z_1$ and/or $z_2$ is 0, the adjacent aromatic nuclei may be fused, and $F^3$ is a functional group.

The term "functional group" is intended to denote atoms or groups of atoms that confer characteristic chemical properties on the molecule containing said atoms. Thus, it will be apparent that the chemical composition of the functional group $F^3$ can vary, depending on the characteristic chemical properties desired. $F^3$ can be acrylyl, methacrylyl or other unsaturated group capable of free-radical initiated cross-linking; it can be the naphthoquinone-diazide radical to provide U.V. sensitivity; it can be a quaternary ammonium group to provide fungicidal activity or increased hydrophilicity. $F^3$ can also be $$-\overset{O}{\underset{\|}{C}}-O-R_m$$

$$-O-\overset{O}{\underset{\|}{C}}-R_m$$

$$-\overset{O}{\underset{\|}{C}}-R_m$$

$-O-R_m$
Cl, Br, I or F $$-\overset{O}{\underset{\|}{C}}H$$

$-SH$
$-SR_m$
$-OH$
$-SO_3H$
$-COOH$ $$-\overset{O}{\underset{\underset{O}{\|}}{\overset{\|}{S}}}-R_m$$

$$-\overset{O}{\underset{\|}{C}}-N\overset{Rn}{\underset{Rp}{\diagdown}}$$

$-CN$
$-OCN$
$-NCO$ or $$-N\overset{Rn}{\underset{Rp}{\diagdown}}$$

where Rm is hydrogen, alkyl of 1 to 7 carbon atoms or alkenyl of 2 to 7 carbon atoms.

Rn and Rp each independently is hydrogen, alkyl of 1 to 7 carbon atoms, alkenyl of 2 to 7 carbon atoms, or $-C-Rq$ where Rq is alkyl of 1 to 7 carbon atoms.

Aromatic nucleus Y can be mono-carbocyclic aromatic or polycarbocyclic aromatic of 6 to 14 carbon atoms such as benzene, naphthalene anthracene etc. These nuclei can be further substituted by non-interfering groups, such as lower alkyl.

The nucleus Y can also be heterocyclic aromatic of 6 to 20 atoms while the hetero atoms are one or more of N, O and S, such as pyridine, pyrimidine, pyrazine, oxadiazine, oxathiazine, triazine, benzofuran, thionaphthene, indole, quinoline, benzoxazole, benzothiophene, and carbazole.

Specific compounds include
2,4-diamino-chlorobenzene
2,4-diaminothiophenol
2,4-diaminophenol
3,5-diaminobenzoic acid
methyl-2,4-diaminobenzoate
2,4-diaminoacetamide
1-(para-carbomethoxyphenoxy)-2,4-diaminobenzene
p-(2,4-diaminophenoxy) acetamilide
3-mercapto-4-amino-4-aminobiphenyl
1(2'-cyanophenyl)-2,5-diaminonaphthalene The polyimides containing the siloxane unit will contain the group of formula:

<diagram of imide structure with A and B groups> where A and B are as previously defined. The imide is formed from the corresponding half-amide:

<diagram of half-amide structure>

It is apparent that there are a number of variables available to the chemist in formulating useful polyimides. The variables include the anhydride, the siloxane and the amine.

As indicated previously, the anhydride can be diether containing:

<diagram of diether-containing dianhydride> where G has been defined, or non-diether containing:

<diagram of non-diether dianhydride> and

<diagram of dianhydride with E linkage> where E and m have been defined.

As a general proposition, the polyimide formed from a non-diether containing dianhydride and an aromatic diamine are thermoset in nature and are insoluble in organic solvents. In an attempt to work with these materials, the art has adopted several approaches. One involves preparing the poly(half-amide), which is soluble and tractable and, after the material is in place, or has been shaped or formed, heating to form the imide. The second approach has involved selection of the diamine. One researcher found that phenylindane diamines have a solubilizing effect on aromatic polyimides and that when as little as 20 mole percent of a diamine is replaced with a phenylindane diamine, a soluble polyimide is obtained. Bateman et al, U.S. Pat. No. 3,856,752.

Other researchers have used a combination of two different diisocyanates (methylene diphenyl diisocyanate and toluene diisocyanate), which because they react with anhydrides to form polyimides, are the functional equivalent of the amines. One may speculate that by reducing the symmetry of the polymer, the crystallinity is reduced and the solubility is correspondingly increased.

A third approach involves the use of diether containing anhydrides; prior art polyimides based on these anhydrides, although soluble and tractable, have deficiencies that detract from their use as films, fibers and protective coatings. Thus, they have poor adhesion to most substrates, poor elongation and poor flexibility. They display very high leakage currents on semiconductor devices and virtually no resistance to corona and other radiation; embrittlement is possible and low temperature properties are poor.

It has been found that the polyimide obtained from an anhydride, whether diether containing or not, and a siloxane as described, displays properties that are totally unexpected. The polyimide is thermoplastic and soluble; in this context, solubility refers to both variety of solvents as well as to concentration. The polyimide is soluble in chlorinated hydrocarbon solvents such as dichlorobenzene and trichlorobenzene, as well as in polar solvents such as N,N-dimethyl acetamide, N-methyl caprolactam, dimethylsulfoxide, N-methyl-2-pyrrolidone, tetramethyl urea, pyridine, dimethylsulfone, hexamethylphosphoramide, tetramethylene sulfone, formamide, N-methylformamide, butyrolactone and N-acetyl-2-pyrrolidone. Concentrations of polyimide on the order of 0.05% to about 60% by weight of solids are achievable, depending on the composition of the particular system.

In addition to being soluble, these polyimides are resistant to high energy radiation including corona discharge, U.V. and nuclear radiation (alpha-particles) and display tenacious adhesion to a variety of substrates, organic and inorganic, without the use of primers. These siloxane-containing polyimides adhere to glass, ceramic, metals, including gold, copper, stainless steel, nickel, aluminum, titanium and beryllium, and all manner of plastics, including phenolic, epoxy and polyimide (eg, Kapton ®).

One deficiency exhibited by the polyimides of the prior art is a noteable lack of adhesion. Films of polyimides containing the siloxane described herein will withstand immersion in boiling water for more than six hours; prior art polyimides lose adhesion and peel away from a substrate in less than 20 minutes.

The tenacious adhesion and resistance to thermal shock displayed by polyimides containing the siloxane unit are illustrated by a thermal cycling test whereby a polyimide coated onto a substrate is subjected to a temperature of −65° C. for two minutes followed by immediate exposure to a temperature of 150° C. for two minutes; the cycle is thereafter repeated. Polyimides containing the siloxane unit survive one hundred cycles with no loss of adhesion. Further, there is no loss of electrical properties when the substrate is a semiconductor component and the coated device is subjected to one hundred thermal cycles.

Polyimides containing the siloxane unit are far more flexible than are prior art polyimides. Thus, a siloxane-containing polyimide has an elongation on the order of 30% whereas other polyimides have an elongation of 6% to 18%. Because of the higher elongation, these polyimides can be fabricated into useful films and fibers.

Polyimides containing the siloxane unit can be processed quite readily since they have much lower Tg (second order transition temperature) than prior art materials—on the order of 140° C. as compared with 350° C. for conventional polyimides. This means that they will melt and flow more readily than prior art polyimides; the polyimides containing the siloxane unit are thus particularly useful for potting and encapsulation, as well as for transfer molding applications. The Tg of a given polyimide containing the siloxane can be increased by increasing the amount of aromatic diamine in the polyimide.

One advantage of the present siloxane unit is its remarkable heat stability. Polyimides containing bisalkylene disiloxanes are relatively heat sensitive, a factor that makes synthesis of high molecular weight polymers difficult since gelation tends to occur upon extended heating at about 200° C. One would have expected the siloxanes described herein to be equally heat sensitive, if not more so. Surprisingly, the siloxane and polymers containing this unit exhibit impressive resistance to elevated temperature. For example, a polyimide derived from bis-aminophenoxybutyl disiloxane and benzophenone tetracarboxylic dianhydride resists temperatures up to 500° C. before extensive degradation, as determined by thermogravimetric analysis.

A consequence of this temperature resistance is the ability to maintain coreactants for longer times at higher temperatures to achieve higher molecular weights than is possible with polyimides containing the bisalkylene disiloxane group.

The polyimide, and therefore the poly(half-amide), derived from an amine component and an acid or anhydride component can have part or all of the amine component replaced by the amine of formula

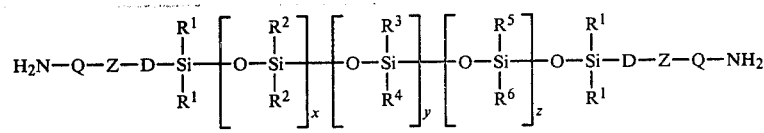

Solubility of the resulting polyimide will be affected by the nature of the dianhydride, the concentrations of the siloxane in the polymer and the value of x, y and z. For example, a diether-containing anhydride will yield a polyimide soluble over all combinations of organic diamine and siloxane. Not only is the resulting polyimide soluble in the chlorinated hydrocarbon solvents and polar solvents previously described but, where it contains a siloxane unit, the polyimide is soluble in a solvent which is derived from monoalkyl and/or dialkyl ethers of ethylene glycol and condensed polyethylene glycols and/or cyclic ethers containing no less than a 5 member ring, such as diglyme (diethylene glycol dimethyl ether) at standard temperature and pressure.

Polyimides derived from a non-diether containing anhydride and a disiloxane have limited solubility in diglyme but are more soluble in the polar solvents previously discussed such as N-methyl-2-pyrrolidone and in phenolic liquids, such as cresylic acid (methyl phenol). Solubility increases, however, when a polysiloxane is present in the polyimide. For example, the polyimide derived from benzophenone tetracarboxylic dianhydride and the bis (aminophenoxybutyl) polysiloxane where $R^2$ is methyl, x is 6 and y and z are 0 in the formula above, is soluble in warm diglyme to provide a 25% by weight solution.

When the solids content of the solution is 25% or greater at room temperature, the solubility of the polyimides in the solvent is best when the siloxane content of the polyimide is greater than 40 mole percent. The solubility of the polyimide increases considerably when the siloxane content is above 40 mole percent; as indicated one can prepare solutions wherein the polyimide has included 100 mole percent of siloxane.

At siloxane contents of less than 40 mole percent one may experience difficulty in achieving solubility at room temperature in a reasonable time for 25 percent solids solution. However, with the application of heat, solution is achieved.

When the solids content is reduced to less than about 25 percent solids, solution of the polyimides composition is more easily obtained at room temperature.

As the solids content increases above 25 percent in the solution, and the siloxane content of the polyimide is below about 40 mole percent, dissolution of the solids becomes increasingly difficult to achieve at room temperature, but is readily achieved with heating to high temperatures.

One may conclude that the silicone in the polyimide tends to solubilize the system. That is the siloxane tends to make the polyimides soluble in a greater class of solvents. The greater the siloxane content of the polyimide, the more soluble it becomes in a given solvent.

Solubility in a solvent derived from monoalkyl and/or dialkyl ethers of ethylene glycols and condensed polyethylene glycols and/or cyclic ethers containing no less than a 5 member ring such as diglyme has another advantage over the other solvents previously employed. It is now possible to prepare solutions of polyimides which can be applied to a substrate and thereafter dried to form a tough polyimide coating by solvent evaporation at temperatures significantly below those required for the polar solvents previously described. Thus, one can provide polyimide coatings by evaporating at temperatures below 150° C. and even below 100° C. For example, a polyimide obtained from 2,2-bis{4,4'-di(3,4-dicarboxyphenoxy)phenyl} propane dianhydride, m-phenylene dianiline and containing 40 mole percent of bis-aminophenoxybutyl tetramethyl disiloxane, dissolved in diglyme to provide a 25% solids solution can be applied as a coating to a substrate and dried by solvent evaporation at from about 75° C. to about 95° C. in from 20 to 30 minutes to provide a dry coating from 1 to 2 millimeters thick. The solids content can be varied according to mode of application (dipping, spraying, painting, spinning, etc.) and final use. Repeated applications can be made to obtain a desired thickness.

It has been indicated that in connection with the polysiloxanes (ie, where $R^2$ is methyl and x is large, for example, 10 to 100 or more) solubility of the polyimide is increased. However, it is possible to convert this thermoplastic (flows at 140° C.) soluble polyimide to a thermoset material by heating at about 240° C. It is believed that either methyl groups or hydrogen atoms are dislodged by the heating to generate free radicals and that crosslinking takes place via an irreversible bonding mechanism.

Further in connection with the polysiloxane containing polyimides, it has been found that tensile strength is improved when three or more diphenylsiloxane units ($R^3$ and $R^4$ are phenyl and y is 3 or more) are adjacent to one another.

The following table summarizes some of the variables and the properties of the resulting polyimide.

TABLE I

| ANHYDRIDE | | SILOXANE | | | AROMATIC | | | PROPER- |
| --- | --- | --- | --- | --- | --- | --- | --- | --- |
| | | | | Prior Art | Conventional | | FUNC- | TIES OF RE- |
| | Non | Di- | Poly- | Alkylene | Non- | Diamine[1] | TIONAL | SULTING |
| Diether | Diether | siloxane | siloxane | Disiloxane | Diether | Diether | GROUP | POLYIMIDE |
| | X | | | | X | | | A. |
| | X | | | | | X | | B. |
| | X | X | | | | | | C. |
| | X | | X | | | | | D. |
| | X | | | X | | | | E. |
| | X | X | | | X | | | F. |
| | X | | X | | X | | | G. |
| | X | X | | | | X | | H. |
| | X | | X | | | X | | I. |
| | X | X | | | | | X | J. |
| | X | | X | | | | X | K. |
| X | | | | | X | | | L. |
| X | | | | | | X | | M. |
| X | | X | | | | | | N. |
| X | | | X | | | | | O. |
| X | | | | X | | | | P. |
| X | | X | | | X | | | Q. |
| X | | X | | | | X | | R. |
| X | | | X | | X | | | S. |
| X | | X | | | | X | | T. |
| X | | X | | | | | X | U. |
| X | | | X | | | | X | V. |

TABLE I-continued

| ANHYDRIDE | | SILOXANE | | AROMATIC | | | | PROPER- |
| --- | --- | --- | --- | --- | --- | --- | --- | --- |
| | | | | Prior Art | Conventional | | FUNC- | TIES OF RE- |
| | Non | Di- | Poly- | Alkylene | Non- | Diamine[1] | TIONAL | SULTING |
| Diether | Diether | siloxane | siloxane | Disiloxane | Diether | Diether | GROUP | POLYIMIDE |
| X | | X | X | | | | | W. |

[1] or isocyanate equivalent

A. Thermoset, insoluble, fair-to-poor adhesion, elongation 6 to 18%, poor low temperature properties, difficult to incorporate fillers, not corona or radiation resistant.
B. Similar to A, but having improved solubility and flexibility.
C. Thermoplastic, soluble, good adhesion, elongation 30%, good low temperature properties, stable to corona and other radiation improvedwettability - can be filled, lower Tg than A.
D. Thermoplastic, soluble, good adhesion, superior low temperature properties, greater elongation and flexibility than C, resistant to embrittlement and fatigue, lower Tg than C, polysiloxane units allows control of properties of final product.
E. Thermoset, limited solubility, poor film, limited thermal stability.
F. High Tg, limited solubility, harder than C or D.
G. High Tg, more flexible than F, more soluble than F, harder than C or D.
H. Solubility better than F, higher Tg than C, stronger film than C.
I. Better solubility than F or H, more flexibility than F, lower Tg than H, better low temperature properties than F.
J. Vinyl, acrylyl and acetylenic functionality permits crosslinking to thermoset state.
K. Similar to J.
L. Thermoplastic, soluble, poor adhesion, poor elongation, low resistance to corona and radiation.
M. Similar to L., better flexibility, greater solubility, Tg lower than L.
N. Thermoplastic, soluble, good film, excellent adhesion, lower Tg than L, more flexible than L, good low temperature properties.
O. Thermoplastic, very soluble, superior low temperature properties, good adhesion.
P. Thermoplastic, poor film, reduced heat resistance.
Q. Thermoplastic, soluble in all proportions of amine, higher Tg than N and film harder.
R. Similar to Q but with enhanced solubility, greater flexibility and lower Tg.
S. Similar to Q but more soluble and flexible than Q, harder than R.
T. Similar to R but more flexible and lower Tg.
U. See J.
V. See J.
W. Similar to N but more flexible, lower Tg andbetter low temperature properties.

As can be seen from the foregoing, the properties of polyimide polymers containing the siloxane unit can be varied over a very broad range, at will. In addition to adjusting the reactants, one can also modify the properties of siloxane-containing polyimides by blending different polyimides. Thus, different siloxane-containing polyimides can be mixed and blended to provide desired properties. Siloxane-containing polyimides cannot easily be blended with non-silicone containing polyimides due to poor compatibility.

The reaction between amine component and anhydride is effected in a suitable solvent in the presence of a condensation catalyst. The solvent should dissolve the reactants as well as the product. Where combinations of materials will be employed, e.g. combinations of anhydride, amine or siloxane and amine, attention should be paid to the reactivity of the components. Because of different reaction rates, it is generally preferable to form a block copolymer rather than a random copolymer.

Since part or all of the amine component employed to fabricate a polyimide can be the amine-substituted siloxane unit described, the polyimide will contain from a trace of siloxane in addition to one or more other amine components to 100% siloxane and no other amine component. Thus, there can be used from 0.01 mole % to 100 mole % of bis-aminosiloxane; the majority of applications however, will call for polyimides containing from about 5 mole % to 100 mole % of siloxane and correspondingly from 95 to 0 mole % of amine components, which can comprise one or more amines.

Where the polyimide will contain 100 mole % of siloxane, the following sequence of reaction steps has been found to be effective:

(a) a reaction mixture of an anhydride and bis-(aminosiloxane) is prepared and stirred in a suitable solvent.
(b) the reaction between the two reactants produces water in a refluxing reaction.
(c) the water produced by the refluxing reaction is removed by effecting azeotropic water removal.
(d) upon complete removal of the water, the resulting polymeric solution is cooled and recovered by a suitable process such as for example, by filtering and pouring the polymeric solution into an excess amount of methanol to precipitate the product.
(e) the precipitated polymer material is separated by filtration, washed several times in fresh methanol and dried, preferably at an elevated temperature of about 60° C. to 70° C., under vacuum to effect volatization of the methanol and any adhering solvent.

Where the polyimide will contain an amine component in addition to the siloxane, the following procedure is effective:

(a) the anhydride component is first reacted with the major of the siloxane and amine component materials in a suitable solvent. This major component may be either an organic amine or a bis(aminosiloxane).
(b) the reaction between the anhydride material and the major component material is effective at reflux, and water is produced.
(c) the water produced by the refluxing mixture is removed by effecting azeotropic water removal.
(d) upon completion of the reaction and after removing all the water produced by the refluxing reaction, the mixture is cooled, generally to room temperature or slightly above.
(e) the third component material, either an organic amine or a bis(aminosiloxane), is then added to the mixture and the mixture heated to an elevated temperature for a sufficient time to produce a polymeric solution of the polyimide.
(f) upon completion of the last reaction, the resulting polyimide material is recovered by a suitable process such as, for example, filtration and precipitation of the polyimide in an excess amount of methanol.
(g) the precipitated polymer is separated by filtration, washed several times in fresh methanol and dried, preferably at an elevated temperature of about 60°

C. to 70° C., under vacuum to effect volatization of the methanol and any adhering solvent.

Where the desired product is a poly(half-amide), the amine components, including the siloxane, are combined and cooled to 0° C. The anhydride component is thereafter added gradually, over an extended period of time. The poly(half-amide) forms readily without the application of heat and without catalysts.

Because of the surprising heat stability possessed by the siloxanes described herein and the reduced Tg, the polyimides can also be prepared by hot melt polymerization, in the absence of solvents. The materials are simply combined in equimolar amounts, mixed and heated. One method involves combining the materials in an extruder heated to about 300° C. and extruding, on a continuous basis, the polyimide product.

As indicated, polyimides containing the siloxane unit are particularly suitable for use as wire enamels, as conformal, protective, junction and passivation coatings for electrical devices, printed circuit boards and semiconductor devices. They are suitable for use with electric devices since they have several desirable physical characteristics. The polyimide is one which can easily be applied and dried or cured in place. The polyimide will not degrade, and enhances the electrical characteristics of the device to which it is applied. It adheres very tenaciously to the surface to which it is applied to prevent migration of ions on the surface of the device, particularly when employed with semiconductor devices, and does not release any materials during drying or curing cycles which are deleterious to the operating characteristics of the device. The polyimide is impermeable to moisture and exhibits good abrasion resistance to protect the surfaces to which the coating is applied.

The polyimide is also capable of being applied in multiple layers to provide a thick coating when required. The polyimide is able to bond well to itself. Should the electronic device be employed in circuitry where corona is a problem, the material exhibits good corona resistance when cured.

When a polyimide is not capable of inherently exhibiting all of the desired characteristics to the degree necessary, it is capable of being modified to achieve the desired end result. Often times stray alkali and heavy metal ions cause undesirable degradation of electrical properties of semiconductor devices. Therefore, the polyimide can be modified with chelating materials admixed therewith or chemically bonded thereto. Ease of application to the surface to be protected and reasonably short curing or drying times are still retained. This is of particular interest when the coating material is employed in the manufacture of mass produced electronic devices.

The polyimide is translucent. Such a material, when retaining the other desirable characteristics, is useful to fabricate photovoltaic devices. Particularly, it is desirable to bond a light emitting diode to the surface of another semiconductor device to turn the device "on" and "off" in response to the operation of the light emitting diode. The copolymer material of this invention is also applicable for use in bonding protective covers to exposed surfaces of photovoltaic devices such as solar cells.

The dielectric strength of the polyimide may be further enhanced by admixing suitable filler materials therein. Preferably, an electrically insulating material having a dielectric constant which is approximately the same as the polyimide is admixed therein. The filler material is uniformly distributed throughout the polyimide coating as applied to a substrate. Other materials suitable as a filler material are those materials known to have a relatively good ability to resist electrical conduction although their dielectric constant is higher than that of the polyimide. Suitable electrically insulating filler materials have been found to include aluminum oxide, silicon oxide, glass fibers, boron nitride, quartz, mica, magnesium oxide, activated polytetrafluoroethylene and the like in a finely divided, or pulverized form.

Whether a filled or unfilled polyimide is employed, the electrical properties of a given device are enhanced. The polyimide has an inherent elasticity to withstand repeated cycling from dipping in liquid gases in temperature ranges of approximately—100° C. to heating in a furnace at approximately 300° C. and back into a liquid gas for a temperature excursion range of about 400° C. or more. Additionally, it has been found that the polyimides withstand short temperature excursions up to about 400° C. to 500° C. without degradation of their electrical characteristics.

The polyimide can be applied over electrically insulating layers of silicon oxide, silicon nitride, aluminum nitride and the like; it can also be applied as an insulating layer in place of those materials.

The properties of polyimides containing the siloxane unit make them useful for two other semiconductor application areas. One relates to the die bonding and wire bonding aspects wherein the finished chip is attached to the package, leads connected and the package sealed to form a semiconductor device ready for sale and use. Because of their superior adhesion and temperature resistance, the polyimides containing the siloxane unit are useful in preform bonding, whereby the polyimide is is applied to the die-attach area of a package and the solvent evaporated.

The chip or die is thereafter placed on the die-attach area of the package and, with moderate heating, the chip is firmly adhered to the package. The polyimide can be filled with a conductive material, such as silver particles to provide a conductive bond.

Following die bonding is the wire bonding step wherein the chip is connected to the package leads by fine wires of gold or aluminum. The interior of the package can then be filled with a flexible polyimide and the package covered and sealed. The flexible polyimide, either because of its flexibility or because of its thermal expansion properties, or both, results in a packaged device able to withstand thermal cycling without breaking the fine wires inside the package; other polyimides tend to break the fine wires upon thermal cycling.

Another semiconductor application involves the use of a siloxane-containing polyimide as a passivation coating on a semiconductor device. This is the final outer coating on a device which, at present, is frequently glass.

A thermoplastic polyimide, being substantially inert, temperature resistant and yet capable of flowing upon heating and having superior dielectric properties, finds application as a passivation coating. Following application of the polyimide to the device, holes can be made in the polyimide, wires attached to the device and the device heated; the polyimide will flow to fill the voids around the wires, thus providing a self-leveling passivation coating.

In an alternative mode of providing a polyimide passivation coating on a semiconductor device, one can apply by spin coating, a layer of poly(half-amide) to a device and thereafter heat the coated device to evaporate the solvent and partially advance the cure.

A microelectronic photoresist is then applied over the poly(half-amide) and exposed to light through a mask. Following the developing step, the exposed poly(half-amide) can be dissolved away. Wires can be attached to the device and the device heated; the poly(-half-amide) will flow to fill the avoids around the wires and will cure to provide a water impermeable, scratch-resistant, continuous passivation coating for the semiconductor device.

Because of their adhesive and dielectric properties, the polyimides containing the siloxane unit can be used to combine two or more layers of chips to provide multilayer semiconductor devices.

The thermoplastic polyimides containing the siloxane unit are processible by compression molding, film casting and solution fiber spinning techniques. Because of their high elongation and toughness, they are particularly useful in thin-film products—films, enamels, adhesives, coatings and fibers. They can be molded and parts molded from these polyimides retain high strength at 300° C. and as high as 500° C. for short periods, for example, during processing of graphite and glass-fiber laminates and hot-draining of fibers. Laminates, films and coatings display a minimum of voids or imperfections because no reaction products are formed at processing temperatures. The thermoplastic polyimides containing the siloxane unit have the following general properties. They are molded simply be exceeding the glass transition temperature for sufficient time with application of pressure for good flow; their elongation imparts good machinability with low brittleness; the polyimides require no post-cure to develop full high-temperature properties; they can be reclaimed and used as required, and defective laminates can often be corrected by reflowing; they can be cast into film from solution using conventional casting machines, the films being useful in both supported and unsupported applications; the films adhere well by heat-sealing to themselves as well as to other polyimides; they are solution-spun into fibers to produce flame resistant, high temperature resistant fabrics; they are molded with various fillers into parts having high strength at high service temperatures and flame resistance; unfilled molded parts have low coefficients of thermal expansion while glass-graphite and asbestos-filled parts give still lower coefficients of thermal expansion; they provide parts that wear well with low friction and molding compounds filled with graphite powder, molybdenum or tungsten disulfide or PTFE produce parts with self-lubricating wear surfaces such as piston rings, valve seats, bearings, seals and thrust washers.

Laminates are made in high-pressure platen presses, low-pressure vacuum bags or moderate pressure vacuum autoclave bags. Solutions can be used as laminating varnish to impregnate glass, graphite or quartz cloth, or glass, boron, graphite or aramid fibers to produce laminates with flame-resistance, high-temperature strength and good electrical properties having utility in radomes, printed circuit boards, radioactive waste containers and turbine blades and structural parts close to the hot engine environment.

Polyimide film has good mechanical properties through a range from liquid helium temperature to 1100° F. It has high tensile and impact strength and high resistance to tear initiation. Room temperature properties are comparable to those of polyester film while at −453° F., the film can be bent around a ¼ inch mandrel without breaking and at 932° F. it has a tensile strength on the order of 3500–4000 PSI.

The foregoing discussion of polyimides has dealt with the incorporation of a polysiloxane unit into a polyimide by means of a bis(amino)polysiloxane; it will be apparent, however, that the polysiloxane unit can be incorporated, with the same effect, into a polyimide via the polysiloxane dianhydride.

There should also be mentioned the polyesterimides, containing both imide and ester linkages. In one illustration, trimellitic anhydride is reacted with hydroquinone diacetate to yield a dianhydride of formula:

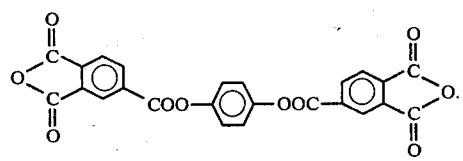

This dianhydride is reacted with a diamine to provide a polyesterimide. Alternatively, one can react a diamine, such as m-phenylene diamine with trimellitic anhydride to an imide of formula:

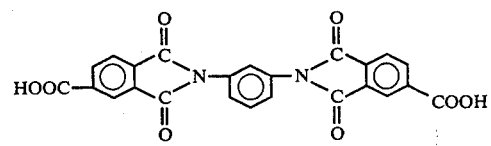

This imide can be further reacted with hydroxyl-functional materials, such as hydroxyl-terminated polyesters having a branched structure to allow crosslinking.

The siloxane unit can readily be incorporated into these polyesterimides by appropriate selection of functional group F.

2. Poly(Amide-Imide)

Poly(amide-imide) is the reaction product of an organic diamine with a tricarboxylic acid anhydride:

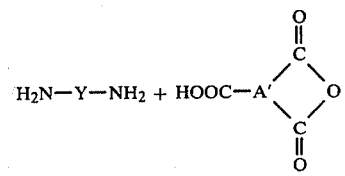

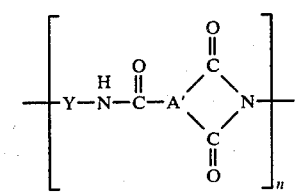

The diamine component can be selected from the same groups as previously described in connection with the polyimides.

In the tricarboxylic acid anhydride, $A^1$ is a trivalent organic radical, obtained from such compounds as:

trimellitic anhydride; 2,6,7-naphthalene tricarboxylic anhydride; 3,3',4-diphenyl tricarboxylic anhydride; 3,3',4-benzophenone tricarboxylic anhydride; 1,3,4-cyclopentane tetracarboxylic anhydride; 2,2'3-diphenyl tricarboxylic anhydride; diphenyl sulfone-3,3'4-tricarboxylic anhydride; diphenyl isopropylidene-3,3',4-tricarboxylic anhydride; 3,4,10-propylene tricarboxylic anhydride, 3,4-dicarboxyphenyl-3-carboxyphenyl ether anhydride; ethylene tricarboxylic anhydride; 1,2,5-naphthalene tricarboxylic anhydride, etc. Also useful are the corresponding acids of such anhydrides.

There can also be used the triacid anhydride analogues of the diether-containing anhydrides described above in connection with the polyimides.

Part or all of the amine component can be replaced by a bis(amino-siloxane); part or all of the anhydride component can be replaced by a siloxane-containing triacid anhydride. Thus, there is provided a poly(amide-imide) containing a siloxane unit of formula

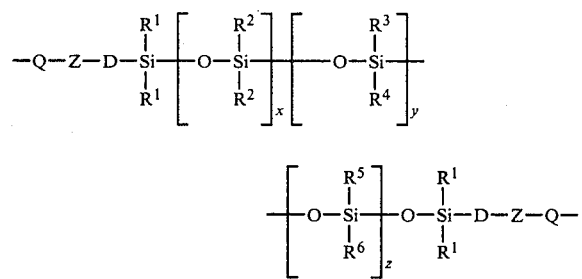

where the various elements have previously been described.

As in the case with the polyimides, the reaction proceeds stepwise, with the formation of the amide taking place by simply combining and mixing the amine component with the triacid anhydride component. The imide is formed by heating at temperatures on the order of 180° C. to 200° C. to effect cyclization.

Poly(amide-imides) containing the siloxane unit display excellent high temperature performance, being serviceable at temperatures from cryogenic to 500° F. and capable of withstanding cycling; they have high tensile, flexural, impact and compressive strengths, superior elongation and good resistance to creep. Further, they display low coefficient of thermal expansion, flame retardance, resistance to nuclear and UV radiation and good electrical characteristics. Chemical resistance and moisture absorption are improved by the presence of the siloxane units; the flow properties of molding compositions are improved by the siloxane unit, it being possible to use lower mold temperatures and pressure than are necessary to process poly(amide-imides) that do not contain the siloxane unit.

Poly(amide-imides) containing the siloxane unit have a variety of uses. Because of their high temperature resistance and corona resistance, they are suitable as insulation for electrical conductors. Solutions of the polyamide or the poly(amide-imide) can be applied to electrical conductors such as copper wire, aluminum, etc., and thereafter heated to evaporate the solvent and/or to complete the imidization. Thus, motor and generator wire coatings can be formed having good electrical properties, heat resistance and flexibility. Films and fibers can be extruded or can be cast from solutions of either the poly(amide-imide) or the poly (amide). Solvents which can be employed are, for example, N,N-dimethylformamide, N,N-dimethylacetamide, N,N-diethylformamide, N,N-diethylacetamide, N,N-dimethylmethoxyacetamide, dimethylsulfoxide, N-methyl-2-pyrrolidone, pyridine, dimethylsulfone, hexamethylphosphoramide, tetramethylenesulfone, phenol, phenolwater mixtures, and dimethyltetramethylenesulfone. Mixtures of these solvents with other inert organic solvents such as benzene, benzonitrile, dioxane, betaethoxyethylacetate, butyrolactone, xylene, toluene and cyclohexane, can also be employed.

Since part or all of the amine component employed to fabricate a poly(amide-imide) can be the amine substituted siloxane unit described, the poly(amide-imide) will contain from a trace of siloxane in addition to one or more other amine components to 100% siloxane and no other amine components. Thus, there can be used from 0.01 mole % to 100 mole % of bis(aminosiloxane); the majority of applications, however, will be satisfied by poly(amide-imides) containing from about 5 mole % to 100 mole % of siloxane and correspondingly from 95 mole % to 0 mole % of amine component, which can comprise one or more amines. The corresponding relationships apply when the siloxane unit is provided in the form of an acid or anhydride.

3. Polycarbonate

Polycarbonate resin is a polymeric carbonate ester produced by the phosgenation of an organic dihydroxy compound. Commercial polycarbonate resin is produced by the reaction of phosgene with bisphenol A:

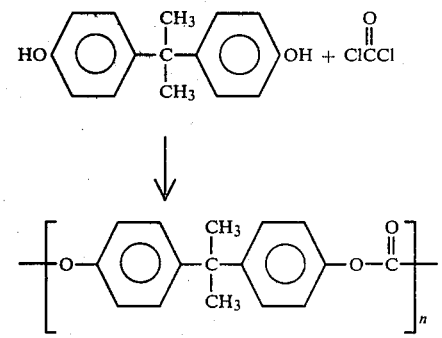

where n is from about 50 to about 400.

Although a versatile and widely use material, polycarbonate has certain drawbacks, such as poor resistance to chlorinated hydrocarbons and certain other solvents; a hygroscopic tendency; notch sensitivity, susceptibility to loop stresses; stress cracking accelerated by contact with oil or gasoline and a critical thickness limitation. In Izod impact tests with ⅛" bars, values of 12–16 ft. lbs. per notched inch are attained. However, the polycarbonate mode of failure changes at about 0.2 inch thickness from high evergy-absorbing ductile fracture to low energy-absorbing brittle fracture with an attendant sharp drop in impact resistance above 0.2 inches in thickness. 0.2 inch thickness from high energy-absorbing ductile fracture to low energy-absorbing brittle fracture with an attendant sharp drop in impact resistance above 0.2 inches in thickness.

The properties of polycarbonate resins can be improved by the incorporation therein of a siloxane unit of formula

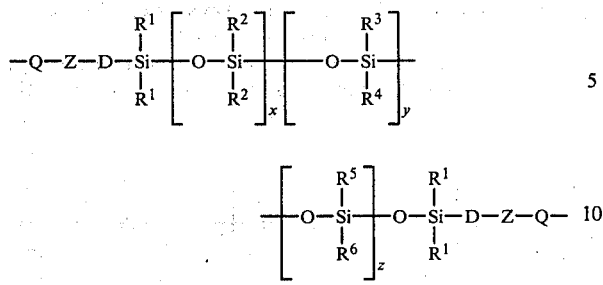

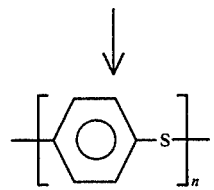

where the various elements are as previously described. More particularly, there can be incorporated from 0.01 to 30 mole % of the siloxane, initially present in the form of the bisphenolic, or other phosgene-reactive derivative. In general, there will be present from 0.1 mole % to 15 mole % of the siloxane, and at these levels there is seen improvement in the various properties; impact resistance of thick sections improves, as does resistance to hydrocarbon and other solvents. Low temperature properties increase and there is seen a decreased tendency to yellow upon exposure to UV radiation.

Thus, in one embodiment, there is provided the reaction product of phosgene and a siloxane of formula

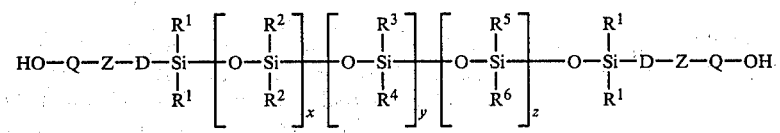

and in another embodiment there is provided the reaction product of phosgene, bisphenol A and the bisphenolicsiloxane described above.

The reaction takes place readily under standard conditions for phosgenation of bisphenol A; the phenolic substituted siloxane reacts at about the same rate as the bisphenol A.

The siloxane-containing polycarbonate is readily processed by all standard thermoplastic methods, including injection molding, extrusion and blow molding. Sheets can be thermoformed using vacuum, pressure or drape heating methods. It can be solvent and adhesive bonded, painted, printed, hot-stamped, welded ultrasonically and heat staked.

4. Polyphenylene Sulfide

Polyphenylene sulfide is a crystalline, aromatic polymer prepared by the reaction of dichlorobenzene with sodium sulfide in a polar solvent.

The properties of polyphenylene sulfide resins can be improved by the incorporation therein of a siloxane unit of formula

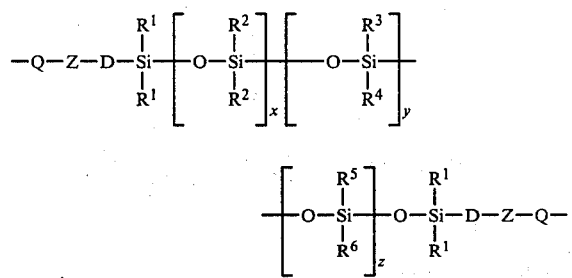

where the various elements are as previously defined. There can be incorporated from 0.01 mole % to 30 mole % of the siloxane unit, initially present in the form of the dihalide or other reactive derivative. In general, there can be present from 0.1 mole % to 15 mole % of the siloxane and at these levels there is seen improvement in the various properties. Thus, there is obtained a siloxane modified polyphenylene sulfide having good solvent and chemical resistance, low coefficient of friction, ease of molding, high temperature resistance, flame retardance and good electrical properties. The polymer has improved flexibility and superior tensile strength.

In one embodiment, there is contemplated the reaction product of sodium sulfide with a siloxane of formula

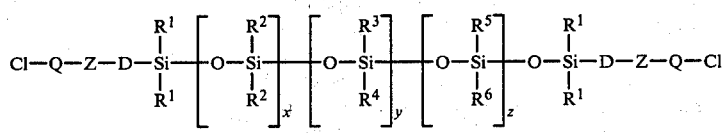

and in another embodiment there is contemplated the reaction product of dichlorobenzene, sodium sulfide and a dichlorosiloxane as described above.

The reaction proceeds readily in a dipolar, aprotic solvent and the reaction rates between dichlorosiloxane and dichlorobenzene and sodium sulfide are similar.

The resulting polymer is readily injection molded to provide parts that are dimensionally stable and heat resistant.

5. Sulfone Polymers

Polysulfone is produced from a bisphenolic compound, such as bisphenol A, and dichlorodiphenylsulfone:

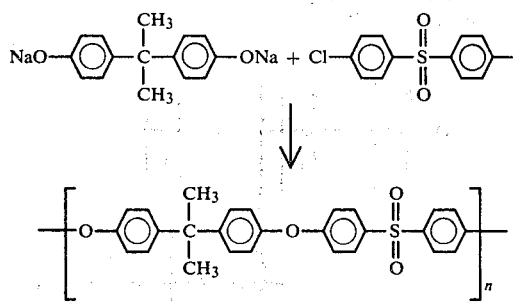

where n is 50 to 80.

The properties of polysulfone polymers can be improved by the incorporation therein of a siloxane unit of formula

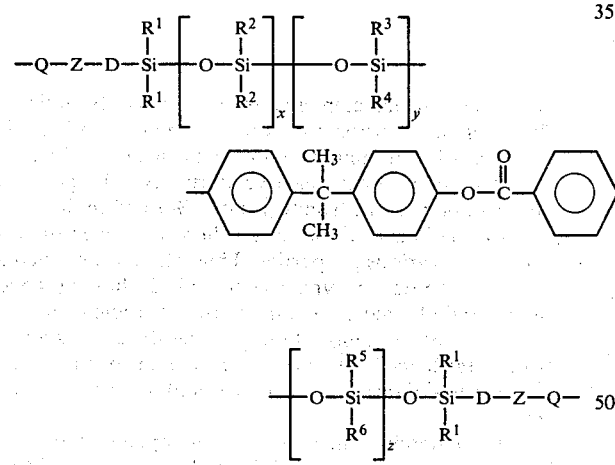

where the various elements are as previously described. There can be incorporated from 0.01 mole % to about 30 mole % of the siloxane unit, initially present as the alkali metal salt of the dihydroxide. In general, there can be present from 0.1 mole % to 15 mole % of the siloxane and at these levels there is seen an improvement in the various properties. Thus, there is obtained a siloxane-modified polysulfone polymer having improved solvent resistance, high thermal and oxidative resistance, high resistance to hydrolysis and inorganic chemicals and improved electrical properties. They have low flammability and smoke emission and have improved flexibility and toughness. The siloxane unit reduces the Tg and so polysulfone polymers containing this unit display lower melt viscosity and correspondingly better moldability. Parts can be molded to extremely close tolerances and display very low creep. The coefficient of friction is reduced.

In one embodiment, there is contemplated the reaction product of a dichlorodiphenylsulfone with a siloxane of formula

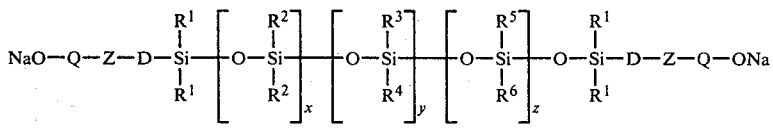

and in another embodiment there is contemplated the reaction product of dichlorodiphenylsulfone, the alkali metal salt of a bisphenolic compound and an alkali metal phenoxide derivative of a polysiloxane, as described above.

The reaction proceeds readily in a dipolar, aprotic solvent such as dimethylsulfoxide and the reaction rates between the bisphenol and the siloxane are similar.

The resulting polymer is readily injection molded to provide parts that are dimensionally stable and resitant to temperatures of 300° to 400° F. They can be thermoformed, cast into films from solution, blow-molded and extruded into sheet, pipe and other products. The polymer can also be formed into a membrane and used in reverse osmosis water purification.

6. Aromatic Polyester (Polyarylate)

Polyarylate polymers are aromatic polyesters of aryl dicarboxylic acids and bisphenols. The acids include isophthalic, terephthatic and mixtures thereof. The bisphenols are illustrated by p,p'-biphenol and bisphenol A. The polymer can be modified by p-hydroxybenzoic acid.

The reaction product of bisphenol A with terephthalic and isophthalic acids is illustrated by

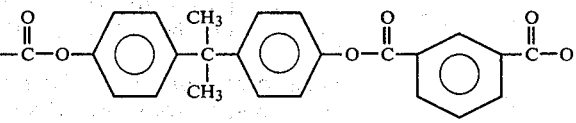

while the reaction product of p,p'-biphenol, p-hydroxybenzoic acid and terephthalic acid is illustrated by

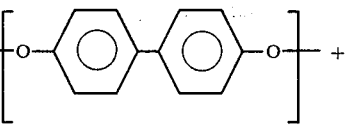

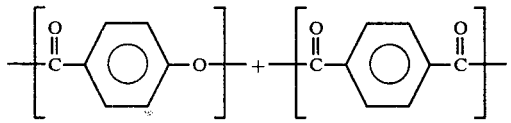

The properties of polyarylate polymers can be improved by the incorporation therein of a siloxane unit of formula

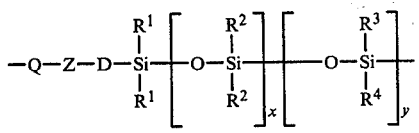

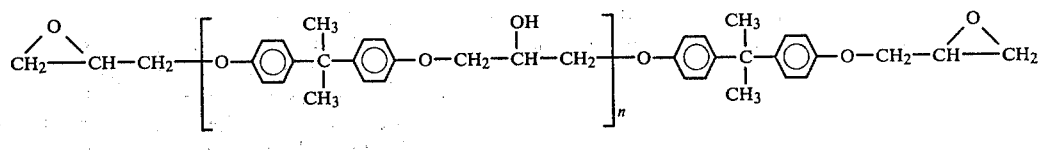

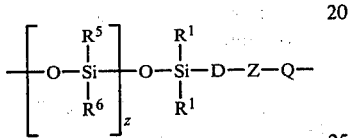

where the various elements are as previously described.

There can be incorporated from 0.01 to about 30 mole % of the siloxane unit, initially present as either the dihydroxide or the diacid. In general, there can be present from 0.1 mole % to 15 mole % of the siloxane and at these levels there is seen an improvement in the various properties. Thus, there is obtained a siloxane-modified polyarylate polymer having improved resistance to stress-cracking by organic solvents, to hydrolysis and having lower Tg resulting in lower melt viscosity and therefore, better molding properties. Further these polymers have better flexibility and toughness.

The matter of melt viscosity is a significant improvement. Previously, quantities of crystalline thermoplastics such as polyethylene had been used to improve flow during molding.

The polymers have high modules, flexural recovery, improved UV stability, and improved electrical properties. They can be molded or extruded.

In one embodiment, there is contemplated the reaction product of an aromatic diacid with a dihydroxysiloxane as described. In another embodiment, there is contemplated the reaction product of a bisphenolic compound with a bis(dicarboxysiloxane) as described.

7. Epoxy Polymers

An epoxy resin is any molecule containing more than one alpha-oxirane group capable of being converted to a useful thermoset form. The general term "epoxy resin" is applied to both the uncured, thermoplastic and cured, thermoset states.

The most widely used resins are diglycidyl ethers of bisphenol A, which are made by reacting epichlorohydrin with bisphenol A in the presence of an alkaline catalyst. These materials are illustrated by the following formula:

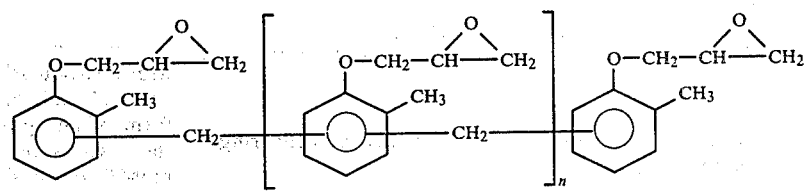

By controlling the operating conditions and varying the ratio of epichlorohydrin to bisphenol A, products of different molecular weight can be made. For liquid resins, n in the above formula is generally less than 1; for solid resins it is generally 2 or more.

Another class of epoxy resins is the novolacs, particularly the epoxy phenol and epoxy cresol novolacs; an epoxy cresol novolac is illustrated by the formula The resins are produced by reacting a phenol-formaldehyde or cresol-formaldehyde reaction product with epichlorohydrin.

Another class of epoxy resins is denoted by the cycloaliphatic epoxy resins; these are produced by the peracetic epoxidation of cyclic olefins and by the condensation of an acid, such as tetrahydrophthalic acid, with epichlorohydrin, followed by dehydrohalogenation:

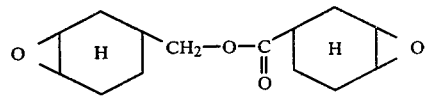

Another group of epoxy resins comprises the specialty polyfunctional epoxy resins, which are used in conjunction with graphite and glass fiber in composite materials and structural adhesives in the aerospace industry. These include epoxy derivatives of polynuclear phenols, prepared by reaction of glyoxal with phenol in the presence of HCl:

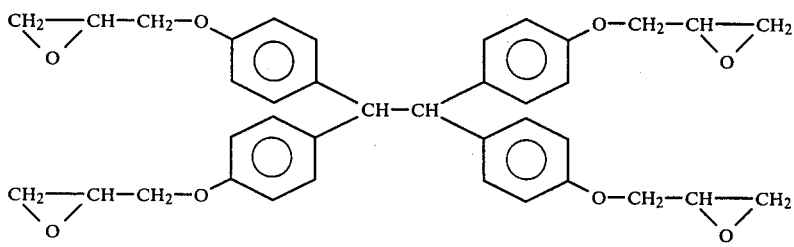

triglycidyl derivatives of p-aminophenol, produced by the reaction of epichlorohydrin with phenolic and amino groups followed by dehydrohalogenation

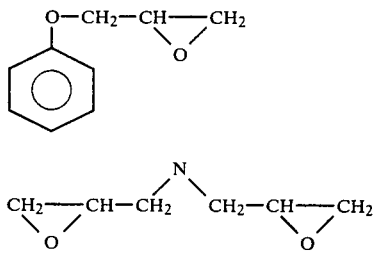

and the tetraglycidyl derivative of 4,4-methylenediamiline

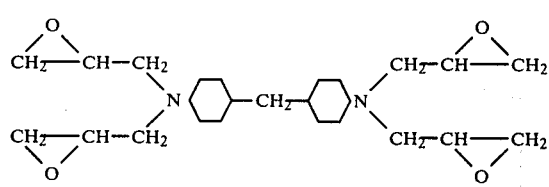

Other epoxy resins are based on heterocyclic ring structures, such as hydantoin

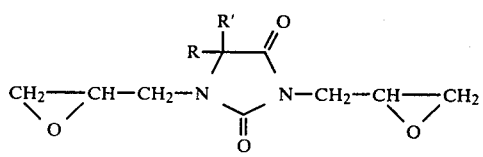

while others are based on hydrogenated bisphenol A.

Epoxy resins must be cured with crosslinking agents or catalysts to develop desirable properties; the epoxy and hydroxyl groups are the reaction sites through which crosslinking occurs. Crosslinking agents include amines, anhydrides, acids, aldehyde condensation products and Lewis Acid catalysts. The curing mechanisms have been studied extensively and are described in Handbook of Epoxy Resins, by Lee and Neville, Copyright 1967 by McGraw Hill, Inc.

Epoxy resins are versatile and widely used materials; nevertheless they have certain drawbacks, such as poor flexibility, low thermal cycling and thermal shock resistance and poor weatherability.

The properties of epoxy resins can be improved by the incorporation therein of a siloxane unit of formula $$-Q-Z-D-\underset{\underset{R^1}{|}}{\overset{\overset{R^1}{|}}{Si}}\left[-O-\underset{\underset{R^2}{|}}{\overset{\overset{R^2}{|}}{Si}}\right]_x\left[-O-\underset{\underset{R^4}{|}}{\overset{\overset{R^3}{|}}{Si}}\right]_y$$

$$\left[-O-\underset{\underset{R^6}{|}}{\overset{\overset{R^5}{|}}{Si}}\right]_z -O-\underset{\underset{R^1}{|}}{\overset{\overset{R^1}{|}}{Si}}-D-Z-Q-$$

where the various elements are as previously described. More particularly, there can be incorporated from 1 to about 50 mole % of the siloxane, initially present in the form of an epoxide, amine or anhydride. In general, there will be present from about 10 mole % to about 40 mole % of the siloxane, and at these levels there is seen improvement in various properties; flexibility is improved without sacrificing other properties. Low temperature properties are enhanced, as is weatherability and resistance to various kinds of radiation.

Thus, in one embodiment, the epoxy component of an epoxy resin is replaced, in whole or in part, by a bis (epoxy) siloxane of formula

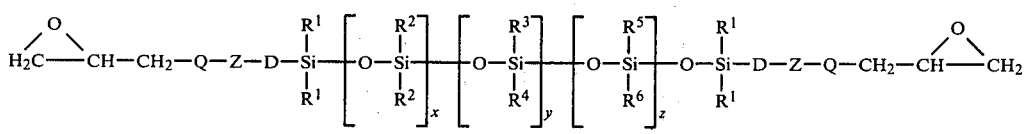

In another embodiment the amine component in a curable epoxy composition is partially or totally replaced by a bis (amino) siloxane of formula

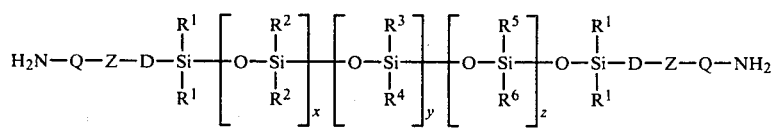

and there is thus provided a curable composition comprising an epoxy resin and a bis (amino) siloxane.

As indicated previously, epoxy resins can also be cured via an anhydride and it is now possible to introduce the siloxane unit by means of a dianhydride derivative thereof. Thus there is provided a curable epoxy composition comprising an epoxy resin and a bis (dianhydro) siloxane. The dianhydride groups can be attached directly

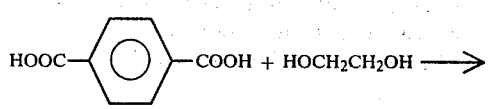

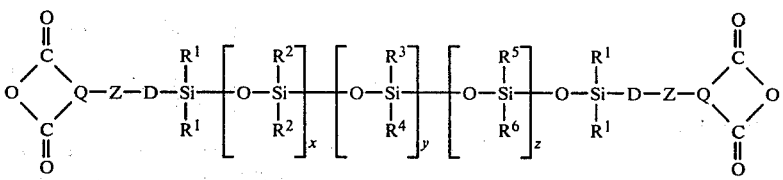

and more particularly:

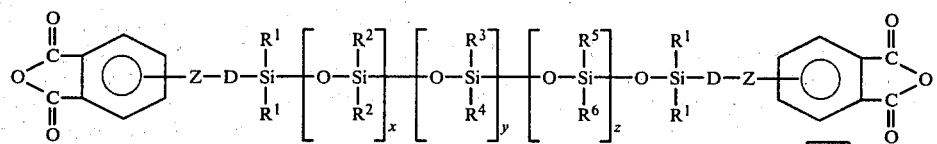

or the dianhydride can be bonded via an intermediate group

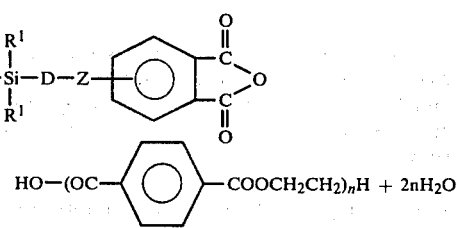

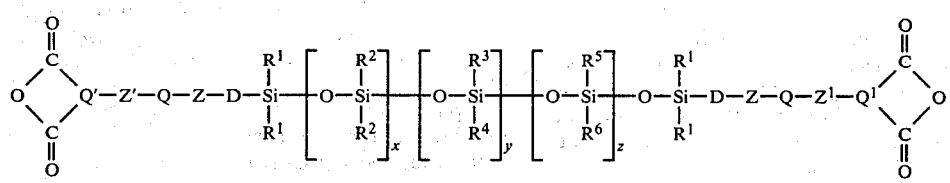

Where Q' and Z' are selected from the same group as are Q and Z.

Q' can conviently be an aryl group:

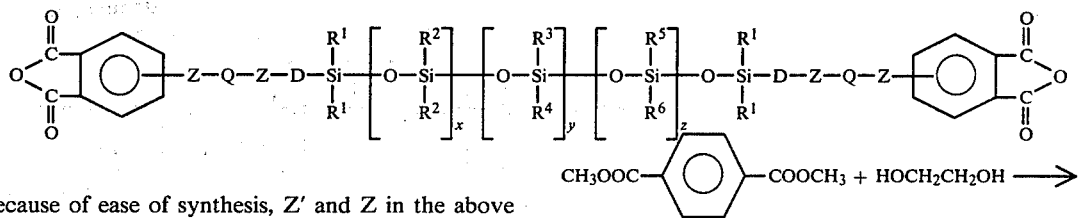

Because of ease of synthesis, Z' and Z in the above formula are preferably oxygen and Q is a phenylene group.

It is thus seen that the siloxane unit can be incorporated into an epoxy resin in a variety of ways; the resulting cured epoxy resins are more flexible than before. It is also apparent that the flexibility of epoxy resins can be adjusted to approach that of elastomeric compositions.

8. Polyester Polymers

Polyester polymers are produced by the reaction of an acid with an alcohol. Thermoplastic polyesters such as polyethylene terephthalate and polybutylene terephthalate are produced by the polyesterification reaction between a single glycol and a single dibasic acid. The term "copolyester" has been applied to polyester polymers fabricated from more than one glycol and/or more than one dibasic acid.

Thus, polyethylene terephthalate is prepared from terephthalic acid or its functional equivalent, dimethyl terephthalate

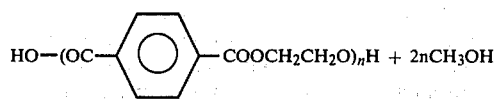

The polymerization is usually conducted by melt condensation polymerization at elevated temperature, above 270° C., and vacuum.

Polyethylene terephthalate has many attractive properties, including clarity and toughness when amorphous, adequate solvent resistance and relative impermeability to water vapor, oxygen and $CO_2$. The polymer is, however, characterized by certain disadvantages, such as deterioration of mechanical characteristics at room temperature due to progressive crystallization, as evidenced by the notched Izod impact strength test. The polymer has a lack of toughness when crystallized and moldings tend to stick to molds and have poor surface appearance.

Polybutylene terephthalate is made by a condensation polymerization polymerization reaction between dimethyl terephthalate and 1,4-butamediol

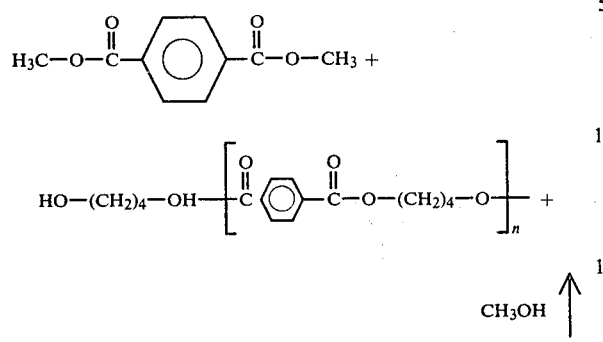

The reaction is conducted in two steps. In the first, excess diol is employed to ensure removal of methanol and to produce a prepolymer mixture. In the second step the molecular weight is increased by a re-equilibrium with removal of the excess diol.

The polymer, while useful, is attended by certain shortcomings, including low fracture resistance and high notch sensitivity, as well as limited resistance to hydrolysis.

Other polyesters include polymers where cyclohexanedimethanol is used as part or all of the diol. These polymers require processing temperatures on the order of 500° F. and tend to have high melt viscosity. Further, they have poor resistance to hydrocarbon and Ketone solvents and poor U.V.-resistance.

In addition to the thermoplastic polyester polymers, there are the unsaturated polyester polymers which contain unsaturated sites for crosslinking to form thermoset materials. The components of these compositions are a linear polyester resin, a crosslinking monomer and an inhibitor to provide shelf stability.

The linear polyester is typically the condensation product of an ethylenically unsaturated dibasic acid, a dibasic acid not containing ethylenic unsaturation and a saturated polyol. Representative unsaturated intermediates include maleic anhydride and fumaric acid; "saturated" acids include phthalic anhydride, isophthalic acid and adipic acid; the glycols include propylene glycol, ethylene glycol, diethylene glycol and dipropylene glycol. Usual crosslinking monomers include styrene, vinyl toluene, methyl methacrylate, alpha-methyl styrene, and diallyl phthalate. Conventional inhibitors are hydroquinone, quinone and t-butyl catechol.

Crosslinking takes place by a free-radical initiated polymerization reaction and the usual free-radical source is a peroxide catalyst, such as methyl ethyl Ketone peroxide, cyclohexanone peroxide, benzoyl peroxide and cumene hydroperoxide.

The properties of polyester polymers can be improved by the incorporation therein of a siloxane unit of formula

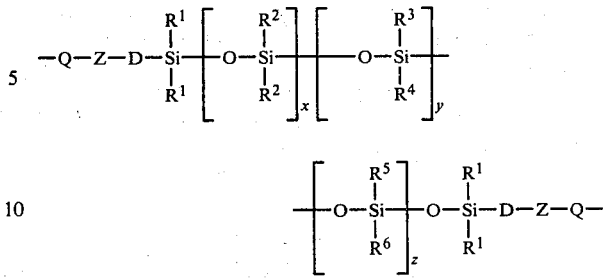

where the various substituents are as previously described. More particularly, part or all of the acid component of a polyester polymer can be replaced by an acid- or anhydride-functional siloxane. Thus, there can be incorporated from 0.01 mole % to 100 mole % of the acid component, of the siloxane unit, initially present as the acid, anhydride or other reactive derivative. In general, there can be present from 0.1 to 65 mole % of the siloxane and at these levels there is seen improvement in the various properties. Thus, there is provided a modified thermoplastic polyester having improved solvent and chemical resistance, lower coefficient of friction and greater ease of molding including lower Tg and reduced tendency to adhere to the mold. The materials also have improved hydrolytic resistance and improved radiation resistance, including U.V. Further, the toughness of the polymer is enhanced and the tendency of the polymers to crystallize at room temperature and lose physical properties is reduced. In addition, there is provided a thermoset polyester composition having better toughness, greatly enhanced electrical properties and stability at elevated temperatures.

In one embodiment, there is contemplated the reaction product of an acid- or anhydride-functional siloxane with a polyol. Thus, there can be reacted with a polyol, a compound of formula

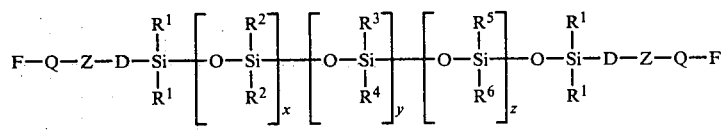

where F is COOH, dicarboxylic acid anhydride or the group $F_3$—Q'—Z'— where Z' is selected from the same group as Z, Q' is selected from the same group as Q, and $F_3$ is COOH or dicarbocylic acid anhydride.

As indicated previously, the preferred embodiments, because of ease of synthesis, are those where Q and Q' are phenylene and Z and Z' are oxygen:

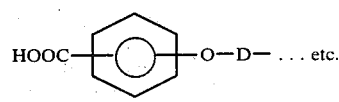

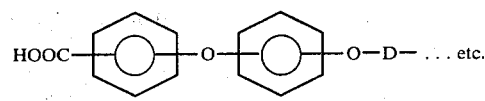

-continued

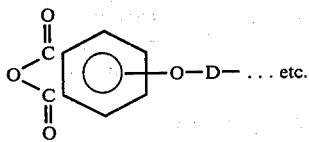

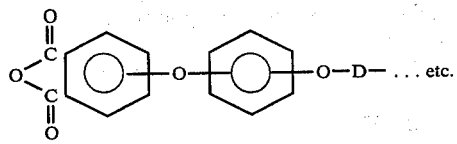

It is noted that for crosslinking applications appropriate functionality can be incorporated into the siloxane unit, either on the phenylene group or on the silicone atom, as has been previously described.

9. Polyurethane Polymers

The siloxane unit can be incorporated into urethane compositions to enhance the oil and water repellent properties with improved temperature resistance, to provide improved low temperature properties, improved electrical properties and, at higher siloxane content, mold release and other characteristics associated with low free surface energy.

The basic chemistry of the polyurethanes involves the addition polymerization reaction of a polyisocyanate with a polyfunctional hydrogen donor, and it has been found that this basic chemistry will accomodate the incorporation of a polysiloxane unit into a polyurethane polymer.

While the term "polyurethane polymer" generally refers to compositions which contain the characteristic urethane group,

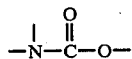

obtained by reacting a polyisocyanate with a polyol, polyurethane compositions can also contain urea groups

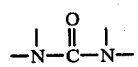

obtained by reacting a polyisocyanate with an amine, and can contain amide groups

obtained by reacting a polyisocyanate with an acid.

In one aspect, the properties of polyurethane polymers can be improved by incorporating therein the polysiloxane unit of formula

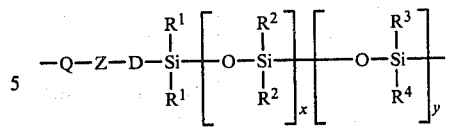

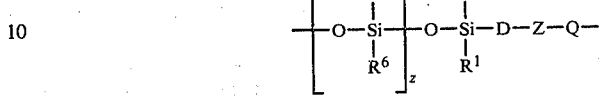

where the various elements have been previously described, and the preferred embodiments are also as previously described. The polyurethane can contain from about 0.5% to 50% by weight of the polysiloxane, initially present as an amine-functional, hydroxy-functional, carboxylic acid-functional or isocyanate-functional compound.

Thus, the polysiloxane unit can be obtained from a compound of formula

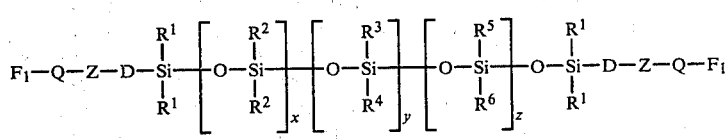

where $F_1$ is amino, hydroxyl, isocyanato or carboxylic acid to provide a polysiloxane-modified polyurethane composition. $F_1$ can be connected to Q directly, or via an intermediate organic radical.

The polysiloxane unit can be incorporated into a polyurethane polymer in a variety of ways; there can be used the functionally substituted siloxanes where the functionality is isocyanate, amino, hydroxyl or carboxylic acid to make a wide variety of polyurethane intermediates and end products, including hydroxyl and isocyanate-terminated prepolymers, low molecular weight compositions used as textile coatings and finishes, and high molecular weight polyurethane compositions useful as elastomers, protective coatings and foams.

Polyurethane elastomers generally have remarkable resistance to most solvents, including gasoline, aliphatic hydrocarbons and, to some degree, aromatic hydrocarbons. They also exhibit excellent abrasion resistance. By inclusion of the polysiloxane unit in an elastomer formulation, it is possible to maintain the solvent and water resistance, improve the thermal stability and enhance the low temperature properties. The elastomers generally involve the reaction product of a diisocyanate, a linear long chain diol and a low molecular weight chain extender, such as a glycol, diamine or polyol. Elastomers are generally prepared by a prepolymer technique whereby a diisocyanate is reacted with a hydroxyl-terminated polyester or polyether to form an isocyanate-terminated prepolymer. This prepolymer is then further reacted (chain extended) with a glycol, diamine or poly functional polyol (e.g. trimethylolpropane). Following the chain extension step, the liquid material solidifies, is removed from a mold and is cured at elevated temperatures.

Urethane foams are usually prepared from diisocyanates and hydroxyl-terminated polyethers or polyesters. Linear or slightly branched polymers are used to provide flexible foams, while more highly branched polymers produce rigid foams. Foaming is often accomplished by including water in the system, the reaction between isocyanate and water providing carbon dioxide for foaming. For rigid foams a low boiling liquid, such as trichlorofluoromethane, has been used as a blowing agent. Appropriate selection of catalysts, stabilizers, surfactants and other additives controls the foam formation, cell size and type, density, cure and the like. By incorporating the polysiloxane unit into urethane foams, it is possible to achieve improved mold release properties in rigid, semi-rigid and flexible foams. It is also possible to maintain the water and solvent resistance of foams used as insulation and increase radiation resistance.

Incorporation of the polysiloxane unit into polyurethane coatings such as paints and varnishes improves the water resistance thereof. Widely used systems include the two-component coatings wherein a non-volatile isocyanate derived from the reaction of tolylene diisocyanate with a polyol such as trimethylolpropane, is reacted with a polyfunctional polyester. Another system in use involves the one-component polyurethane coatings which are based on stable isocyanate-terminated prepolymers obtained from a diisocyanate such as tolylene diisocyanate and a polyfunctional polyether. Such coatings dry by the reaction of the free isocyanate groups with water or atmospheric moisture. The reaction proceeds through the unstable carbamic acid, with $CO_2$ being eliminated, to give primary amine groups which further react with isocyanate groups to form ureas.

Treatment of a textile with a polysiloxane containing polyurethane provides oil- and water-repellent characteristics thereto.

While it is possible to build up a high molecular weight polyurethane polymer from a functionally substituted polysiloxane and a polyurethane co-reactant, most polyurethane compositions that are used commercially to any great extent are copolymers that contain only a relatively small number of urethane linkages. These copolymers are prepared from a variety of segments, typically based on polyethers and polyesters and can have a molecular weight of from 200 to 10,000, generally from about 200 to about 4,000. By the inclusion of an appropriate amount of polysiloxane in the starting materials, it is possible to prepare prepolymers that, when incorporated as part of a polyurethane, favorably affect the properties thereof. Thus, the polysiloxane unit can be present in an amount ranging from about 0.5% to about 50% by weight of the polyurethane composition, generally from 1% to about 30% by weight.

In addition to providing the polysiloxane unit as part of a prepolymer, it is possible to incorporate a desired amount of the polysiloxane unit into the reaction mixture of a conventional prepolymer and polyisocyanate so as to obtain polyurethane compositions containing the polysiloxane unit; alternatively one can use a siloxane-containing prepolymer.

The polysiloxane unit can also be incorporated in a polyurethane composition in the form of an amine-functional chain extender.

The polysiloxane-containing prepolymers can be hydroxy-terminated or isocyanate-terminated and as indicated, can have a molecular weight as high as 10,000, although a molecular weight of 200 to 4,000 is more usual.

Hydroxy-terminated prepolymers can be prepared by reacting an excess of a polyhydroxy component with a polyfunctional hydroxy-reactive component such as a polyisocyanate, an isocyanate-terminated prepolymer, a polybasic carboxylic acid, anhydride or acyl halide, phosgene, or a bischloroformate.

The polyhydroxy component can be a polyol, a bis(hydroxy) siloxane, a polyether, a polyester, a polysiloxane-containing polyether, a polysiloxane-containing polyester, or mixture thereof.

The polyols are well-known in the urethane art and include
Ethylene glycol
1,3-propanediol
1,4-butanediol
1,5-pentanediol
1,6-hexanediol
1,9-nonanediol
1,10-decanediol
di-, tri-, tetra- and pentaethylene glycol
bis(4-hydroxybutyl)ether
bis(2-hydroxybutyl thioether
bis(4-hydroxybutyl)thioether
1,4-bis(3-hydroxypropyl)benzene
glycerol
trimethylopropane
1,2,6-hexanetriol
sorbitol
mannitol
pentaerythritol
2-ethyl-1,3-butylene glycol
octamethylene glycol
2-ethyl-1,3-hexanediol
dodecamethylene glycol
tetradecamethylene glycol
hexadecamethylene glycol
octadecamethylene glycol The polyol can also contain cycloaliphatic groups, e.g. 1,4-cyclohexane-diol, 1,4-bis(hydroxymethyl)cyclohexane, 4,4'-dihydroxyl-1,1'-dicyclohexyl and the like. If desired, mixtures of polyols can be used.

Polyols, in addition to those described above, that are considered especially useful, are those containing tertiary nitrogen atoms which can be quaternized with acids, thereby converting a water-insoluble urethane composition into one that is water soluble or emulsifiable. Generally, an isocyanate-terminated prepolymer having a molecular weight of 200 to 10,000, preferably 400 to 4,000, is reacted with a difunctional tertiary amine to provide a segmented polymer containing tertiary nitrogen atoms. The nitrogen atoms can be quaternized, for example, by alkylation with methyl chloride or dimethyl sulfate to yield a composition that in polar media yields a dispersion in water. The polyammonium polyurethane compositions are obtained even more readily by neutralization of the basic polyurethane composition in a polar organic solvent such as acetone, methyl ethyl ketone, tetrahydrofuran, with a strong (HCl) or preferably weak (pK>4) acid such as the $C_2$-$C_9$ alkanoic acids. Acetic acid is especially preferred because the acetic acid evaporates with the water on drying to leave the water-insoluble hydrophobic starting polyurethane composition.

The neutralized polyurethane composition in a polar solvent spontaneously forms a dispersion when water is stirred in. The solvent can thereafter be distilled off to give a solvent-free latex whose film-forming qualities' are comparable to those of organic solution.

In a convenient mode of preparing the water-dispersible basic polyurethane compositions, a polyester or polyether diol is reacted in a non-reactive polar solvent, such as tolylene diisocyanate or, preferably an aliphatic diisocyanate which tends to give non-yellowing urethanes such as dimer acid derived diisocyanate (DDI, commercially available from Quaker Oats Company) or another diisocyanate which is described herein as providing non-yellowing urethanes, and the prepolymer partially chain extended with an alkyl diethanolamine to yield a urethane composition containing tertiary amino groups. The urethane composition can then be acidified with a solution of aqueous weak acid (pK>4) such as acetic acid; the concentration of acid is not critical. An emulsion immediately forms when this composition is added to water.

The polyurethane compositions can contain from as little as 5 to 800 milliequivalents of ammonium groups per 100 grams of polyurethane composition, preferably from about 50 to 500 milliequivalents of ammonium groups per 100 grams.

Some useful polyols containing tertiary nitrogen atoms can be represented by the formula

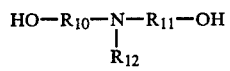

where $R_{10}$ and $R_{11}$ are alkyl of 2 to 4 carbon atoms or a group of formula

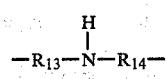

where
$R_{13}$ and $R_{14}$ are alkyl of 2 to 4 carbon atoms
$R_{12}$ is alkyl of 1 to 18 carbon atoms, cyclohexyl, tolyl, xylyl, naphthyl, or with the nitrogen atom forms piperazyl or pyridyl.

Useful polyols that contain teritary nitrogen atoms include the alkoxylated aliphatic, cycloaliphatic aromatic and heterocyclic primary amines:
N-methyl-diethanolamine
N-butyl-diethanolamine
N-oleyl diethanolamine
N-cyclohexyl-diethanolamine
N-methyl-diisopropanolamine
N-cyclohexyl-diisopropanolamine
N,N-dihydroxyethylaniline
N,N-dihydroxyethyl-m-toluidine
N,N-dihydroxyethyl-p-toluidine
N,N-dihydroxypropyl-naphthylamine
N,N-tetrahydroxyethyl-aminopyridine
dihydroxyethylpiperazine
polyethoxylated butyldiethanolamine
polypropoxylated methyldiethanolamine (molecular wt. 1000)
polypropoxylated methyldiethanolamine (molecular wt. 2000)
polyesters with tertiary amino groups
tri-2-hydroxypropyl-(1)-amine
N,N-di-n-(2:3-dihydroxypropyl)-aniline
N,N'-dimethyl-N-N'-bis-hydroxyethylhydrazine
N,N'-bis-hydroxypropylethylenediamine
N,N'-dimethyl-N-N'-bis(hydroxyethyl)-ethylenediamine
11-stearyldiethanolamine
N,N'-bis(hydroxyethyl)-piperazine The polysiloxane unit can be incorporated in the water-dispersible urethane compositions in an amount sufficient to provide the desired improvement in the surface properties of the polyurethane composition.

Useful polyethers are well-known and widely employed in urethane technology.

The polyethers are generally prepared commercially from lower alkylene oxides e.g. ethylene, propylene and butylene oxide and di- or polyfunctional alcohols. They have a molecular weight of from 400 to 5000. A list of commercially available polyethers, trade names, molecular weight range and suppliers can be found in Volume II, Polyurethane, page 511, Encyclopedia of Polymer Science and Technology, John Wiley and Sons, Inc., 1969.

Hydroxy-terminated polyesters can be prepared from a polybasic acid, anhydride or aryl halide and a polyol, as described above. The polysiloxane unit can be incorporated therein via the acid, anhydride and/or hydroxyl functionality.

Useful dicarboxylic acids are those derived from a saturated aliphatic dicarboxylic acid of 2 to 18 carbon atoms or an aromatic dicarboxylic acid of 8 to 18 carbon atoms, e.g. compounds of formula $B(COOH)_2$ where B is preferably alkylene of 0–16 carbon atoms or arylene of 6 to 16 carbon atoms. Such acids include oxalic, malonic, succinic, glutanic, adipic, pirnelic, suberic, azelaic, sebacic, brassylic, thopsic, octadecanedioie, 1-4-cyclohexanedicarboxylic, 4,4'-dicyclohexyl-1'-dicarboxylic, phthalic, isophthalic, terephthalic, methylphthalic, chlorophthalic, diphenyl-2,2'-dicarboxylic, diphenyl-4,4'-dicarboxylic, 1,4-naphthalene dicarboxylic, diphenylmethane-2,2'-dicarbosylic, diphenylmethane-3,3'-dicarboxylic, diphenylmethane-4,4'-dicarboxylic acid and the like.

Adipic acid and phthalic anhydride are the most common acid and anhydride. Of the polyols, the most commonly used include ethylene glycol, propylene glycol, 1,2-, 1,3- and 1,4-butylene glycol, 1,6-hexylene glycol, trimethylolpropane, glycerol 1,2,6-hexanetriol and diethylene glycol.

Useful hydroxyl-terminated polyesters can also be derived from natural castor oil and glycerol or from caprolactones and ethylene glycol. Such hydroxy-terminated polyesters have hydroxyl numbers ranging from 40 to 500 and very low acid numbers ranging from 0 to 2.

Hydroxyl-terminated polycarbonates can be obtained by reacting an excess of a polyol with phosgene.

Hydroxy-terminated polybutadienes, or butadienestyrenes and butadiene-acrylonitriles are useful herein, as are hydroxyl containing graft polymers of the polyetherpolyacrylonitrile type.

Any convenient polyisocyanate can be used to react with the hydroxy-functional polysiloxane or with the polysiloxane-containing hydroxy-terminated prepolymer. Myriads of useful isocyanates are well-known in the art. Thus, one can use aromatic isocyanates, diisocyanates, triisocyanates and other polyisocyanates. Useful aromatic diisocyanates can be represented by the formula

where AA is phenylene that is unsubstituted or substituted by one or two of alkyl of 1 to 4 carbon atoms, alkoxy of 1 to 4 carbon atoms, chloro, bromo and nitro, naphthylene that is unsubstituted or substituted by one or two of alkyl of 1 to 4 carbon atoms, chloro bromo and nitro
or where AA is a group of formula

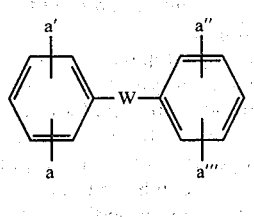

where
W is a direct bond, oxygen, methylene or ethylene and
a, a', a" and a''' each independently is hydrogen, alkyl of 1 to 4 carbon atoms alkoxy of 1 to 4 carbon atoms, chloro or bromo Aromatic triisocyanates can be represented by the formula $$BB(NCO)_3$$

where BB is the benzene or toluene group.

Aromatic di- and triisocyanates as described above include
Tolylene diisocyanate (TDI) (all isomers)
4,4'-diphenylmethane diisocyanate (MDI)
Tolidine diisocyanate
Dianisidine diisocyanate
m-Xylylene diisocyanate
p-Phenylene diisocyanate
m-Phenylene diisocyanate
1-Chloro-2,4-phenylene diisocyanate
3,3'-Dimethyl-4,4'-bisphenylene diisocyanate
3,3'-Dimethoxy-4,4'-bisphenylene diisocyanate
4,4'-Bis(2-methylisocyanatophenyl) methane
4,4'-bisphenylene diisocyanate
4,4'-Bis(2-methoxyisocyanatophenyl) methane 1-nitro-phenyl-3,5-diisocyanate
4,4'-diisocyanatodiphenyl ether
3,3'-dichloro-4'-diisocyanatodiphenyl ether
3,3'-dichloro, 4,4'-diisocyanatodiphenyl methane
4,4'-diisocyanatodibenzyl
3,3'-dimethyl-4,4'-diisocyanatodiphenyl
3,3'-dimethoxy-4,4'-diisocyanatodiphenyl
2,2'-dimethyl-4,4'-diisocyanatodiphenyl
2,2'-dichloro-5,5'-dimethoxy-4,4'-diisocyanatodiphenyl
3,3'-dichloro-4,4'-diisocyanatodiphenyl benzene-1,2,4-triisocyanate
benzene 1,3,5-triisocyanate
benzene-1,2,3-triisocyanate
toluene 2,4,6-triisocyanate
toluene 2,3,4-triisocyanate
1,2-naphthalene diisocyanate
4-chloro-1,2-naphthalene diisocyanate
4-methyl-1,2-naphthalene diisocyanate
1,5-naphthalene diisocyanate
1,6-naphthalene diisocyanate
1,7-naphthalene diisocyanate
1,8-naphthalene diisocyanate
4-chloro-1,8-naphthalene diisocyanate
2,3-naphthalnee diisocyanate
2,7-naphthalene diisocyanate
1,8-dinitro-2,7-naphthalene diisocyanate
1-methyl-2,4-naphthalene diisocyanate
1-methyl-5,7-naphthalene diisocyanate
6 0methyl-1,3-naphthalene diisocyanate
7-methyl-1,3-naphthalene diisocyanate
polymethylene polyphenyl isocyanate and co-products of hexamethylene diisocyanate and tolylene diisocyanate Useful aliphatic diisocyanates include those of general formula $$AA(NCO)_2$$

where AA is alkylene of 2 to 16 carbon atoms. Useful aliphatic polyisocyanates include
1,2-ethane diisocyanate
1,3-propane diisocyanate
1,4-butane diisocyanate
2-chloropropane-1,3-diisocyanate
pentamethylene diisocyanate
propylene-1,2-diisocyanate
1,6-hexane diisocyanate
1,8-octane diisocyanate
1,10-decane diisocyanate
1,12-didecane diisocyanate
1,16-hexandecane diisocyanate and other aliphatic diisocyanates such as
1,3-cyclohexane diisocyanate
1,4-cyclohexane diisocyanate
cyclohexane triisocyanate
4,4'-methylene bis(cyclohexyl) isocyanate Additionally, the following diisocyanates are particularly preferred because urethane compositions made therefrom tned to be non-yellowing:
1,6-hexamethylenediisocyanate (HDI)
2,2,4- and 2,4,4-trimethylhexamethylenediisocyanate (TMDI)
dimeracid derived diisocyanate (DDI) obtained from dimerized fatty acids, such as
linoleic acid 4,4'-dicyclohexylmethane diisocyanate (hydrogenated MDI)
isophorone diisocyanate
3-isocyanatomethyl-3,5,5-trimethylcyclohexylisoyanate
lysine methyl ester diisocyanate (LDIM)
bis(2-isocyanatoethyl) fumarate (FDI)
bis(2-isocyanatoethyl) carbonate Other useful isocyanates include polyisocyanates particularly triisocyanates which are readily obtained by the reaction of an excess of the corresponding diisosyanate with water according to the following equation:

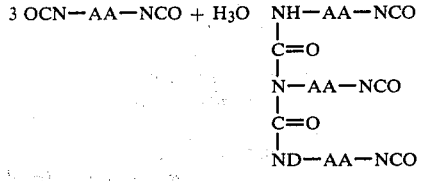

where AA is the residue of a diisocyanate as described above; additional polyisocyanates include polymethylene polyphenylisocyanate (PAPI) and tris-(isocyanatophenyl) thiophosphate (Desmodur R).

Additional isocyanate components can be prepared by reacting an excess of a diisocyanate as described above with a suitable hydroxyl component, such as a polyol described above or combination thereof, to obtain an isocyanate-terminated prepolymer.

In addition to the polyisocyanates, useful urethane compositions can be obtained from the aliphatic and aromatic monoisocyanates. The low molecular weight urethane compositions obtained by reacting a hydroxy-functional polysiloxane with a monoisocyanate are useful to impart soil and mold-release properties to a variety of natural and synthetic polymers.

Some useful aromatic monoisocyanates include
2-fluorophenyl isocyanate
3-fluorophenyl isocyanate
4-fluorophenyl isocyanate
m-fluorosulfonylphenyl isocyanate
trans-2-phenylcyclopropyl isocyanate
m-tolyl isocyanate
p-tolyl isocyanate
$\alpha,\alpha,\alpha$-trifluoro-o-tolyl isocyanate
$\alpha,\alpha,\alpha$-trifluoro-m-tolyl isocyanate
p-bromophenyl isocyanate
2,5-dimethylphenyl isocyanate
o-ethoxyphenyl isocyanate
p-ethoxyphenyl isocyanate
o-methoxyphenyl isocyanate
m-methoxyphenyl isocyanate
p-methoxyphenyl isocyanate
1-naphthyl isocyanate
o-nitrophenyl isocyanate
m-nitrophenyl isocyanate
p-nitrophenyl isocyanate
p-phenylazophenyl isocyanate
o-tolyl isocyanate Useful aliphatic monoisocyanates include such alkyl isocyanates of 1 to 16 carbon atoms as
methyl isocyanate
ethyl isocyanate
n-propyl isocyanate
n-butyl isocyanate
t-butyl isocyanate
hexyl isocyanate
octyl isocyanate
dodecyl isocyanate
octadecyl isocyanate
hexadecyl isocyanate
and mixtures thereof, as well as cyclohexyl isocyanate.

Isocyanate-terminated prepolymers typically having a molecular weight of from 200 to about 400 can be prepared by reacting an excess of an isocyanate component with an polyhydroxy component. The isocyanate component can be a diisocyanate or polyisocyanate as previously described, or can be a low molecular weight isocyanate-terminated prepolymer.

The hydroxy component can be one or more of a polyol, polyester, polyether, polycarbonate and hydroxy-functional polysiloxane, all as described previously.

It can be seen that the properties of ultimate urethane compositions can be modified by appropriate modifications in the compositions of the prepolymers.

The reaction between the isocyanate component and the hydroxyl component can be carried out in bulk, i.e., without solvent, or in the presence of non-reactive, anhydrous, organic solvents. Solvent media in which the reaction can be carried out include ketones, such as acetone, methyl ether ketone and methylisobutyl ketone; esters such as ethyl acetate, butylacetate, 2-ethylhexyl acetate; hydrocarbons such as hexane, haptane, octane and higher homologs, cyclohexane, benzene, toluene, xylene or blends of aliphatic, cycloaliphatic and aromatic hydrocarbons. It is also possible to employ ethers, both aliphatic and alicyclic including di-n-propyl ether, di-butyl ether, tetrahydrofuran and the diethers of polyalkylene oxides. In addition, chlorinated solvents such as dichloroethyl ether, ethylene dichloride perchloroethylene and carbon tetrachloride can be used.

In all cases, the solvents should be anhydrous to avoid urea formation.

The reaction can, if desired, be catalyzed and those catalysts conventionally employed in the urethane art are useful herein. Useful catalysts fall principally in two groups a. amino compounds and other bases:
triethylamine and other trialkylamines
triethylenediamine
1,4-diaza-2,2,2-bicyclooctane
N-(lower) alkyl morpholines
N,N,N',N'-tetra-methylethelenediamine
N,N,N',N'-tetramethyl-1,3-butanediamine
N,N,N',N'-substituted piperazines
dialkylalkanolamines
benzyltrimethylammonium chloride b. organometallic and inorganic compounds:
cobalt naphthenate
stannous chloride
stannous actoate
stannous oleate
dimethyl tin dichloride
di-n-butyltin dilaurlmercaptide
tetra-n-butyl tin
trimethyl-tin hydroxide
di-n-butyltindilaurate Such catalysts may be used singly or in combination with each other. Beneficial synergistic catalysis may occur when combinations are used.

While it is possible to carry out the reaction without the use of a catalyst, it is preferable for reasons of economy and to assure a complete reaction, to utilize one or more catalysts as listed in amounts ranging from 0.001 to 1% based on the weight of the reactants. It is similarly advantageous to carry out the urethane synthesis at elevated temperature, usually between room temperature and 120° C. and preferably at 60° to 80° C. to obtain a complete reaction between 0.5 to 8 hours reaction time.

The reaction can be easily followed by titration of the isocyanate group or by IR analysis.

From the foregoing discussion it is seen that the siloxane unit can be incorporated into a polyurethane polymer in a variety of ways; the resulting polyurethane composition has improved properties that were previously unavailable via a siloxane-containing molecule.

10. Polyamide

The term "nylon" generically describes a family of thermoplastic polyamide resins stemming from two basic chemical intermediate groups. The first in the condensation polymerization of a diamine and a diacid; for example, the reaction of hexamethylene diamine with adipic acid:

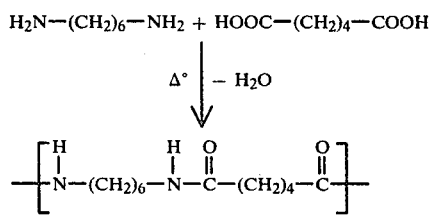

Hexamethylene diamine is a widely used diamine; typical acids include adipic, azelaic, sebacic and dodecanedoic.

The second group utilizes amino acids or amino acid derivatives, such as caprolactam, aminoundecanoic acid and lauryllactam:

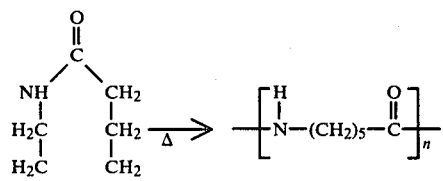

The properties of polyamide polymers can be improved by the incorporation therein of a siloxane unit of formula

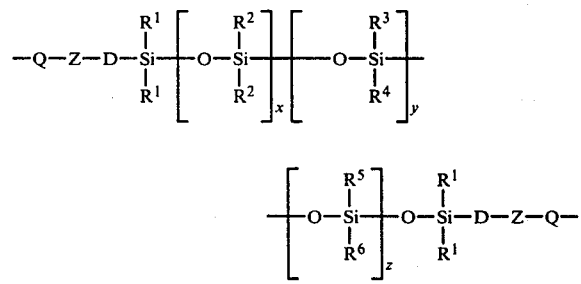

where the various elements are as previously described.

There can be incorporated from 0.01 to about 30 mole % of the siloxane unit, initially present as either the diamine or the diacid. In general, there can be present from 0.1 mole % to 15 mole % of the siloxane and at these levels there is seen an improvement in the various properties. Thus, there is obtained a siloxane-modified polyamide polymer having improved heat stability, lower surface friction, improved surface wear characteristics for moving contact mechanical applications and improved mold release. The polyamide also has improved resistance to hydrolysis and to chemicals.

The polymers have good impact strength and ductility as well as improved UV resistance. They can be molded or extruded.

In one embodiment there is contemplated the reaction product of a bis(amino)siloxane with a diacid; in another embodiment, there is contemplated the reaction product of a bis(carboxy)siloxane with a diamine to form part of a polyamide.

Throughout this specification the siloxane unit has been depicted as being divalent:

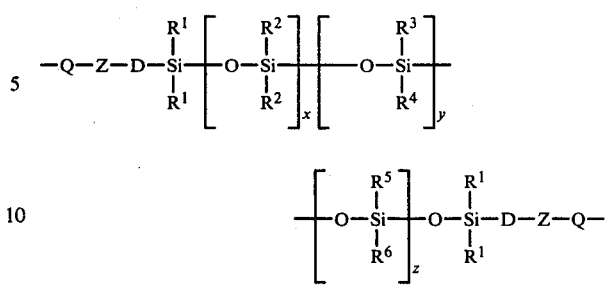

It is apparent, however, that the unit can be bonded to a polymer matrix in a polyvalent fashion and that the depiction of the unit as divalent is merely a convenient simplification. Specifically, the dianhydride will yield a tetravalent unit while the acid-anhydride will yield a trivalent unit. Reactive groups on Q in addition to F, and reactive groups on the silicone substituents will provide a polyvalent unit. Thus, depiction of the siloxane unit as divalent is intended to be illustrative and not limiting.

The foregoing specification has described a variety of molecular configurations and applications of a polysiloxane to whose surprising heat resistance and stability these are attributable. The properties and applications of some of these polysiloxanes are illustrated in the following Examples; it will be immediately apparent that the chemicals arts now have a new means for modifying a variety of polymers and for synthesizing compositions useful in a spectrum of applications.

EXAMPLE 1

Preparation of Bis-(p-aminophenylthiobutyl)tetramethyl-Disiloxane

A glass reactor is charged with 43.28 parts of a 50% aqueous sodium hydroxide solution, 112 parts dimethylsulfoxide (DMSO), 120 parts toluene and 68.75 parts p-aminothiophenol. The reaction is heated to the boiling point under a nitrogen atmosphere with rapid agitation. The water present in the reactor is removed by azeotropic distillation and collected in a Dean Stark trap. The organic solvent that collects in the trap is returned to the reaction mixture. The temperature of the reaction mixture increases from an initial 110° C. to about 122° C. while the reaction mixture is stirred for between 7 and 8 hours. At the end of this time period water is no longer evolved from the reaction mixture.

The reaction mixture is then cooled to about 80° C., at which time 86.6 parts of bis-(chlorobutyl)tetramethyldisiloxane is added dropwise to the reaction mixture. The chemical reaction which occurs during this addition is slightly exothermic, and the rate of the addition is controlled to maintain the reaction mixture temperature at about 80° C. Upon completion of the disiloxane addition, the reaction mixture is heated at a temperature of 80° C. for a period of about 16 hours.

Samples from the reaction mixture are removed periodically and analyzed by means of vapor phase chromatography. When the amount of product, as indicated by a new peak having a longer retention time relative to the starting materials reaches a maximum value, the reaction is considered to be complete. The reaction mixture is then filtered and the solvents, toluene and DMSO, are removed under a reduced pressure of about 10 mm of mercury. The residue is then distilled and the desired end product is recovered at a temperature of from about 310° C. to 315° C. at from 0.1 mm to 0.5 mm (Hg) pressure. The chemical structure is confirmed by analytical infrared spectroscopy, and corresponds to the structure of the desired product, bis-(p-aminophenylthiobutyl)tetramethyldisiloxane. The yield of this material is about 85 percent.

EXAMPLE II

Preparation of Bis-(p-aminophenoxybutyl)Tetramethyl-Disiloxane

The procedure described in Example I is repeated substituting 59.95 parts of p-aminophenol for the p-aminothiophenol and the final product is recovered by distillation at a temperature of from 295° C. to about 300° C. under a pressure of from 0.5 mm to about 2 mm pressure of mercury. The final product is identified as bis(p-aminophenoxybutyl)tetramethyldisiloxane. This compound is initially a colorless liquid which eventually solidifies to a white solid which melted from 48° C. to 49° C.

EXAMPLE III

Preparation of Bis-(m-aminophenoxypropyl)Tetramethyl-Disiloxane

The process described in Example I was repeated substituting 59.95 parts of m-aminophenol for the p-aminothiophenol and 78.9 parts of bis-(chloropropyl)tetramethyldisiloxane for the bis-(chlorobutyl)tetramethyldisiloxane. The end product was recovered by distillation within the temperature range of from 245° C. to 260° C. under a pressure of from 0.5 mm to 2.0 mm of mercury. This product was identified as bis-(aminophenoxypropyl)tetramethyldisiloxane, a pale yellow liquid which did not solidify upon standing at 0° C. for three days. Its pority, as determined by titration with perchloric acid, exceeded 99%.

EXAMPLE IV

Preparation of Bis-(p-aminophenylsulfoxobutyl)tetramethyldisiloxane

A quantity of bis-(p-aminophenylthiobutyl)tetramethyldisiloxane, prepared as described in Example I, is dissolved in chloroform and the resultant solution is cooled in an ice bath. A solution of m-chloroperbenzoic acid in chloroform (an equimolar amount based on disiloxane) is then added dropwise to the reaction mixture with stirring, and stirring is continued for ½ hour following completion of the addition. The solid phase of the reaction mixture is removed by filtration and the chloroform present in the filtrate is evaporated under reduced pressure to isolate the desired product, which corresponds to the formula

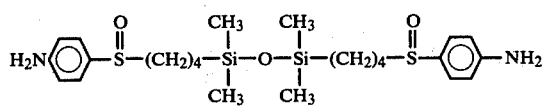

EXAMPLE V

Preparation of Bis-(p-aminophenylsulfobutyl)tetramethyl Disiloxane

A reactor equipped with a reflux condenser, agitator and an nitrogen inlet is charged with one mole of sodium p-aminobenzene sulfonate dissolved in dimethyl sulfoxide. To this solution is gradually added 0.5 mole of bis-(chlorobutyl)tetramethyldisiloxane. The rate of addition is controlled to maintain the temperature of the reaction mixture at about 80° C. Upon completion of the disiloxane addition the reaction mixture is heated at a temperature of 80° C. for a period of about 16 hours. The reaction mixture is then filtered and the solvents evaporated as described in Example I to obtain a product that corresponds to formula

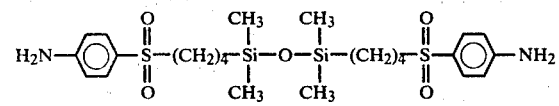

EXAMPLE VI

A. Preparation of Bis(p-aminophenylsulfamylbutyl) tetramethyl disiloxane

A glass reactor is charged with 34.4 grams of p-aminobenzenesulfamide, 16 grams of sodium hydroxide, in the form of a 50% aqueous solution, 60 mole of dimethylsulfoxide and 56 mole of toluene under nitrogen and heated to the boiling point in a nitrogen atmosphere with rapid agitation. Water formed is removed azeotropically and collected in a Dean Stark trap. When the reaction is complete, as evidenced by no further evolution of water, the reaction mixture is cooled to about 80° C. and 31.5 grams of bis(chlorobutyl) tetramethyl disiloxane is added dropwise; the reaction is slightly exothermic and the addition rate is adjusted to maintain the reaction mixture at about 80° C. Upon completion of the addition, the mixture is stirred for about 16 hours at about 80° C.

When the reaction is complete, the solvents are removed and the product recovered in accordance with the procedure of Example 1.

B. Preparation of Bis(p-aminophenylcarbamoylpropyl) tetramethyl disiloxane

Under nitrogen, a glass reactor is charged with 27.2 grams p-aminobenzamide, 16 grams sodium hydroxide as a 50% aqueous solution, 60 mole dimethyl sulfoxide and 56 mole toluene and reacted as in Example VIA, above.

When the reaction is complete, the mixture is cooled to about 80° C. and 28.7 grams of bis(chloropropyl) tetramethyl disiloxane are added dropwise.

The reaction conditions described in Example VIA are followed and the product is recovered; structurs is confirmed by IR and NMR analysis.

C. Preparation of Bis(p-aminophenylcarbonyloxybutyl) tetramethyl disiloxane

Following the procedure of Example VIA, there is reacted
p-aminobenzoic acid 137 grams
NaOH 40 grams in 200 ml H₂O
Xylene 1000 ml When the system is anhydrous, the temperature is lowered to about 110° C. and 10 grams of terabutylphosphonium chloride are added all at once. There is then initiated the dropwise addition of 157.5 grams of bis(chlorobutyl) tetramethyl disiloxane. Upon completion of the addition, the mixture was stirred overnight at 115° C.

The product was worked up as indicated in Example VIA; it was a viscous oil whose structure was confirmed by IR and NMR analysis.

The product was purified by forming an ethanol solution of the bis (amine dihydrochloride) and recrystallizing it.

EXAMPLE VII

Preparation of Bis(aminophenoxymethyl) tetramethyl disiloxane

Following the procedure described in Example 1, the following ingredients were combined and reacted in a glass reactor under nitrogen:
m-aminophenol: 56.86 parts by wt.
toluene: 120.0 parts by wt.
dimethylsulfoxide: 112.0 parts by wt.
50% NaOH solution: 43.28 parts by wt.

When the reaction was complete, as indicated by termination of water evolution, the reaction temperature is reduced to 75° C. and dropwise addition of 63.5 parts by wt. of bis(chloromethyl) tetramethyl disiloxane initiated. After complete addition, the reaction mixture is stirred at 75° C.

At the end of the reaction the mixture was filtered and the solvents removed under vacuum at 5-10 mm of mercury. The residue was distilled, the product coming over at 254° C. at 7 mm of mercury as a yellow oil; yield was about 85%. The chemical structure was confirmed by IR and NMR analysis as:

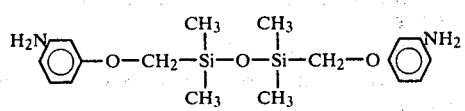

EXAMPLE VIII

Preparation of Bis(aminophenoxyoctyl) tetramethyl disiloxane

1. Preparation of bis(8-bromooctyl) tetramethyl disiloxane. The Pt catalyzed addition of chlorodimethylsilane to 1,7-octadiene provides 7-octenyldimethylchlorosilane. The peroxide-catalyzed addition of HBr to this intermediate yields 8-bromooctyl dimethyl chlorosilane; this is hydrolyzed to provide bis(8-bromooctyl)tetramethyl disiloxane.

2. The reaction conditions of Example VII are repeated, except that the bis (chloromethyl) tetramethyl disiloxane is replaced by 139.32 parts by weight of bis(8-bromooctyl) tetramethyl disiloxane.

EXAMPLE IX

Preparation of Bis-(p-amino-o-chlorophenoxybutyl)tetramethyldisiloxane

The procedure described in Example I is repeated substituting 2-chloro-4-aminophenol for the p-aminothiophenol, which is reacted with a stoichiometric amount (1:1 molar ratio) of a 50% aqueous sodium hydroxide solution. The resultant sodium phenoxide solution is reacted with a stoichiometric amount of bis-(chlorobutyl) tetramethyldisiloxane to form a product of formula

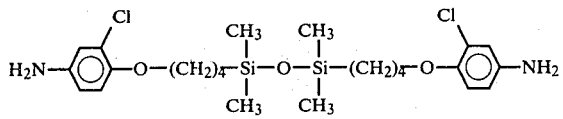

EXAMPLE X

Preparation of 1,3-Bis-(p-formylphenoxypropyl)tetramethyl Disiloxane

The procedure described in Example I was repeated using 67.1 parts of p-formylphenol in place of the p-aminothiophenol, and 91.57 parts of chloropropyldimethylmethoxysilane in place of the bis-(chlorobutyl)tetramethyldisiloxane. The end product was recovered by distillation at a temperature within the range of from 215° C. to 230° C. under a pressure of from 0.1 mm to 0.5 mm of mercury. The recovered end product was a colorless liquid and was identified as p-formylphenoxypropyldimethylmethoxysilane. Its purity, as determined by vapor phase chromatography, was 99%. The product yield was 60%.

This material was then added to a large excess of methanol containing a 100% excess of the amount of water sufficient to convert all the alkoxysilane to the disiloxane. A pellet of KOH was also added as a catalyst. The reaction remained at ambient temperature for about 16 hours with constant stirring. The methanol and water were removed by distillation, and the disiloxane was recovered by a molecular distillation. The chemical structure of the product recovered was confirmed by infrared and nuclear magnetic resonance spectra and corresponded to 1,3-bis-(p-formylphenoxypropyl)-tetramethyldisiloxane.

EXAMPLE XI

Preparation of 1,3-Bis-m-(N-Methylaminophenoxypropyl) Tetramethyldisiloxane

The procedure of Example X was repeated substituting 67.65 parts of m-(N-methylamino)phenol for the p-formylphenol. The final product was recovered at a temperature within the range of from 170° C. to 175° C. under a pressure of from about 0.1 mm to 0.5 mm of mercury. This product was a very pale yellow liquid identified as m-(N-methylamino)phenoxypropyldimethylmethoxysilane. The silane product was hydrolyzed to 1,3 bis-m(N-methylaminophenoxypropyl)tetramethyldisiloxane in the same manner described in Example X.

EXAMPLE XII

Preparation of 1,3-Bis(p-Carbomethoxyphenoxypropyl) Tetramethyldisiloxane

The procedure of Example X was repeated substituting 83.6 parts of p-carbomethoxyphenol for the p-formylphenol. The end product was recovered by distillation at a temperature within the range of from 185° C. to 200° C. under a pressure of from 0.5 mm to 2.0 mm of mercury. This product was a colorless liquid identified as p-carbomethoxyphenoxypropyldimethylmethoxysilane. The silane product was hydrolyzed to 1,3-bis-(p-carbomethoxyphenoxypropyl)tetramethyldisiloxane in the same manner described in Example X.

EXAMPLE XIII

Preparation of 1,3-Bis(m-Hydroxyphenoxybutyl)Tetramethyl-Disiloxane

The procedure of Example I is repeated using 83.6 parts of resorcinol monoacetate in place of the p-aminothiophenol. The stripped mixture is distilled at a temperature of 270° C. to 280° C. at from 0.1 mm to 0.5 mm pressure. The product is 1,3-bis(m-acetoxyphenoxybutyl)tetramethyldisiloxane; this acetate ester is hydrolyzed with HCl to obtain the hydroxy compound.

EXAMPLE XIV

Preparation of 1,3-Bis(p-Carboxyphenoxybutyl)Tetramethyl-Disiloxane

A reaction mixture consisting of 8 parts NaOH in 200 parts $H_2O$ and 54.6 parts of 1,3-bis(p-carbomethoxyphenoxybutyl)tetramethyldisiloxane (see Example XII) were combined and heated to reflux. The mixture was initially heterogeneous but became homogeneous after three hours, at which time the reaction was terminated, extracted two times with 100 ml. toluene and acidified with excess HCl. A white precipitate formed, which was filtered and recrystallized from pentane. The structure was confirmed by I.R. and N.M.R.

EXAMPLE XV

Preparation of 1,3-Bis(p-Bromophenoxybutyl)Tetramethyl-Disiloxane

A three-necked flask is charged with 43.28 parts of 50% aqueous sodium hydroxide solution, 112 parts dimethylsulfoxide (DMSO), 120 parts toluene and 95.15 parts p-bromophenol. The reaction is brought to reflux in a nitrogen atmosphere with rapid agitation. The water of the charged ingredients (the aqueous hydroxide solution) and the water formed during the neutralization reaction is removed azeotropically and collected in a Dean Stark trap. The refluxing solvent is returned to the reaction mixture. The pot temperature, that is the temperature of the reaction mixture, climbs from an initial 110° C. to about 118° C. during a period of from 7 to 8 hours of stirring. At the end of this time period water is no longer evolved from the reaction mixture.

The reaction mixture is then cooled to about 80° C. At this temperature of about 80° C., 86.6 parts of bis(chlorobutyl)tetramethyldisiloxane is added dropwise to the reaction mixture. The chemical reaction which occurs during the dropwise addition is slightly exothermic. Therefore, the addition is controlled to retain the reaction temperature at about 80° C. Upon completion of the siloxane addition, the reaction is allowed to proceed at about 80° C. for a period of time which is usually overnight.

The reaction is monitored such, for example, as by use of a GC analytical means. When GC analysis indicates a new peak having a long retention time is maximized, the reaction is complete.

The reaction mixture is filtered and the solvents, toluene and DMSO, are removed under a reduced pressure of about 10 mm. The stripped mixture is distilled and the desired end product is recovered at a temperature of from about 170° C. to 180° C. at from 0.1 mm to 0.5 mm pressure. The chemical structure is confirmed by chemical analysis using I.R. and N.M.R.

EXAMPLE XVI

Preparation of 1,3-Bis(m-Ethylaminophenoxybutyl)Tetramethyl-disiloxane

The procedure of Example XV is repeated using 75.35 parts of m-ethylaminophenol in place of the bromophenol. The product is distilled at 180° C. to 190° C. at 0.1 mm to 0.5 mm pressure.

EXAMPLE XVII

Preparation of 1,3-Bis(Cyanophenoxybutyl)Tetramethyl-Disiloxane

The procedure of Example XV is repeated using 65.45 parts of p-cyanophenol. The product is distilled at 285° C. to 300° C. at 0.1 mm to 0.5 mm pressure.

EXAMPLE XVIII

Preparation of 1,3-bis(p-acetylphenoxybutyl)Tetramethyl-Disiloxane

The procedure of Example XV is repeated using 74.8 parts of p-acetylphenol. The product is distilled at reduced pressure.

EXAMPLE XIX

Preparation of bis(p-aminophenylthiobutyl)tetramethyldisiloxane using phase transfer catalyst Example I illustrates the use of a dipolar aprotic solvent in the synthesis of a disiloxane. This example repeats that synthesis, using a phase transfer catalyst.

A three-necked flask was charged with 43.28 parts of 50% aqueous sodium hydroxide solution and 68.75 parts p-aminothiophenol. The charged ingredients were heated to 50° C. and stirred continuously for ½ hour to ensure complete neutralization of the ingredients.

232 parts toluene was added to the flask to form a reaction mixture. The reaction mixture was heated to reflux in a nitrogen atmosphere while being rapidly agitated. The water of the charged ingredients (the aqueous hydroxide solution) and the water formed during the neutralization reaction was removed azeotropically and collected in a Dean Stark trap. The refluxing solvent was returned to the reaction mixture. The pot temperature, that is the temperature of the reaction mixture, climbed from an initial 110° C. to about 120° C. during a period of from 7 to 8 hours of stirring. At the end of this time period water was no longer being evolved from the reaction mixture.

The reaction mixture was then cooled to about 80° C. At this temperature of about 80° C., there was added at once 4 grams tetrabutyl ammonium chloride and 86.6 parts of Bis-(chlorobutyl)tetramethyldisiloxane was also added dropwise to the reaction mixture. The chemical reaction which occurred during the dropwise addition was slightly exothermic. Therefore, it is preferred that the addition must be controlled to retain the reaction temperature at about 80° C. Upon completion of the silane addition, the reaction was allowed to proceed at about 80° C. for a period of time which extended overnight while being constantly agitated.

The reaction was monitored by use of a GC analytical means. When GC analysis indicated a new peak having a long retention time had become maximized, the reaction was complete.

The reaction mixture was filtered and the solvent, toluene was removed under a reduced pressure of about 10 mm. The stripped mixture was distilled and the desired end product recovered at a temperature of from about 310° C. to 315° C. at from 0.1 mm to 0.5 mm pressure. The chemical structure was confirmed by I.R. and N.M.R. means.

EXAMPLE XX

Preparation of bis-(p-aminophenoxybutyl)Tetramethyl-Disiloxane

The same process of Example XIX was practiced except that 59.95 parts of p-aminophenol was substituted for p-aminothiophenol and the tetrabutyl ammonium chloride was replaced with 4 grams tetrabutyl phosphonium chloride and the end product was recovered at from 0.5 mm to about 2 mm pressure of mercury. The recovered product was identified as Bis-(p-aminophenoxybutyl) tetramethyldisiloxane.

EXAMPLE XXI

Preparation of bis-(m-aminophenoxybutyl)tetramethyldisiloxane using macrocyclic crown ether as phase transfer catalyst The process of Example XIX was again practiced except that 59.95 parts of m-aminophenol was substituted for the p-aminothiophenol and 78.9 parts of Bis-(chloropropyl)tetramethyldisiloxane was substituted for the Bis-(chlorobutyl)tetramethyldisiloxane, and the phase transfer catalyst was 3 grams of 18 crown −6 ether. The end product was recovered at a temperature within the range of from 245° C. to 260° C. at from 0.5 mm to 2.0 mm of mercury. The recovered product was identified as Bis-(m-aminophenoxypropyl)tetramethyldisiloxane. The recovered product material was a pale yellow liquid which did not solidify upon standing in the cold at 0° C. for 3 days. Its purity, as determined by titration with perchloric acid, was better than 99%.

EXAMPLE XXII

Preparation of 1,3-Bis-(p-formylphenoxypropyl)tetramethyldisiloxane using phase transfer catalyst The process of Example XIX was again followed, except that 67.1 parts of p-formylphenol was substituted for the p-aminothiophenol and 91.57 parts of chloropropyldimethylmethoxysilane was substituted for the Bis-(chlorobutyl)tetramethyldisiloxane. The phase transfer catalyst was 5 grams cetyltrimethylammoniumbromide. The end product was recovered at a temperature within the range of from 215° C. to 230° C. at from about 0.1 mm to 0.5 mm of mercury. The recovered end product was a colorless liquid and was identified as p-formylphenoxypropyldimethylmethoxysilane. Its purity, as determined by GC, was 99%. The product yield was 60%.

The end product was then added to a large excess of methanol containing 100% excess of water sufficient to convert all the alkoxysilane to the disiloxane. A pellet of KOH was also added to the reaction as a catalyst to facilitate the reaction. The reaction was carried out overnight at room temperature while being constantly stirred. The methanol and excess water was removed by distillation, and the disiloxane was recovered by a molecular distillation. The chemical structure of the product recovered was confirmed by I.R. and N.M.R. as 1,3-Bis-(p-formylphenoxypropyl)tetramethyldisiloxane.

EXAMPLE XXIII

Preparation of 1,3-Bis-(m-methylaminophenoxypropyl)tetramethyl-disiloxane using phase transfer catalyst The process of Example XXII was practiced except that 67.65 parts of m(N-methylamino)phenol was substituted for the p-formylphenol. The phase transfer catalyst was 5 grams of triphenylbenzylphosphonium chloride. The end product was recovered at a temperature within the range of from 170° C. to 175° C. at a pressure of from about 0.1 mm to 0.5 mm of mercury. The recovered end product was a very pale yellow liquid identified as Bis-(m-methylamino)phenoxypropyldimethyl-methoxysilane. The silane product was hydrolized to 1,3 Bis-(m-methylaminophenoxypropyl)tetramethyldisiloxane in the same manner described in Example XXII.

EXAMPLE XXIV

Preparation of 1,3-Bis-(p-carbomethoxyphenoxypropyl)tetramethyldisiloxane

The process of Example XXII was practiced except that 83.6 parts of p-carbomethoxyphenol was substituted for the p-formylphenol. The end product was recovered at a temperature within the range of from 185° C. to 200° C. at a pressure of from 0.5 mm to 2.0 mm of mercury. The recovered end product was a colorless liquid identified as p-carbomethoxyphenoxypropyldimethylmethoxysilane. The silane product was hydrolized to 1,3-Bis-(p-carbomethoxyphenoxypropyl)-tetramethyldisiloxane in the same manner described in Example XXII.

In a similar manner, by employing the procedures of the preceeding examples, siloxanes containing a variety of functional groups can be prepared; those groups have been discussed previously and their specific configuration will be determined by the characteristics desired.

EXAMPLE XXV

Preparation of the polysiloxane of formula

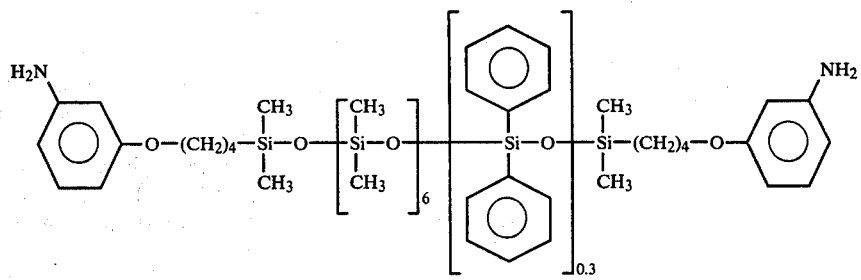

About 0.1 gram of potassium hydroxide was added to a reaction mixture containing 46 grams Bis(m-aminophenoxybutyl)tetramethyldisiloxane, 44.4 grams octamethylcyclotetrasiloxane (hereinafter referred to as "phenyl tetramer") under a nitrogen atmosphere. The reaction mixture was then heated at the boiling point (178° C.) for 3 hours, at which time the boiling point began to increase. When the boiling point reached 215° C., the reaction mixture was maintained at this temperature for an additional 6 hours, then cooled to room temperature. A 1 gram portion of sodium bicarbonate was then added to the reaction mixture and the mixture was stirred rapidly for 15 minutes.

The reaction mixture was then filtered to obtain a product which was a homogeneous amber liquid. The amino content was determined by titration of an aliquot portion of the product using a 0.01N perchloric acid solution to a bromcresol purple end point. The titration indicated that 3.32% by weight of amine groups were present. Based on this amine content and the amount of starting materials, the general formula of the product was calculated.

EXAMPLE XXVI

Preparation of the polysiloxane formula

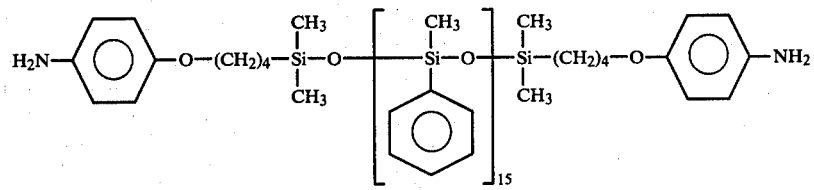

A 1 cc portion of a solution containing 50 ppm tetrabutyl phosphonium trimethylsilanolate in methyl tetramer was added to a reaction mixture containing 612 grams 1,3,5,7-tetramethyl, 1,3,5,7-tetraphenylcyclotetrasiloxane and 138 grams Bis(p-aminophenoxybutyl)tetramethyldisiloxane under a nitrogen atmosphere. The reaction mixture was heated at 115° C. for 4 hours. During this period of time, the viscosity of the reaction mixture was observed to increase and to then reach a stable value. At the end of the 4-hour period, the temperature of the reaction mixture was raised to 160° C. for 3 hours to effect destruction of the catalyst. The reaction mixture was cooled to room temperature and filtered to obtain an end product which had a deep amber color.

An aliquot of the end product was titrated with a 0.10N perchloric acid solution to a bromcresol purple end point. The amount of perchloric acid required was equivalent to 1.2% by weight of amine groups in the product. Based on this value and the amount of starting materials, the general formula for the product was calculated.

EXAMPLE XXVII

Preparation of the polysiloxane of formula

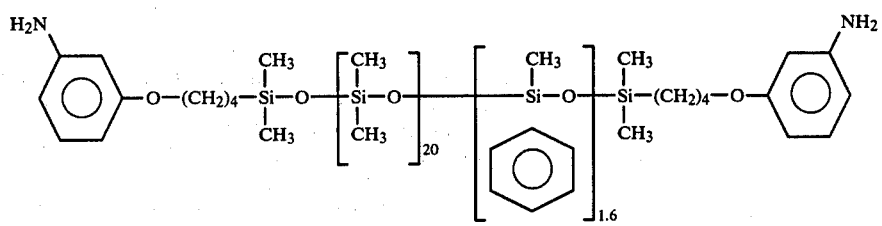

The equilibrated amino functional polysiloxane of the general formula indicated above was prepared by the equilibration of Bis(m-aminophenoxybutyl)tetramethyldisiloxane with octamethylcyclotetrasiloxane and 1,3,5,7-tetramethyl, 1,3,5,7-tetraphenylcyclotetrasiloxane.

Two pellets of potassium hydroxide, equivalent to about 0.1 gram, were added to a reaction mixture containing 4.6 grams Bis(m-aminophenoxybutyl)tetramethyldisiloxane, 14.8 grams octamethylcyclotetrasiloxane, and 2.2 grams 1,3,5,7-tetramethyl, 1,3,5,7-tetraphenylcyclotetrasiloxane under a nitrogen atmosphere. The reaction mixture was heated to the boiling point which gradually increased to 215° C. during a two hour period. The reaction mixture was maintained at this temperature for eight hours, after which it was cooled to room temperature and 1 gram of tris-chloroethylphosphite was added to destroy the potassium hydroxide catalyst.

The reaction mixture was then filtered. An aliquot of the filtrate, a homogeneous amber fluid, was titrated with 0.10N perchloric acid solution to a bromcresol purple end point. The amount of perchloric acid required was equivalent to 1.32% by weight of amine groups in the product. Based on this value and the amount of starting materials, the general formula for the product was calculated.

EXAMPLE XXVIII

Preparation of the polysiloxane of formula

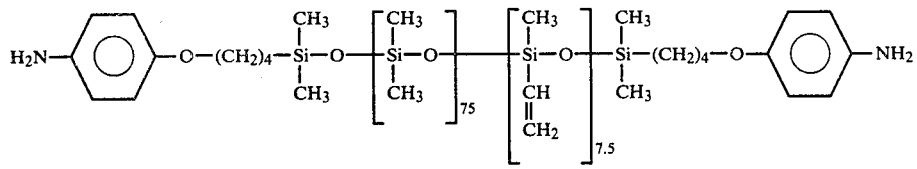

The equilibrated amino functional polysiloxane of the general formula indicated above was prepared by the equilibration of Bis(p-aminophenoxybutyl)tetramethyldisiloxane with octamethylcyclotetrasiloxane and 1,3,5,7-tetramethyl, 1,3,5,7-tetravinylcyclotetrasiloxane.

One half gram of tetrabutylammonium hydroxide was added to a reaction mixture containing 4.6 grams Bis p-(aminophenoxybutyl)tetramethyldisiloxane, 55.5 grams octamethylcyclotetrasiloxane and 6.4 grams 1,3,5,7 tetramethyl, 1,3,5,7-tetravinylcyclotetrasiloxane under a nitrogen atmosphere. The reaction mixture was then maintained at a temperature of 110° C. for 8 hours. The temperature of the reaction mixture was then raised to 160° C. and maintained at this level for 3 hours, following which the reaction mixture was cooled to room temperature and filtered. An aliquot of the filtrate, a homogeneous amber fluid, was titrated with a 0.01N perchloric acid solution to a bromcresol purple end point. The amount of perchloric acid required was equivalent to 0.43% by weight of amine groups in the product. Based on this and the amount of starting materials, the general formula for the product was calculated.

EXAMPLE XXIX

Preparation of the polysiloxane formula

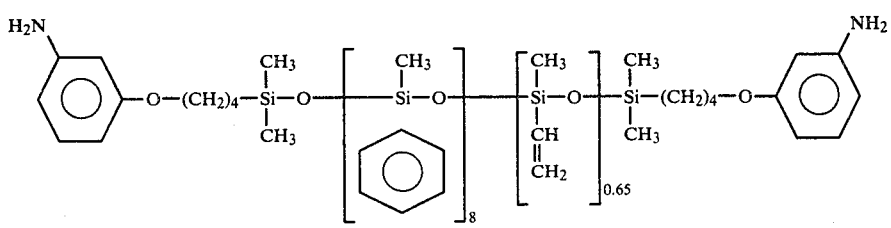

The equilibrated amino functional polysiloxane of the general formula indicated above was prepared by the equilibration of Bis(m-aminophenoxybutyl)tetramethyldisiloxane with 1,3,5,7-tetramethyl-1,3,5,7-tetraphenylcyclotetrasiloxane and 1,3,5,7-tetramethyl-1,3,5,7-tetravinylcyclotetraxiloxane.

One half gram potassium hydroxide was added to a reaction mixture containing 184 grams Bis(m-aminophenoxybutyl)tetramethyldisiloxane, 435.2 grams of 1,3,5,7-tetramethyl-1,3,5,7-tetraphenylcyclotetrasiloxane and 22.36 grams 1,3,5,7-tetramethyl-1,3,5,7-tetravinylcyclotetrasiloxane under a nitrogen atmosphere. The reaction mixture was then heated to the boiling point, which was gradually increased to 210° C. over a two hour period. The reaction mixture was maintained at this temperature for 10 hours, then cooled to room temperature and 2 grams sodium bicarbonate were added, with rapid agitation, which was continued for 15 minutes.

The reaction mixture was then filtered and an aliquot of the filtrate, a homogeneous amber fluid was titrated with a 0.01N perchloric acid solution to a bromcresol purple end point. The amount of perchloric acid required was equivalent to 1.84% by weight of amine groups in the product. Based on this value and the amount of starting materials, the formula was calculated.

EXAMPLE XXX

Preparation of the polysiloxane formula

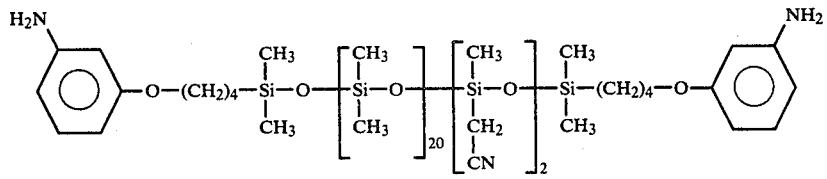

The equilibrated amino functional polysiloxane of the general formula indicated above was prepared by the equilibration of Bis(m-aminophenoxybutyl)tetramethyldisiloxane with octamethylcyclotetrasiloxane and a mixture of cyclic cyanoethylmethylsiloxanes.

Three pellets, equivalent to 0.15 gram of potassium hydroxide, were added under a nitrogen atmosphere to a reaction mixture containing 4.60 grams Bis(m-aminophenoxybutyl)tetramethyldisiloxane, 148 grams octamethylcyclotetrasiloxane, and 22.6 grams of a mixture of cyclic cyanoethylmethylsiloxanes containing from 3 to 10 silicon atoms in the ring. The reaction mixture was heated to the boiling point, which gradually increased to 210° C. over a two hour period. This temperature was maintained for 10 hours, after which the reaction mixture was cooled to ambient temperature. Two grams of ammonium chloride were added and the reaction mixture was stirred rapidly for ½ hour.

The reaction was then filtered and an aliquot of the homogeneous fluid was titrated with a 0.01N perchloric acid solution to a bromcresol purple end point. The amount of perchloric acid required was equivalent to 1.32% by weight of amine groups in the product. Based on this value and the amount of starting materials, the general formula was calculated.

EXAMPLE XXXII

Preparation of the polysiloxane of formula

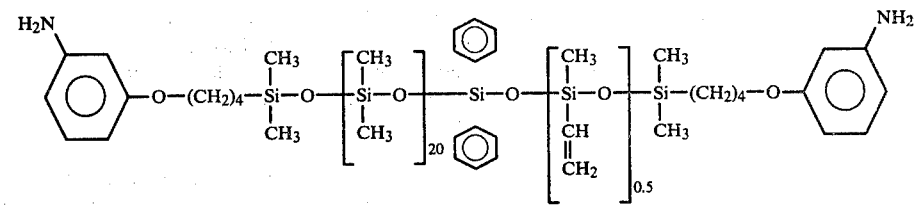

The reaction mixture was then filtered. An aliquot of the filtrate, a homogeneous amber fluid was titrated with a 0.10N perchloric acid solution to a bromcresol purple end point. The amount of perchloric acid required was equivalent to 1.32% by weight of amine groups in the product. Based on this value and the amount of starting materials, the general formula of the product was calculated.

EXAMPLE XXXI

Preparation of the polysiloxane of the formula

The equilibrated amino functional polysiloxane of the general formula indicated above was prepared by the equilibration of Bis(m-aminophenoxybutyl)tetramethyldisiloxane with cyclic vinylmethylsiloxanes, octaphenylcyclotetrasiloxane and octamethylcyclotetrasiloxane.

Two pellets, equivalent to 0.1 gram potassium hydroxide was added to a reaction mixture containing 4.6 grams Bis(m-aminophenoxybutyl)tetramethyldisiloxane, 14.8 grams octamethylcyclotetrasiloxane, 1.98 grams octaphenylcyclotetrasiloxane, and 4.3 grams of a

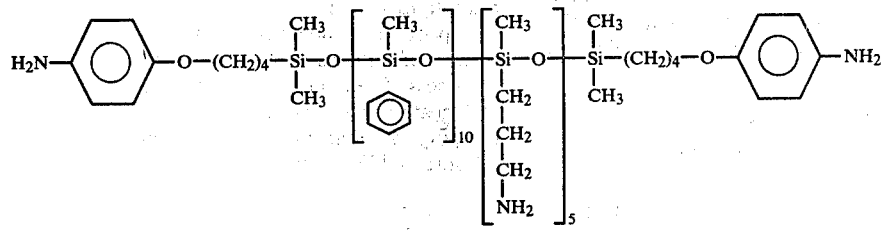

The equilibrated amino functional polysiloxane of the general formula indicated above was prepared by the equilibration of Bis(p-aminophenoxybutyl)tetramethyldisiloxane with 1,3,5,7-tetramethyl-1,3,5,7-tetraphenylcyclotetrasiloxane and cyclic γ-aminopropylmethylsiloxanes.

Two pellets, equivalent to about 0.1 gram, of potassium hydroxide were added under a nitrogen atmosphere to a reaction mixture containing 4.60 grams Bis(p-aminophenoxybutyl)tetramethyldisiloxane, 13.6 grams 1,3,5,7-tetramethyl-1,3,5,7-tetraphenylcyclotetrasiloxane, and 5.8 grams of a mixture of cyclic γ-aminopropylmethylsiloxanes containing from 3 to 10 silicon axoms in the ring. The reaction mixture was heated to the boiling point, which gradually increased to 225° C. over a two hour period. The temperature was maintained for 10 hours, following which the reaction mixture was cooled to ambient temperature. A one-gram portion of sodium bicarbonate was added to the reaction mixture with stirring, which was continued for ½ hour to achieve neutralization of the potassium hydroxide catalyst.

mixture of cyclic vinylmethylsiloxane wherein the number of cyclic siloxane units per molecule was from 3 to 5. The reaction mixture was under a nitrogen atmosphere with constant agitation and was heated to the boiling point, which gradually increased to 215° C. during a two hour period. Heating at this temperature was continued for 8 hours, following which the reaction mixture was cooled to room temperature and ½ cc of concentrated aqueous hydrochloric acid was added. The reaction mixture was then stirred for ½ hour to ensure complete neutralization of the potassium hydroxide catalyst.

The reaction mixture was then filtered. An aliquot portion of the filtrate, a homogeneous amber fluid, was titrated with a 0.01N perchloric acid solution to a bromcresol purple end point. The amount of perchloric acid required was equivalent to 1.43% by weight of amine groups in the product. Based on this value and the amount of starting materials, the general formula was calculated.

EXAMPLE XXXIII

Preparation of the polysiloxane of formula

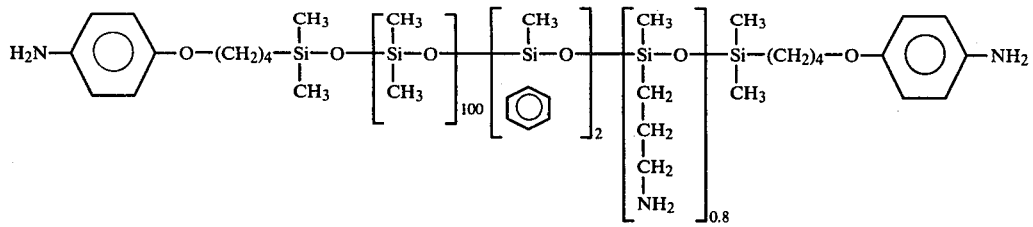

The equilibrated amino functional polysiloxane of the general formula indicated above was prepared by the equilibration of Bis(p-aminophenoxybutyl)tetramethyldisiloxane with octamethylcyclotetrasiloxane, a mixture of cyclic methylphenylsiloxanes, and a mixture of cyclic aminopropylmethylsiloxanes.

A reaction mixture was prepared under a nitrogen atmosphere and with rapid agitation by combining 4.6 gram Bis(p-aminophenoxybutyl)tetramethyldisiloxane, 74 grams octamethylcyclotetrasiloxane, 2.72 grams of a mixture of cyclic methylphenylsiloxanes wherein the number of siloxane units in each ring was from 3 to 10, 9 grams of a mixture of cyclic aminopropylmethylsiloxanes, and 2 pellets, about 0.1 gram, of potassium hydroxide. The resultant mixture was heated at the boiling point for 8 hours and then cooled to room temperature. The potassium hydroxide catalyst was then neutralized by adding 1 gram sodium bicarbonate to the reaction mixture and stirring for ½ hour.

The reaction mixture was then filtered and an aliquot portion of the filtrate, a homogeneous amber fluid, was titrated with a 0.01N perchloric acid solution to a bromcresol purple end point. The amount of perchloric acid required was equivalent to 0.52% by weight of amine groups in the product. Based on this value and the amount of starting material, the general formula was calculated.

EXAMPLE XXXIV

Preparation of the polysiloxane of formula

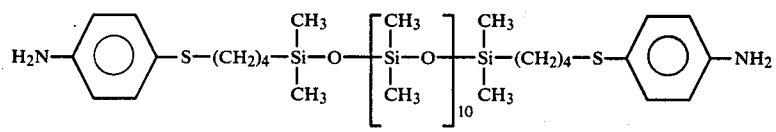

The equilibrated amino functional polysiloxane of the above formula was prepared by the equilibration of Bis(p-aminophenylthiobutyl)tetramethyldisiloxane with methyl tetramer.

A 1cc portion of a solution containing 50ppm tetrabutylphosphonium trimethylsilanolate in methyl tetramer was added to a reaction mixture consisting of 78 grams octamethylcyclotetrasiloxane and 49.2 grams Bis(p-aminophenylthiobutyl)tetramethyldisiloxane under a nitrogen atmosphere. The reaction mixture was heated at 115° C. for 4 hours. During this period of time, the viscosity of the reaction mixture was observed to increase until it reached a relatively constant value. At the end of the 4 hour period, the temperature of the reaction mixture was raised to 160° C. for 2 hours to effect destruction of the catalyst. The reaction mixture was then cooled to room temperature and filtered.

An aliquot portion of the filtrate was titrated with a 0.01N perchloric acid solution to a bromcresol purple end point. The amount of perchloric acid required was equivalent to 2.5% weight of amine groups in the product. Based on this value and the amount of starting material, the general formula for the product was calculated.

EXAMPLE XXXV

Siloxane-containing poly(half-amide) containing 30 mole % siloxane

To a reaction mixture consisting of 54.64 grams 1,3-bis-(p-aminophenoxybutyl)tetramethyldisiloxane and 29.94 grams m-phenylenediamine in 636g dry N-methylpyrrolidone and cooled to 0° C. was added portionwise, over a 4 hour period, 127.05 grams benzophenonetetracarboxylic dianhydride. The solution became dark amber and its viscosity greatly increased toward the latter half of the reaction.

Upon complete anhydride addition, solution was not complete but stirring was maintained for 10 additional hours at ambient temperature. At this time, a dark amber clear viscous solution resulted which wet the sides of the flask well. The product obtained was a siloxane containing poly(half-amide) solution containing 30 mole % of 1,3-bis-(p-aminophenoxybutyl)tetramethyldisiloxane.

A portion of the above solution was disposed on the surface of a glass slide to form a coating about 0.2 mil in thickness. The coated slide was then placed in a furnace and heated to effect curing of the poly(half-amide) to the polyimide, in the following manner:
2 hours at 135° C.±10° C.
2 hours at 185° C.±10° C.
2 hours at 250° C.±10° C.
½hour at 300° C.±10° C.

After curing and upon removal of the coated slide from the furnace, examination of the resulting film was performed. The cured film bonded very tenaciously to the glass slide. The coating still bonded tenaciously to the glass slide even after immersion in boiling water for a period of 6 hours.

The polyimide of this example has proven to be an excellent material for passivation and/or protective coatings for semiconductor devices including application of the material to exposed portions of P-N junctions. Very low leakage current <0.3 microamps has been observed at 0.31 microamps and 2000 volts.

The film of polyimide is capable of withstanding temperatures of the order of about 450° for periods of time up to 1 hour. This physical characteristic allows one to deposit a glass layer by chemical vapor deposition on the cured film of material. The glass layer adheres very well to film. For best results one should attempt to match the coefficient of thermal expansion of the material of the film and the material of the glass.

EXAMPLE XXXVI

Siloxane-containing poly(half-amide) containing 80 mole % of siloxane

Employing the procedure of Example XXXV, 34.56 parts 1,3-bis-(m-aminophenoxypropyl)tetramethyldisiloxane was combined with 3.96 parts methylenedianiline in 180ml anhydrous n-methyl-pyrrolidone. The solution was cooled to 0° C. as 21.8 parts pyromellitic dianhydride was added in portions over a 3 hour period. A dark amber viscous solution resulted. The reaction mixture was then allowed to stand overnight at ambient temperature. The resulting solution was a siloxane-containing poly(half-amide) solution containing 80 mole % of 1,3-bis-(m-aminophenoxypropyl)tetramethyldisiloxane.

A portion of this solution was applied to a selected surface area of several semiconductor devices. Curing of the applied solution was accomplished in the same manner as described in the curing of the applied solution in Example XXXV.

The coated devices were subjected to a corona discharge test of 2500 volts. The coated devices continued to function electrically within the design specification parameters for well over 1,000 hours exposure.

Unprotected semiconductor devices of the same type failed within 10 hours when exposed to the same corona discharge test.

EXAMPLE XXXVII

Siloxane-containing poly(half-amide) containing thio linkage

The procedure of Example XXXV was practiced except that 58.44 grams 1,3-Bis-(p-aminophenylthiobutyl)tetramethyldisiloxane was substituted for the 54.64 grams 1,3-Bis-(p-aminophenoxybutyl)tetramethyldisiloxane.

The product obtained was a siloxane-containing poly(half-amide) solution containing 30 mole % of 1,3-bis(p-aminophenoxythiobutyl)tetramethyldisiloxane.

In addition to the excellent physical properties obtained, which are the same as obtained in Example XXXV, the cured material has excellent antioxidant properties. A coating applied to electrical wire and as thin as 1 millimeter in thickness has proven to be an excellent anti-tracking material and suitable for use in manufacturing the windings required for electric motors and electric generators.

The wire coating may be applied in a continuous operation and only a single application is necessary to meet desired requirements. However, should a thicker coating be required, one method of accomplishing the same is to apply a second coating layer and curing as before, as the material will adhere to itself.

EXAMPLE XXXVIII

Polyimide containing 100 mole % siloxane

A. Bis(p-aminophenoxy propyl) tetramethyldisiloxane

The procedure of Example XXXV was repeated with a reaction mixture of 5.20 parts 2,2-bis{4-(3,4 dicarboxyphenoxy)phenyl}propane dianhydride, 4.60 parts bis(p-aminophenoxypropyl)tetramethyldisiloxane and 0.1 part toluenesulfonic acid in 90 ml of dichlorobenzene and refluxed; the water formed by the reaction was removed azeotropically with the solvent and passed over a solid desiccant which removed the water chemically and the solvent was returned back to the reaction site. When water was no longer evolved, the bath temperature was lowered to 175° C. and the reaction was allowed to continue overnight. The polymeric solution was then cooled and filtered. The filtered polymeric solution was then added to a ten-fold excess of methanol to precipitate the polymer. The polymer was white and fibrous. The precipitated polymer was separated by filtration, washed several times with fresh methanol, and dried overnight in an oven maintained at a temperature of 65° C.

A portion of the polymer was placed in a beaker and sufficient amount of N-methyl-pyrrolidone was added to the polymer to prepare a solution having a 25% solids content. A portion of the solution was applied to the surface of a ceramic plate, which was placed in a preheated oven and maintained at 120° C. for a period of 60 minutes. Upon examination of the coated ceramic after it was removed from the oven, it was discovered that a strong transparent film of about 8 mils in thickness has been formed on the ceramic. The film was bonded tenaciously to the ceramic substrate. The film was resistant to abrasion and could not be peeled off, or stripped from, the substrate in a continuous form.

The coated plate, with the cured film was immersed in the solvent methylene chloride for a period of 30 minutes. Upon removal from the solvent, the film had been removed from the ceramic. That is, the surface of the ceramic plate was completely free of the cured film of polymer material.

B. Bis (p-aminophenoxymethyl) tetramethyldisiloxane

A reaction mixture of 37.6 grams bis(p-aminophenoxymethyl)tetramethyl disiloxane, 32.2 grams benzophenone tetracarboxylic acid dianhydride, and 0.1 grams toluene sulfonic acid in 803 grams trichlorobenzene was heated to reflux; water formed by the reaction removed axeotropically with the solvent and passed over calcium hydride, which removed the water. The solvent was recycled. When water was no longer evolved the reaction mixture, now a clear solution, was stirred for an additional four hours at 216° C. The reaction mixture was then cooled and filtered; the filtered solution was then slowly added to a ten-fold excess of methanol to precipitate the polymer. The polymer was white and fibrous; it was separated by filtration and dried overnight under vacuum in an oven at 60° C.

The polymer was stable to 400° C. temperatures, as determined by thermogravimetric analysis and a film case on glass from a solution of the polymer in N-methylpyrrolidone bonded tenaciously thereto.

C. Bis(p-aminophenoxyoctyl) tetramethyl disiloxane

The procedure of Part B above is repeated, except that the bis(p-aminophenoxymethyl)tetramethyl disiloxane is replaced by 57.2 grams of bis(p-aminophenoxyoctyl)tetramethyl disiloxane.

This polymer is found to be stable to about 300° C. with little weight loss.

EXAMPLE XXXIX

Polyimide containing 30 mole % of siloxane

To a mixture containing 10.4 parts 2,2-bis{4(3,4-dicarboxyphenoxy)phenyl}propane dianhydride (0.02 moles), 2.772 parts methylene dianiline (0.014 mole), and 0.1 part toluenesulfonic acid was added 231 parts o-dichlorobenzene. The reaction mixture was placed in a silicone oil bath maintained at 240° C., resulting in rapid reflux.

The refluxing liquid, incorporating water which was formed in the imidization reaction, was passed over a desiccant, such as calcium hydride, and resulting dichlorobenzene was returned back to the reaction. After a period of 2-4 hours, water was no longer generated as indicated by the clear solution bathing the calcium hydride.

The silicone oil bath temperature was lowered to 200° C., followed by the addition of 2.76 grams 1,3-bis(p-aminophenoxybutyl)tetramethyldisiloxane (0.006 mole). The reaction was maintained at this temperature for four additional hours. Thereafter, the heating bath was removed. The polymeric solution was cooled, filtered and precipitated into a large volume of methanol. The resulting white fibrous polymer was collected by filtration, washed five times with additional fresh methanol, and dried at 5 mm pressure and 65° C. overnight. There was obtained 15.2 grams polymer. To this polymer was added 45.6 parts freshly distilled N-methyl-pyrrolidone and the resulting mixture was stirred until complete solution was obtained.

The resulting solution consisted of a polyimide copolymer material having 30 mole % 1,3-bis-(p-aminophenoxybutyl)tetramethyldisiloxane in N-methyl-pyrrolidone.

A portion of the polyimide in solution was disposed on several glass slides and heated at 125° C. for 2 hours to completely dry the film. The resulting film bonded very tenaciously to the glass slide. Additionally, the film exhibited excellent resistance to abrasion and impact. When subjected to immersion in boiling water for 6 hours, the film remained very tenaciously bonded to the surface of the glass slide.

Several more glass slides were prepared and coated with another portion of the polyimide solution; the film was dried in the same manner as before. The coated slides were weighed to determine the weight of the polyimide applied.

These slides were placed in an air circulating oven and heated to 300° C.±10° C. for a period of 8 hours and then removed from the oven and cooled to ambient temperature.

Upon reweighing the slides, no loss in weight could be detected.

Thus, it is seen that the siloxane containing polyimide of this invention retains its stability in circulating air at high temperature.

EXAMPLE XL

Polyimide containing 30 mole % of prior art siloxane

The procedure of Example XXXIX was repeated except for the addition of 1.65 grams 1,3-bis-(delta-aminobutyl) tetramethyldisiloxane (0.006 mole) to the reaction mixture in place of the addition of 2.76 grams 1,3-bis-(p-aminophenoxybutyl)tetramethyldisiloxane (0.006 mole).

The total weight of the polymer material obtained was 14.3 grams. The polymer was added to 42.9 parts freshly distilled N-methyl-pyrrolidone to make the solution of polyimide for duplicating the tests run with the polyimide solution of Example XXXIX wherein each solution contained 30 mole % of disiloxane material.

The slides prepared with the disiloxane material of this example experienced a weight loss of 10% when heated in the air circulating oven for 8 hours at 300° C.±10° C.

It is believed that the amino alkyl linkage is the source of instability at high temperature. It is believed that free radical degradation of the alkylene chain is occurring at the high temperature and the byproducts such as $H_2$, $CH_2O$, $CO_2$ and the like are escaping from the polymer. Therefore, the loss of weight of the coating material becomes appreciable in the 8 hours exposure to circulating air at 300° C.±10° C.

From experimentation it has been discovered that temperature stability decreases with increasing alkyl siloxane content.

EXAMPLE XLI

Polyimide containing a macrocyclic crown ether chelating agent

To a mixture containing 5.20 parts 2,2-bis{4-(3,4-dicarboxyphenoxy)phenyl}propane dianhydride (0.01 mole) 3.22 parts bis(m-aminophenoxypropyl)tetramethyldisiloxane (0.07 mole), and 0.1 part toluenesulfonic acid was added 231 parts o-dichlorobenzene. The reaction mixture was placed in a silicone oil bath maintained at 240° C. resulting in rapid reflux. The refluxing liquid, incorporating water which was formed in the imidization reaction, was passed over a desiccant, such as calcium hydride, and the resulting dry liquid, dichlorobenzene, was returned back to the reaction. After a period of from 2 to 4 hours, water no longer was generated by the reaction as indicated by the clear solution bathing the calcium hydride.

The silicone oil bath temperature was lowered to 200° C., followed by the addition of 1.17 grams diaminodibenzo 18-crown-6-ether (0.003 mole). The reaction was maintained at this temperature for four additional hours. Thereafter, the heating bath was removed.

The polymeric solution was cooled, filtered and precipitated into a large volume of methanol. The resulting white fibrous polymer was collected by filtration, washed five times with additional fresh methanol, and dried at 5 mm pressure at 65° C. overnight. The weight of polymer material obtained was 9.1 grams. To this amount of polymer was added 27.3 parts freshly distilled N-methyl-pyrrolidone and the resulting mixture was stirred until complete solution was obtained.

A glass slide, a titanium coupon and a copper panel were each coated with a portion of the solution of polyimide by brushing a layer of the solution on a surface of each sample unit. The coated units were placed in a preheated oven maintained at 100° C. for a period of two hours. The units were then removed from the oven and examined. A thin coherent film was formed on the surface of each sample unit and was bonded tenaciously to the respective substrate material. Each film was very resistant to abrasion and remained bonded well to each substrate surface even after exposure to boiling water for a period of two hours. The chelating agent, chemically bonded into the structure of the polymer, did not affect the bonding and abrasion resistance properties of the cured polymer film.

EXAMPLE XLII

Polyimide from benzophenone tetracarboxylic dianhydride and 100 mole % siloxane

To a reaction mixture charged with 46 parts by weight of Bis(p-aminophenoxybutyl)tetramethyldisiloxane and 32.3 parts by weight benzophenone tetracarboxylic dianhydride in 975 parts by weight of dichlorobenzene was added 1 part by weight methane sulfonic acid. The reaction material was heated to reflux and the water formed by the resulting chemical reaction was removed azeotropically and eliminated in a CaH2 tower. When water was no longer evolved, the reaction material was kept at reflux for an additional 8 hours. The reaction material was then cooled to room temperature and poured into 2 gallons of methanol to produce a yellow powder material.

The yellow powder material was collected by filtration, washed free of solvent with additional methanol and dried.

A 25% solids solution was prepared by using an appropriate amount of N-methyl-pyrrolidone. A portion of the solution was applied to the surface of a glass slide and dried by heating at 120° C.±5° C. in an air circulating oven. A tough film, having a deep yellow coloration, was produced which bonded tenaciously to the surface of the glass slide.

EXAMPLE XLIII

Polyimide from benzophenone tetracarboxylic dianhydride, siloxane and diamine

The process of Example XLII was repeated except that the reaction mixture included only 39.1 parts by weight Bis(p-aminophenoxybutyl)tetramethyldisiloxane and additionally 1.62 parts by weight of m-phenylene diamine. Complete solution occurred in 3 hours.

Upon drying, a deep yellow film was again formed on the surface of the glass slide. The film was bonded tenaciously to the surface of the glass slide.

Chemical analysis of the reaction product material proved it to be a siloxane-containing polyimide copolymer material having a high Tg property. The deep yellow color of the material is advantageous to those using the material as one is able to see where the material is applied to a surface. Upon drying, the resultant film is solvent resistant and exhibits excellent adhesion to the surface to which it is applied as well as to its own exposed surface so as to produce thick films by multiple solution applications and drying cycles.

EXAMPLE XLIV

Polyimide from Pyromellitic tetracarboxylic dianhydride and 100 mole % siloxane

To a reaction mixture charged with 21.8 parts by weight of pyromellitic tetracarboxylic acid dianhydride, 46 parts by weight of bis-(p-amino-phenoxybutyl)tetramethyldisiloxane and 971 parts by weight of trichlorobenzene was added 1 part by weight toluenesulfonic acid. The reaction material was heated to reflux and the water formed by the resulting chemical reaction was removed azeotropically and eliminated in a CaH2 tower. When water was no longer evolved, a period of about 4 hours thereafter, the reaction temperature was dropped to 215° C. and maintained thereat overnight. The reaction material was then cooled to room temperature, filtered and poured into 5 gallons of methanol to produce a deep yellow powder material.

The deep yellow powder material was collected by filtration, washed free of solvent with additional methanol and dried.

A 25% solids solution was prepared by using an appropriate amount of N-methyl-pyrrolidone. A portion of the solution was applied to the surface of a glass slide and dried by heating at 120° C.±5° C. in an air circulating oven. A tough film, having a deep yellow coloration, was produced which bonded tenaciously to the surface of the glass slide.

EXAMPLE XLV

Polyimide from thio-siloxane containing 100 mole % siloxane

The procedure of Example XLII was repeated except that the reaction mixture was 49.2 parts by weight Bis-(m-aminophenylthiobutyl)tetramethyldisiloxane, 32.2 parts by weight benzophenone tetracarboxylic acid dianhydride (BTDA), 1 part by weight toluenesulfonic acid and 1300 parts by weight trichlorobenzene. Reflux temperature was 218° C. Water formed by the reaction was removed azeotropically by absorption on a 3A molecular sieve. Overnight reaction temperature after all water was removed was 200° C.

The reaction product was recovered in the same manner as a deep yellow powder. Make up and testing was performed in the same manner as before and proved the product to make a tough film which bonded tenaciously to the surface of the glass slide.

EXAMPLE XLVI

Polyimide containing 50 mole % siloxane and 50 mole % diamine

To a reaction mixture consisting of 7.67 grams (0.02883459) mole 5(6) amino-1-(4'-aminophenyl)-1,3,3 trimethylindane, 13.26 grams (0.02883459) mole Bis(m-aminophenoxybutyl)tetramethyldisiloxane, and 18.57 grams (0.05766917) mole benzophenone tetracarboxylic acid dianhydride was added a catalytic quantity, 0.5 grams toluene sulfonic acid followed by 453 grams trichlorobenzene. The reaction mixture was heated to reflux temperature of 218° C. The solvent and water produced by the chemical reaction were passed over a calcium hydride bed to eliminate water and produce a dry reaction mixture. The system was maintained at refluxing temperature until water was no longer being generated, a period of approximately 3 hours. The reaction mixture was then maintained at refluxing temperature overnight.

The reacted reaction mixture was then cooled to room temperature and filtered. No solids were present. The filtered reacted reaction mixture was then poured into 1 gallon of methanol to precipitate a stringy polymer material.

The resulting polymer was very soluble in methylene chloride, N-methyl-pyrrolidone (NMP), and dimethylformamide (DMF).

A sample of the polyimide was dissolved in N-methyl-pyrrolidone and the solids content of the polyimide therein was 25% by weight. A portion of the solution was disposed on the surface of a glass slide to form a coating about 0.2 mil in thickness. The coated slide was then placed in an air circulating oven for 1 hour at 110° C.±5° C. The slide was removed from the oven, cooled to room temperature and examined.

The film was transparent and bonded extremely well to the surface of the glass slide.

EXAMPLE XLVII

Polyimide containing 90 mole % siloxane and 10 mole % diamine

The process of Example XLVI was repeated except that the reaction mixture in the reactor was as follows:
- 32.2 grams (0.1 mole) benzophenone tetracarboxylic acid dianhydride
- 41.4 grams (0.09 mole) Bis(p-aminophenoxybutyl)tetramethyldisiloxane
- 2.66 grams (0.01 mole) 5(6) amino-1-(4'-aminophenyl)-1,3,3-trimethylindane
- 0.5 grams methane sulfonic acid
- 877 grams trichlorobenzene The resulting polymer product was again stringy in nature.

When applied to a glass slide in the form of a solution and heated to evaporate the solvent, the resulting film was translucent and bonded very well to the glass slide.

EXAMPLE XLVIII

Polyimide containing 30 mole % disiloxane and 70 mole % diamine

The process of Example XLVI was repeated except that the reaction mixture in the reactor was as follows:
- 52 grams 4,4' Bisphenol A ether dianhydride (2,2-Bis{4-(3,4-dicarboxyphenoxy)phenyl}propane dianhydride), (0.1 mole).
- 13.8 grams Bis(m-aminophenoxybutyl)tetramethyldisiloxane (0.03 mole).
- 18.62 grams 5(6) amino-1-(4'-aminophenyl)-1,3,3 trimethylindane (0.07 mole).
- 1 gram toluene sulfonic acid
- 971 grams dichlorobenzene The resulting polymer product was again stringy in nature. When applied to a glass slide in the form of a solution and heated to evaporate the solvent, the resulting film was translucent and bonded very well to a glass slide.

EXAMPLE XLIX

Polyimide containing 20 mole % siloxane and 80 mole % diamine

The process of Example XLVI was repeated except that the reaction mixture in the reactor was as follows:
- 16.1 grams benzophenone tetracarboxylic acid dianhydride (0.05 mole).
- 10.64 grams 5(6) amino-1-(4'-aminophenyl)-1,3,3 trimethylindane (0.04 mole).
- 4.6 grams Bis(p-aminophenoxybutyl) tetramethyldisiloxane (0.01 mole).
- 0.5 gram toluene sulfonic acid
- 361 grams dichlorobenzene The resulting polymer product was stringy in nature. When applied to a glass slide in the form of a solution and heated to evaporate the solvent, the resulting film was translucent and bonded very well to the glass slide.

EXAMPLE L

Polyimide containing 85 mole % siloxane and 15 mole % diamine

The process of Example XLVI was repeated except that the reaction mixture in the reactor was as follows:
- 52 grams 3,3' Bis-phenol A dianhydride, 2,2-Bis{4-(2,3-dicarboxyphenoxy)phenyl}propane dianhydride, (0.1 mole).
- 391. grams Bis-(m-aminophenoxybutyl)tetramethyldisiloxane (10.035 mole).
- 1 gram toluene sulfonic acid
- 1092 grams dichlorobenzene.

The oil bath temperature for the reaction was maintained at ~200° C. When the water of reaction had been completely evolved, 3.99 grams of 5(6) amino-1-(4'-aminophenyl)-1,3,3-trimethylindane (0.015 mole) was added to the reaction mixture. The reaction process was then contained overnight and evaluated as described in Example XLVI.

The resulting polymer product was stringy in nature. When applied to a glass slide in the form of a solution and heated to evaporate the solvent, the resulting film was again translucent and bonded very well to the glass slide.

EXAMPLE LI

Polyimide containing 70 mole % siloxane and 30 mole % diamine

To a mixture containing 10.4 parts 2,2-bis{4(3,4-dicarboxyphenoxy)phenyl}propane dianhydride (0.02 moles), 0.648 parts m-phenylene diamine (0.006 mole), and 0.1 part toluenesulfonic acid was added 231 parts o-dichlorobenzene. The reaction mixture was placed in a silicone oil bath maintained at 240° C. resulting in rapid reflux.

The refluxing liquid, incorporating water which was formed in the imidization reaction, was passed over a desiccant, such as calcium hydride, and resulting dry dichlorobenzene was returned back to the reaction. After a period of 2-4 hours, water was no longer generated as indicated by the clear solution bathing the calcium hydride.

The silicone oil bath temperature was lowered to 200° C., followed by the addition of 6.44 grams 1,3-bis-(p-aminophenoxybutyl)tetramethyldisiloxane (0.014 mole). The reaction was maintained at this temperature for four additional hours. Thereafter, the heating bath was removed. The polymeric solution was cooled, filtered and precipitated into a large volume of methanol. The resulting white fibrous polymer was collected by filtration, washed five times with additional fresh methanol, and dried at 5 mm pressure and 65 C. overnight. There was obtained 15.2 grams polymer. To this polymer was added 45.6 parts freshly distilled diglyme and the resulting mixture was stirred until complete solution was obtained.

The resulting solution consisted of a polyimide having 70 mole % 1,3-bis-(p-aminophenoxybutyl)tetramethyldisiloxane in diglyme.

A portion of the polyimide in solution was disposed on several glass slides and heated at 85° C. for 2 hours to evaporate the solvent. The resulting film bonded very tenaciously to the glass slide. Additionally, the film exhibited excellent resistance to abrasion and impact. When subjected to immersion in boiling water for 6 hours, the film remained very tenaciously bonded to the surface of the glass slide.

Several more glass slides were prepared and coated with another portion of the polyimide solution and dried in the same manner as before. The coated slides were weighed to determine the weight of the material applied.

The preweighed slides were placed in an air circulating oven and heated to 300° C.±10° C. for a period of 8 hours and then removed from the oven and cooled to ambient temperature.

Upon reweighing the slides, no loss in weight could be detected.

It is believed that the aryl ether portion of the polymer inhibits free radical degradation. In other words, it is a free radical scavenger inhibiting destruction by a radical propagation reaction. Therefore, no appreciable weight loss could be detected on weighing the coated slide after the exposure to 300° C. for 8 hours.

EXAMPLE LII

Polyimide containing 30 mole % of functional group

2,4-diaminoacetanilide, m.p.161-163 C., was prepared by the catalytic reduction of 2,4-dinitro acetanilide.

To a mixture containing 26 parts 2,2-bis{4(3,3-dicarboxyphenoxy)phenyl}propane dianhydride (0.05 moles), 3.78 parts m-phenylene diamine (0.035 mole), and 0.1 part toluenesulfonic acid was added 231 parts o-dichlorobenzene. The reaction mixture was placed in a silicone oil bath maintained at 240° C. resulting in rapid reflux.

The refluxing liquid, containing water formed in the reaction, was passed over a desiccant, such as calcium hydride, and the resulting dry dichlorobenzene was returned back to the reaction. After a period of 2–4 hours, water was no longer generated as indicated by the clear solution bathing the calcium hydride.

The silicone oil bath temperature was lowered to 200° C., followed by the addition of 2.48 grams 2,4-diaminoacetanilide (0.015). The reaction was maintained at this temperature for four additional hours. Thereafter, the heating bath was removed. The polymeric solution was cooled, filtered and precipitated into a large volume of methanol. The resulting white fibrous polymer was collected by filtration, washed five times with additional fresh methanol, and dried at 5 mm pressure and 65° C. overnight. There was obtained 29.3 grams polymer. To this polymer was added 87.9 parts freshly distilled N-methyl-pyrrolidone and the resulting mixture was stirred until complete solution was obtained.

The resulting solution consisted of a polyimide having 30 mole percent 2,4-diaminoacetanilide in N-methylpyrrolidone.

EXAMPLE LIII

Polyimide containing 30 mole % of functional group—COOH

The procedure of Example LII was repeated except that 2.28 grams of 3,5-diaminobenzoic acid (0.015 mole) was used in place of the 0.015 moles of diaminoacetanilide.

There was obtained 30.1 grams polymer. To this polymer was added 90.3 parts freshly distilled N-methylpyrrolidone and the resulting mixture was stirred until complete solution was obtained.

The resulting solution consisted of a polyimide having 30 mole percent 3,5 diaminobenzoic acid in N-methyl-pyrrolidone.

EXAMPLE LIV

Polyimide containing 50 mole % functional group—substituted phenoxy p-(2,4-diaminophenoxy) acetanilide was obtained by the condensation of sodium 4-acetamidophenolate with 2,4-dinitro chlorobenzene and was catalytically hydrogenated to the corresponding diamine m.p. 144°-145° C.

To a mixture containing 15.6 parts 2,2-bis{4(3,4-dicarboxyphenoxy)phenyl}propane dianhydride (0.03 moles), 2.97 parts methylene dianiline (0.015 mole), and 0.1 part toluenesulfonic acid was added 231 parts O-dichlorobenzene. The reaction mixture was placed in a silicone oil bath maintained at 240° C. resulting in rapid reflux.

The silicone oil bath temperature was lowered to 200° C., followed by the addition of 3.86 grams p-(2,4-diaminophenoxy)acetanilide (0.015 mole). The reaction was maintained at this temperature for four additional hours. Thereafter, the heating bath was removed. The polymeric solution was cooled, filtered and precipitated into a large volume of methanol. The resulting white fibrous polymer was collected by filtration, washed five times with additional fresh methanol and dried at 5 mm pressure and 65° C. overnight. There was obtained 21.9 grams polymer. To this polymer was added 66 parts freshly distilled N-methyl-pyrrolidone and the resulting mixture was stirred until complete solution was obtained.

The resulting solution consisted of a polyimide having 50 mole % p(2,4-diaminophenoxy)acetanilide in N-methyl-pyrrolidone.

EXAMPLE LV

Polyimide containing 25 mole % of functional group—SH

To a mixture containing 10.4 parts 2,2-bis{4(3,4-dicarboxyphenoxy)phenyl}propane dianhydride (0.02 moles), 6.9 grams Bis(m-aminophenoxybutyl)tetramethyldisiloxane (0.15 mole), and 0.1 part toluenesulfonic acid was added 231 parts o-dichlorobenzene. The reaction mixture was placed in a silicone oil bath maintained at 240° C. resulting in rapid reflux.

The refluxing liquid, containing water which was formed in the reaction, was passed over a desiccant, calcium hydride, and resulting dry dichlorobenzene was returned back to the reaction. After a period of 2-4 hours, water was no longer generated as indicated by the clear solution bathing the calcium hydride.

The silicone oil bath temperature was lowered to 200° C., followed by the addition of 0.70 grams 2,4-diaminothiophenol (0.005 mole). The reaction was maintained at this temperature for four additional hours. Thereafter, the heating bath was removed. The polymeric solution was cooled, filtered and precipitated into a large volume of methanol. The resulting white fibrous polymer was collected by filtration, washed five times with additional fresh methanol and dried at 5 mm pressure and 65° C. overnight. There was obtained 17.1 grams polymer. To this polymer was added 61 parts freshly distilled N-methyl-pyrrolidone and the resulting mixture was stirred until complete solution was obtained.

The resulting solution consisted of a polyimide having 25 mole percent 2,4-diaminothiophenol in N-methyl-pyrrolidone.

A portion of the solution was disposed on several glass slides and heated at 125° C. for 2 hours to evaporate the solvent. The resulting film bonded very tenaciously to the glass slide. Additionally, the film exhibited excellent resistance to abrasion and impact. When subjected to immersion in boiling water for 6 hours, the film remained very tenaciously bonded to the surface of the glass slide.

Several more glass slides were prepared and coated with another portion of the solution and heated in the same manner as before. The coated slides were weighed to determine the weight of the material applied.

The preweighed slides were placed in an air circulating oven and heated to 300° C.±10° C. for a period of 8 hours and then removed from the oven and cooled to ambient temperature.

Upon reweighing the slides, no loss in weight could be detected.

EXAMPLE LVI

Crosslinking of polyimide polymers

The polyimides of Examples LII and LIII were each dissolved in N-methyl-pyrrolidone to form a 20 weight % solution. The two solutions were combined and mixed to form a homogeneous solution and the solvent was stripped by heating at 120° C.±5° C. in an oven. A portion of the blend obtained was heated in an oven at 300° C.±10° C. for three hours.

The odor of acetic acid could be detected during the early part of the heating cycle. The heated polymer blend was then cooled to room temperature and was placed in NMP but did not dissolve therein when stirred and heated to several hundred degrees Celsius.

A portion of the uncured polymer blend, dissolved readily in N-methyl-pyrrolidone.

The experimental results indicated that the original polymer blend was still soluble in NMP, but crosslinking occurred at the higher temperature range to produce an intractable polymer material.

EXAMPLE LVII

Photosensitive polyimide

A hydroxyl-functional polyimide was prepared having the following composition:
  60 mole percent m-phenylene diamine
  40 mole percent 2,4-diaminophenol
  100 mole percent 2,2-bis{4(3,4-dicarboxyphenoxy)-phenyl}propane dianhydride Employing standard chemical process techniques, p-azidocinnamuyl chloride was prepared by first oxidizing p-nitrotoluene to p-nitrobenzaldehyde. The p-nitrobenzaldehyde was then condensed with malonic acid, reduced with iron powder and hydrochloric acid to form p-aminocinnamic acid. Following diazotization and treatment with sodium azide, the p-aminocinnamic acid was converted to p-azidocinnamil acid which was then converted to the acid chloride with thionyl chlordie.

A solution of 20% by weight of the hydroxyl-functional polyimide in chloroform was prepared.

To the homogeneous solution was added triethylamine in an amount equivalent to the stoichemetric amount of the phenolic content of the polyimide. A solution of p-azio-docinnamyl chloride in chloroform was prepared and added dropwise to exactly equivalent amounts of the polyimide, based upon the phenolic content thereof. A chemical reaction occurred immediately, producing the modified polymer and triethylamine hydrochloride.

The salts were removed by filtration. The chloroform was removed from the solution by flash evaporation at a reduced pressure.

The resulting polymer proved to be a very photosensitive material. The minimum light energy required for cross-linking of the polymer materials to make it intractable was less than 500 ergs per square centimeter at 316 mμ.

Cross-linking occurred by the release of molecular nitrogen and the formation of highly reactive nitrine intermediates, which then cross-link.

Other photosensitizers such, for example, as 5-nitroaccennaphthene, 2-nitroflurene, and the like, may also be present in the polyimide to enhance the susceptibility of the exposed polyimide to becoming intractable at low levels of energy exposure.

EXAMPLE LVIII

Microbicidal Polyimide

A mercapto-functional polyimide was prepared having the following composition:
  50 mole % m-phenylene diamine
  50 mole % 2,4-diaminothiophenol
  100 mole % 2,2-bis{4(3,4-dicarboxyphenoxy) phenyl} propane dianhydride A solution of 20 weight percent of this polyimide in chloroform was prepared.

Employing standard chemical reactions, the 2,4-diaminothiophenol was prepared by first reacting sodium hydrosulfide with 2,4-dinitrochlorobenzene to produce 2,4-dinitrophenylmercaptan. The 2,4-dinitrophenylmercaptan was reduced with zinc and hydrochloric acid to produce 2,4-diamino-thiophenol.

A solution of two equivalents of tributyl tin methoxide in chloroform was prepared based upon the mercaptan equivalent weights and added dropwise to the homogeneous polymer solution. An exothermic reaction occurred. Upon completion of the reaction, the chloroform was stripped from the reacted solution by flash evaporation under reduced pressure resulting in a polymer material containing tin.

The structural composition of the polymer was confirmed by standard I.R. and N.M.R.

The resulting polymer has tin in the fundamental sites and is useful for imparting antifouling properties to paints, and for other microbicidal applications.

EXAMPLE LIX

Polyimide containing flame-retardant functional organophosphate

To a mixture containing 10.4 parts 2,2-bis{4(3,4-dicarboxyphenoxy)phenyl} propane dianhydride (0.02 moles), 1.62 parts m-phenylene diamine (0.015 mole), and 0.1 part toluenesulfonic acid was added 231 parts o-dichlorobenzene. The reaction mixture was placed in a silicone oil bath maintained at 240° C. resulting in rapid reflux.

The refluxing liquid, incorporating water which was formed in the imidization reaction, was passed over a disiccant, such as calcium hydride, and resulting dichlorobenzene was returned back to the reaction. After a period of 2-4 hours, water was no longer generated as indicated by the clear solution bathing the calcium hydride.

The silicon oil bath temperature was lowered to 200° C., followed by the addition of 1.70 grams bis(p-aminophenyl)phenyl phosphate (0.005 mole). The reaction was maintained at this temperature for four additional hours. Thereafter, the heating bath was removed. The polymeric solution was cooled, filtered and precipitated into a large volume of methanol. The resulting white fibrous polymer was collected by filtration, washed five times with additional fresh methanol, and dried at 5 mm pressure and 65° C. overnight. There was obtained 13.2 parts polymer. To this polymer was added 39.6 parts freshly distilled N-methyl-pyrrolidone and the resulting mixture was stirred until complete solution was obtained.

The resulting solution consisted of a polyimide having 25 mole % Bis(p-aminophenyl)phenyl phosphate in N-methyl-pyrrolidone.

A portion of this solution was disposed on several glass slides and heated at 125° C. for 2 hours to evaporate the solvent. The resulting film bonded very tenaciously to the glass slide. Additionally, the film exhibited excellent resistance to abrasion and impact. When subjected to immersion in boiling water for 6 hours, the film remained very tenaciously bonded to the surface of the glass slide.

Several more glass slides were coated as before. The coated slides were weighed to determine the weight of the material applied.

The preweighed slides were placed in an air circulating oven and heated to 300° C.±10° C. for a period of 8 hours and then removed from the oven and cooled to ambient temperature.

Upon reweighing the slides, no loss in weight could be detected.

A sample of the above polymer was molded. The molded sample was placed in the flame of a bunsen burner. Upon heating, the molded sample became incandescent and appeared to burn. However, upon removal from the bunsen burner flame, the molded sample stopped glowing, illustrating the inherent flame retardency property of the polymer material.

EXAMPLE LX
Preparation of polyimides from bis(amino)disiloxane and bis{4,4'-di(3,4-dicarboxyphenoxy)phenyl} sulfide dianhydride A. A reaction mixture of 5.10 grams of bis{4,4'-di(3,4-dicarboxyphenoxy)phenyl} sulfide dianhydride, 1.02 grams of 1,4-bis(3-aminophenoxy)benzene, 2.99 grams of bis(m-aminophenoxybutyl) tetramethyl disiloxane, 0.1 grams p-toluene sulfonic acid and 104 grams dichlorobenzene was heated to reflux; water was removed azeotropically and reacted with calcium hydride. When no more water was evolved the mixture was heated at 170° C. for six hours more. The reaction mixture was cooled, filtered and slowly added to excess methanol. A white fibrous polymer precipitated; it was recovered and dried overnight at 65° C. under vacuum.

The polymer was soluble in N-methylpyrrolidone and exhibited no weight loss at 400° C., as determined by thermogravimetric analysis. A film cast on glass adhered tenaciously.

B. The reaction of Part A above was repeated using 4.60 grams of 1,3-bis(m-aminophenoxybutyl)tetramethyl disiloxane as the sole amine component.

The white fibrous polymer recovered was thermally stable and more soluble than the polymer of Part A.

C. Preparation of Bis-[4,4'-di(3,4-dicarboxyphenoxy)phenyl]sulfide dianhydride A glass reactor is charged, under nitrogen, with
4,4'-thiobisphenol: 52.93 grams
50% NaOH solution: 38.8 grams
toluene: 250 ml
dimethylsulfoxide: 250 ml
and heated to reflux under nitrogen with agitation.

Water present in the system and water formed during reaction are removed azeotropically and collected in a Dean Stark trap. When the reaction mixture is completely anhydrous and no more water is being generated, the reaction temperature is lowered to 65° C.; at that point 100 grams of 4-nitro-N-methyl phthalimide are added, all at once. The mixture is stirred at 65° C. for about six hours, filtered hot and allowed to stand at room temperature. The bis-imide crystallizes out on standing; it is filtered and dried. The bis-imide is converted to the tetraacid as follows:

A mixture of 1 part of the bis-imide, 1 part of 50% NaOH solution and 2 parts $H_2O$ is heated to reflux and held until all the methylamine evolves. A clean solution results. This solution is acidified strongly; a white oil separates. Heating this mixture to reflux causes the oil to solidify; it is collected by filtration.

The tetraacid is cyclized by heating in a mixture of glacial acetic acid-acetic anhydride until a clear solution results; upon cooling the anhydride crystallizes out and is collected and dried.

EXAMPLE LXI

A. Preparation of siloxane-containing dianhydride of formula

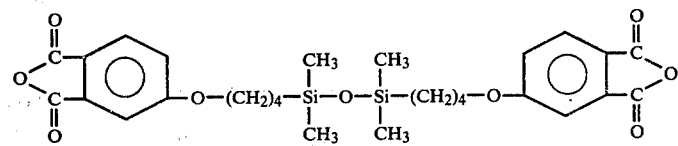

The procedure of Example XV is repeated using 74 grams of 3,4-xylenol in place of the p-bromophenol. The product, bis(3,4-xylenyl oxybutyl)tetramethyl disiloxane is oxidized as follows:

A solution of 48.6 grams of bis(3,4-xylenyloxybutyl)-tetramethyl disiloxane, 400 ml. pyridine and 110 ml. water is heated to 94° C. Heating continued to reflux and 190 grams of potassium permanganate were added slowly over one hour. Each incremental addition followed disappearance of the purple color. As the reaction proceeded, a black precipitate of $MnO_2$ formed. Upon complete permanganate addition, the reaction mixture was maintained at 98°–110° C. for an additional hour. At that time, the purple color was discharged by addition of 10 ml. methanol. The mixture was filtered and the filtrate washed with hot water. The remaining solution was evaporated to dryness; the solids were dissolved in 200 ml. water and to this solution was added concentrated HCl to pH 1. A white precipitate formed. It was collected and dried.

The product was cyclized to the dianhydride by dissolving it in a solution of 100 ml. acetic acid, 100 ml. toluene and 50 ml. acetic anhydride, and heating to reflux. Upon stripping the solvent, the dianhydride was recovered as an oil. The structure was confirmed by analysis (IR and NMR).

B. Preparation of siloxane-containing polyimide

1. A reaction mixture containing 5.7 grams of the anhydride of part A above and 1.08 grams of m-phenylene diamine in 80.5 grams of trichlorobenzene and 0.1 gram of p-toluene sulfonic acid was heated to reflux until all water was azeotropically removed; the system was refluxed for three hours more at 216° C. The mixture was cooled, filtered and poured into excess methanol to precipitate the polymer, which was white and fibrous. The polymer was recovered and dried. It exhibited high thermal stability.

2. The reaction of part 1 above was repeated, except that the m-phenylene diamine was replaced by 4.6 parts of 1,3-bis(m-aminophenoxy-butyl)tetramethyl disiloxane.

The polymer was worked up, recovered from methanol and dried overnight at 50° C. under vacuum. The polymer was stable to 400° C.

EXAMPLE LXII

A. Preparation of siloxane-containing diether dianhydride of formula

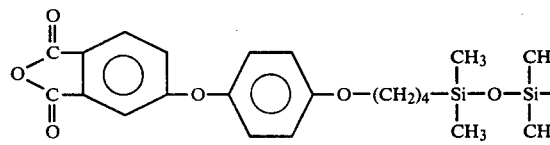

1. Preparation of bis{4-(3',4'-xylenoxy)phenoxybutyl-}tetramethyl disiloxane.

This intermediate is prepared by an Ullman Reaction between the sodium salt of 3,4-xylenol and 1,3-bis(p-bromophenoxybutyl)tetramethyl disiloxane, whose preparation is described in Example XV, in the melt stage, about 140 C., using a copper catalyst. Purification is achieved via molecular distillation.

2. Oxidation and cyclization

The product of Part 1 above is oxidized in a pyridine-water mixture with a five-fold excess of potassium permagnate, followed by neutralization and cyclization, all as described in Example LXI. The structure of the white solid obtained is confirmed by instrumental analysis (IR and NMR) and caustic titration to be bis{4-(3',4'-dicarboxyphenoxy)phenoxybutyl} tetramethyldisiloxane dianhydride.

B. Preparation of polyimide containing siloxane unit

A mixture of 7.54 parts by weight of the dianhydride prepared in Part A above, 1.98 parts by weight of methylene dianiline, 0.1 part of p-toluene sulfonic acid and 100 parts of dichlorobenzene are combined and refluxed; water is removed azeotropically with the solvent and passed over calcium hydride to eliminate the water. The solvent is recycled. When water no longer forms, the mixture is refluxed for an additional four hours. The reaction mixture is cooled, filtered and slowly poured into excess methanol.

The polymer precipitates and is recovered at 60° C.

The polyimide displays stability to temperatures of 425° C.

EXAMPLE LXIII

Melt polymerization of siloxane-containing polyimide 45 grams of equilibrated polysiloxane of formula

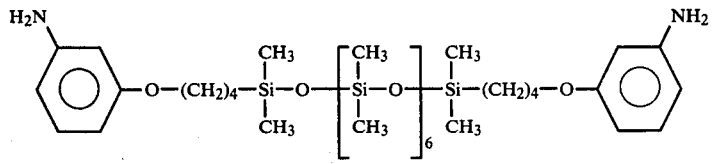

prepared as described in Example XXXIV and containing 3.094% $NH_2$, as determined by perchloric acid titration, is carefully mixed with 14 grams of benzophenone tetracarboxylic acid dianhydride in a Breybender mixer and brought to 300° C. at a heating rate of 20° C. per minute. When the reaction chamber reaches 300° C., the mixture is held at this temperature and agitated for ½ hour and then allowed to cool. The product is scraped from the chamber. It dissolves readily in N-methylpyrrolidone and can be reprecipitated into methanol.

A film cast onto a glass slide displays toughness and excellent adhesion. Molecular weight determination indicates $\overline{MW} = 60,000$. The polyimide displays stability to temperatures of 400° C.

EXAMPLE LXIV

Preparation of epoxy-functional siloxane of formula

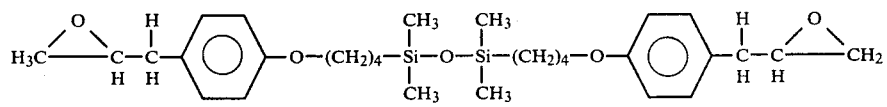

Two moles of 2-alkyphenol sodium salt are coupled with 1 mole of bis (chlorobutyl) tetramethyldisiloxane in a solvent mixture of toluene-dimethylsulfoxide at about 70° C. to form an isomeric mixture of bis (2-propenyl-phenoxybutyl)tetramethyldisiloxane; the structure is confirmed analytically.

The product is epoxidized with m-chloroperbenzoic acid in chloroform solvent. The reaction mixture is initially clear and the reaction mildly exothermic. As the reaction proceeds, m-chlorobenzoic acid is precipitated from solution. The reaction is monitored by gas chromatography; when the reaction is complete, the medium is filtered, and dissolved, m-chlorobenzoic acid is washed out with a 10% sodium carbonate solution. The organic layer is dried, filtered and solvent stripped; the product is recovered by distillation. It has a molecular weight of 542 and an epoxy content of 0.37.

27 grams of the above epoxide are placed in a vessel heated by an oil bath to 120° C. 15 grams of molten phthalic anhydride are added and stirred into the resin. The mixture is held at 120° C. for one hour, at which point it is still soluble in acetone or chloroform. However, heating at 170°-180° C. for two hours effects final cure and a clear, insoluble, somewhat flexible resin is obtained.

EXAMPLE LXV

Crosslinkable Polyimide

The following materials were combined:

|  | grams |
| --- | --- |
| benzophenone tetracarboxylic acid dianhydride | 64.4 |
| bis(m-aminophenoxybutyl)tetramethyl disiloxane | 46.0 |
| m-aminophenylacetylene | 23.4 |
| p-toluene sulfonic acid | 0.1 |
| Trichlorobenzene | 153.0 | and heated to reflux; water formed by the reaction was removed azeotropically with the solvent, which was passed over calcium hydride. Anhydrous solvent was recycled. When water no longer formed, the system was refluxed for an additional six hours. The reaction mixture was cooled, filtered poured into excess methanol, recovered and dried overnight at 60° C. under vacuum.

This polyimide can be processed at temperatures on the order of 100°-120° C. and then crosslinked at 325° C. A 25% solution of the polyimide in N-methylpyrrolidone was prepared; films were cast from this solution onto glass slides. Slides were heated to 120° C. and held at that temperature for 30 minutes. When these slides are placed in boiling N-methylpyrrolidone, the polyimide is completely dissolved in about 3 minutes.

Other slides are exposed to 325° C. for five minutes; the appearance of the film changes perceptably from opaque to clear. When these slides are immersed in boiling N-methylpyrrolidone, no effect is perceived after 24 hours of exposure.

In another embodiment of a cross-linkable polyimide, acetylenic functionality can be introduced in the form of a chain-stopper, by including in the polyimide reaction mixture monoamino acetylene or ethynylphthalic anhydride; there is obtained a polyimide that can be processed at 100°-120° C. and crosslinked at elevated temperatures.

EXAMPLE LXVI

Curing epoxy resins with bis(amino)siloxanes

Two portions, each containing 5 parts by weight of a liquid bisphenol A-epichlorohydrin based epoxy resin (average equivalent weight 190) were prepared. To one portion was added 3 parts by weight of bis(p-aminophenoxybutyl) tetramethyl disiloxane and to the other portion was added 3 parts by weight of bis(m-aminophenoxybutyl) tetramethyl disiloxane. The compositions were each thoroughly mixed and heated to effect curing. Both portions were cured and each yielded a highly flexible, cured epoxy resin with good thermal and electrical properties.

A difference in curing rate was noted; the bis(p-amino) disiloxane was more reactive than the bis(m-amino) disiloxane, curing at 125°-130° C. in two hours while the bis(m-amino)disiloxane cured in three hours at 150° C.

EXAMPLE LXVII

Polyimides from ether-containing amines

1. From 1,3-bis(3-aminophenoxy)benzene

The following materials were combined:

|  | gms |
| --- | --- |
| Benzophenone tetracarboxylic dianhydride | 16.1 |
| 1,3-bis(3-aminophenoxy)benzene | 4.38 |
| bis(m-amino)polysiloxane[(1)] | 32.44 |
| trichlorobenzene | 598.0 |

(1) of formula:

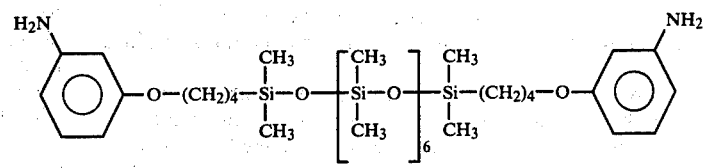

and having 3.452% amine.

The mixture was refluxed; water was removed azeotropically and eliminated via contact with calcium hydride. When water was no longer being generated, the mixture was refluxed for an additional six hours. The mixture was then cooled, filtered and the polyimide recovered by precipitation in methanol. The yellowish fibrous polymer was dried overnight at 60° C. under vacuum.

The polymer was soluble in N-methyl-2-pyrrolidone to the extent that a 25% by weight solution could be prepared. A film cast from this solution onto glass was tough and adhered tenaciously.

2. From 2,2-bis[4-(p-aminophenoxy)phenyl]propane

The reaction of Part 1 was repeated, except that 4.38 grams of 2,2-bis[4-p-aminophenoxy)phenyl]propane were used in place of the 1,3-bis(3-aminophenoxy)benzene.

The yellowish fibrous polyimide recovered was quite soluble in dipolar aprotic solvents and provided tough, adherent films.

3. From 1,3-bis(3-aminophenoxy) benzene and bis(amino) disiloxane

The reaction of Part 1 was repeated, except that 16.1 gms of bis(m-aminophenoxybutyl)tetramethyl disiloxane was used in place of the polysiloxane.

The yellowish, fibrous polyimide recovered was soluble in dipolar aprotic solvents. Films case onto glass, metal and ceramic substrates were tough and adherent.

4. Preparation of 2,2-bis[4-(p-aminophenoxy)phenyl]propane

The following are charged into a 2 liter 3-necked flask under nitrogen atmosphere:
Bisphenol A: 221.4 gms
5% NaOH solution: 155.2 gms
toluene: 500 ml
Dimethylsulfoxide: 500 ml The system is heated to reflux and water is removed azeotropically. After about 6 hours the system is anhydrous and the bis-sodium salt begins to crystallize from solution.

The reaction temperature is dropped to about 70° C. and there is added, all at once, 306 gms of p-chloronitrobenzene; the reaction mixture is maintained at 70° C. overnight. Thereafter, the mixture is cooled and filtered. The toluene is stripped at reduced pressure. Upon cooling, a yellow solid forms; it is recovered by filtration. Analysis confirms the structure to be

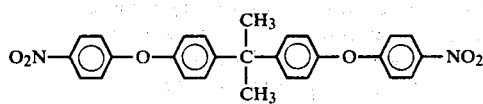

Fifty grams of this intermediate are dissolved in dimethylformamide and to the solution are added 5 gms of Raney nickel. The entire contents are hydrogenated in a Paar hydrogenator at 50 PSI and 80° C. When hydrogen uptake is complete (about 4 hours), the reaction mixture is filtered and poured slowly into a large excess of water. The product is redovered by filtration and recrystallized from a toluene-hexane mixture. Analysis confirms the structure to be

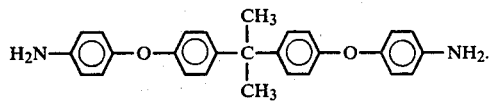

EXAMPLE LXVIII

Preparation of the compound of formula

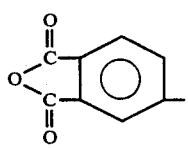

135 grams of 3,4-xylyloxybutyl dimethylchlorosilane and 128 grams of p-tolyloxybutyl dimethylchlorosilane are combined and added dropwise with rapid stirring to a solution of 40 gms NaOH in 1 liter of water. Stirring is terminated upon completion of the addition; two layers appear. The top layer is separated and dried by addition of an equal volume of toluene followed by azeotropic water separation. Finally, the toluene is stripped. The product is analyzed by gas chromatography and three peaks are detected; these correspond to two homo-coupled products and the cross-coupled product. Purification is effected by fractionation, and a clear liquid product is recovered having the structure:

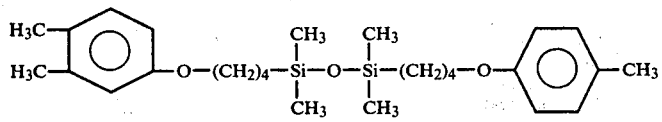

This intermediate is oxidized using a fivefold excess of potassium permanganate equivalence in a 4:1 pyridine:water mixture. Finally, cyclization is effected to form the anhydride. Thus, 50 grams of the triacid are dissolved in a mixture of 100 ml toluene, 100 ml glacial acetic acid and 50 ml acetic anhydride; the mixture is refluxed for two hours. The mixture is then cooled and filtered; the product is dried overnight at 75° C. under vacuum.

What I claim is:

1. An article of manufacture comprising a substrate having disposed thereon a polymeric composition comprising a polyimide, poly(amide-imide) or a poly(halfamide) containing a thermally stable siloxane unit of formula

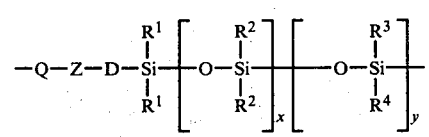

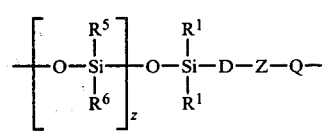

where
Q is a substituted or unsubstituted aromatic group

Z is

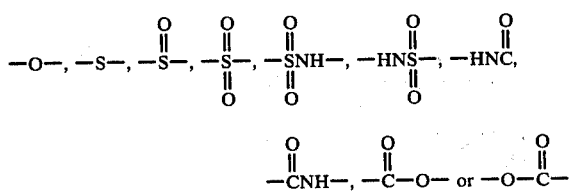

D is unsubstituted or substituted hydrocarbylene;
$R^1$, $R^2$, $R^3$, $R^4$, $R^5$ and $R^6$ each independently is unsubstituted or substituted hydrocarbyl;
x, y and z each independently has a value from 0 to 100.

2. The article of manufacture according to claim 1 in which
Q is substituted or unsubstituted carbocyclic aromatic of 6 to 18 ring carbon atoms or substituted or unsubstituted heterocyclic aromatic of 5 to 18 ring atoms where the hetero atoms are selected from N, O and S, and where the substituents are alkyl of 1 to 12 carbon atoms, alkenyl of 2 to 12 carbon atoms, alkynyl of 2 to 12 carbon atoms, cycloalkyl of 4 to 8 carbon atoms, alkoxy of 1 to 12 carbon atoms, alkylthio of 1 to 12 carbon atoms, phenyl, alkylphenylene having 1 to 12 carbon atoms in the alkyl group, phenoxy, phenylthio, alkylcarbonyloxy of 2 to 12 carbon atoms, phenylalkylene of 1 to 12 carbon atoms in the alkylene group, alkylcarbonyl of 2 to 12 carbon atoms, alkoxycarbonyl of 2 to 12 carbon atoms, bromo, chloro, fluoro, iodo, nitro, cyano, cyanothio, carboxy, carbonyl, hydroxy, mercapto, formyl, thioformyl and mercaptocarbonyl;
D is substituted or unsubstituted hydrocarbylene of 1 or 3 to 18 carbon atoms;
$R^1$, $R^2$, $R^3$, $R^4$, $R^5$ and $R^6$ each independently, is an unsubstituted or substituted alkyl of 1 to 12 carbon atoms, alkenyl of 2 to 12 carbon atoms, alkynyl of 2 to 12 carbon atoms, cycloalkyl of 4 to 8 carbon atoms, phenyl, alkylphenylene where the alkyl group contains 1 to 12 carbon atoms, phenylalkylene where the alkylene group contains 1 to 12 carbon atoms, or alkenylphenylene with 2 to 12 carbon atoms in the alkenyl group and when substituted, these hydrocarbyl groups are substituted by Br, Cl, I, F, —NC, —NO₂, —OCN, alkoxy of 1 to 8 carbon atoms, —S—(C₁-C₈)alkyl,

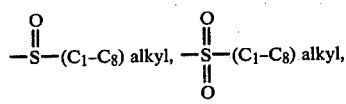

—S—S—(C₁-C₈)alkyl, —COOH, —COSH, —CSOH, —CONH₂, —CN, —CHO, —CHS, —OH, —SH, —NCO and —NR₇R₈ where R₇ and R₈ independently are hydrogen or lower alkyl.

3. The article of manufacture according to claim 2 in which
Q is unsubstituted or substituted carbocyclic aromatic of 6 to 18 ring carbon atoms;
D is branched or linear alkylene of 1 or 3 to 12 carbon atoms; and
x, y and z is each 0.

4. The article of manufacture according to claim 2 in which the siloxane unit has the formula

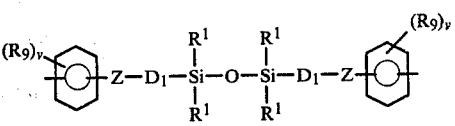

where
v is 0 to 4
$R_9$ is each independently lower alkyl, lower alkenyl, lower alkynyl, cycloalkyl of 4 to 8 carbon atoms, lower alkoxy, lower alkylthio, phenyl, loweralkylphenylene, phenylloweralkylene, loweralkenylphenylene, phenoxy, phenylthio, loweralkylcarbonyl, loweralkylcarbonyloxy, loweralkoxycarbonyl, bromo, chloro, fluoro, iodo, nitro, cyano, cyanothio, carboxyl, carbonyl, hydroxyl, mercapto or mercaptocarbonyl;
Z is

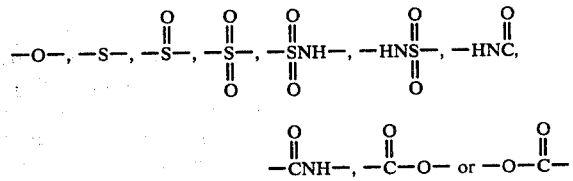

$D_1$ is methylene or alkylene of 3 to 8 carbon atoms;
$R^1$ is lower alkyl, lower alkenyl, lower alkynyl, phenyl, loweralkylphenylene, phenylloweralkylene, or loweralkenylphenylene.

5. The article of manufacture according to claim 4 in which
v is 0 or 1 and
$R^1$ is lower alkyl.

6. The article of manufacture according to claim 4 in which
v is 0 or 1;
Z is —O—;
$R^1$ is lower alkyl.

7. The article of manufacture according to claim 4 in which
v is 0 or 1;
Z is —O—;
$D_1$ is methylene, propylene or butylene;
$R^1$ is alkyl of 1 to 3 carbon atoms.

8. The article of manufacture according to claim 4 in which
v is 0;
Z is —O—;
$D_1$ is methylene or butylene; and
$R^1$ is methyl.

9. The article of manufacture according to claim 2 in which
Q is unsubstituted or substituted carbocyclic aromatic of 6 to 18 ring carbon atoms;
D is branched or linear alkylene of 1 or 3 to 12 carbon atoms;
x has a value from 0 to 100;
y has a value from 0 to 20;
z has a value from 0 to 20.

10. The article of manufacture composition according to claim 9 in which
$R^1$ is unsubstituted hydrocarbyl of 1 to 18 carbon atoms;

$R^2$ is alkyl of 1 to 12 carbon atoms;
$R^3$ is phenyl, alkylphenylene of 7 to 18 carbon atoms, or alkyl of 1 to 12 carbon atoms;
$R^4$ is alkyl of 1 to 12 carbon atoms, phenyl, alkylphenylene of 7 to 18 carbon atoms, or alkenyl of 2 to 12 carbon atoms;
$R^5$ is alkenyl of 2 to 12 carbon atoms, or substituted alkyl of 1 to 12 carbon atoms;
$R^6$ is alkyl of 1 to 12 carbon atoms, phenyl, alkylphenylene of 7 to 18 carbon atoms, or alkenyl of 2 to 12 carbon atoms.

11. The article of manufacture according to claim 10 in which the siloxane unit has the formula $$(R_9)_v - \langle\text{ring}\rangle - Z - D_1 - \underset{R^1}{\overset{R^1}{Si}} - \left[ O - \underset{R^2}{\overset{R^2}{Si}} \right]_x \left[ O - \underset{R^4}{\overset{R^3}{Si}} \right]_y \left[ O - \underset{R^6}{\overset{R^5}{Si}} \right]_z O - \underset{R^1}{\overset{R^1}{Si}} - D_1 - Z - \langle\text{ring}\rangle - (R_9)_v$$

where
v is 0 or 4.
$R_9$ is each independently lower alkyl, lower alkenyl, lower alkynyl, cycloalkyl of 4 to 8 carbon atoms, lower alkoxy, lower alkylthio, phenyl, loweralkylphenylene, phenylloweralkylene, loweralkenylphenylene, phenoxy, phenylthio, loweralkylcarbonyl, loweralkylcarbonyloxy, loweralkoxycarbonyl, bromo, chloro, fluoro, iodo, nitro, cyano, cyanothio, carboxyl, carbonyl, hydroxyl, mercapto or mercaptocarbonyl;
Z is $$-O-, -S-, -\overset{O}{\underset{}{S}}-, -\overset{O}{\underset{O}{S}}-, -\overset{O}{\underset{O}{S}}NH-, -HN\overset{O}{\underset{O}{S}}-, -\overset{O}{C}NH-,$$

$$-HN\overset{O}{C}, -\overset{O}{C}O- \text{ or } -\overset{O}{C}-;$$

$D_1$ is methylene or alkylene of 3 to 8 carbon atoms.

12. The article of manufacture composition according to claim 11 in which
$R^1$ is lower alkyl, lower alkenyl, lower alkynyl, phenyl, lower alkylphenylene, phenyl lower alkylene, or lower alkenylphenylene;
$R^2$ is alkyl of 1 to 12 carbon atoms;
$R^3$ is phenyl, alkyl phenylene of 7 to 18 carbon atoms or alkyl of 1 to 12 carbon atoms;
$R^4$ is alkyl of 1 to 12 carbon atoms, phenyl, alkylphenylene of 7 to 18 carbon atoms, or alkenyl of 2 to 12 carbon atoms;
$R^5$ is alkynyl of 2 to 12 carbon atoms or substituted alkyl of 1 to 12 carbon atoms;
$R^6$ is alkyl of 1 to 12 carbon atoms, phenyl, alkylphenylene of 7 to 18 carbon atoms, or alkenyl of 2 to 12 carbon atoms.

13. The article of manufacture according to claim 12 in which
v is 0 or 1;
$D_1$ is methylene or alkylene of 3 to 8 carbon atoms;
$R^1$ is lower alkyl;
$R^2$ is lower alkyl;
$R^3$ is lower alkyl or phenyl;
$R^4$ is lower alkyl, phenyl, or lower alkenyl;
$R^5$ is lower alkenyl or substituted lower alkyl;
$R^6$ is lower alkyl or lower alkenyl; the substituents on $R^4$, $R^5$ and $R^6$ lower alkyls being independently selected from halogen, amino, cyano, $-CONH_2$, hydroxyl and mercapto;
x has a value from 0 to 100;
y has a value from 0 to 20; and
z has a value from 0 to 20.

14. The article of manufacture according to claim 11 in which
v is 0 or 1;
Z is $-O-$ or $-S-$;
$D_1$ is methylene, propylene or butylene;
$R^1$ is alkyl of 1 to 3 carbon atoms;
$R^2$ is alkyl of 1 to 3 carbon atoms;
$R^3$ is alkyl of 1 to 3 carbon atoms or phenyl;
$R^4$ is alkyl of 1 to 3 carbon atoms, alkenyl of 2 to 4 carbon atoms, phenyl or said alkyl substituted by amino, cyano, hydroxyl or $-CONH_2$;
$R^5$ is alkenyl of 2 to 4 carbon atoms or alkyl of 1 to 3 carbon atoms optionally substituted by amino, cyano, hydroxyl or $-CONH_2$;
$R^6$ is alkyl of 1 to 3 carbon atoms, alkenyl of 2 to 4 carbon atoms or alkyl of 1 to 3 carbon atoms optionally substituted by amino, cyano, hydroxyl or $-CONH_2$;
x has a value from 0 to 100;
y has a value from 0 to 20; and
z has a value from 0 to 20.

15. The article of manufacture according to claim 11 in which
v is 0;
Z is $-O-$;
$D_1$ is methylene or butylene;
$R^1$ is methyl;
$R^2$ is methyl;
$R^3$ is methyl or phenyl;
$R^4$ is methyl, vinyl or phenyl;
$R^5$ is vinyl or methyl, ethyl or propyl optionally substituted by amino, cyano, hydroxyl or $-CONH_2$;
$R^6$ is methyl, vinyl or methyl, ethyl or propyl optionally substituted by amino, cyano, hydrogen or $-CONH_2$;
x has a value from 0 to 100;
y has a value from 0 to 20; and
z has a value from 0 to 10.

16. The article of manufacture according to claim 2 in which
Q is substituted or unsubstituted heterocyclic aromatic of 5 to 18 ring atoms, where the hetero atoms are selected from N, O and S;
D is branched or linear alkylene of 1 or 3 to 12 carbon atoms; and
x, y and z each, independently, has a value from 0 to 100.

17. The article of manufacture according to claim 16 in which the heterocyclic nucleus is pyridinyl, pyridazinyl, pyrimidinyl, pyrazinyl, furanyl, thiofuranyl, pyrrolinyl, indenyl, benzofuranyl, benzothiofuranyl, indolinyl, quinolinyl or isoquinolinyl.

18. The article of manufacture according to claim 1 in which said polyimide, poly(half-amide) or poly(amide-imide) comprises the reaction product of an organic acid, anhydride or acid-anhydride with a bis(amino)-polysiloxane of formula

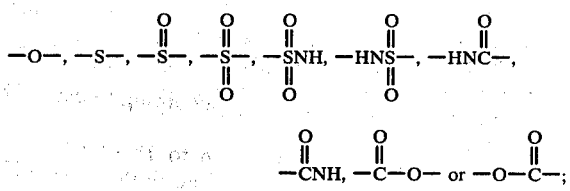

where
Q is a substituted or unsubstituted aromatic group;
Z is

D is unsubstituted or substituted hydrocarbylene;

$R^1$, $R^2$, $R^3$, $R^4$, $R^5$ and $R^6$ each independently is unsubstituted or substituted hydrocarbyl;

x, y and z each independently has a value from 0 to 100.

19. The article of manufacture according to claim 1 in which said polymeric composition comprises a poly(-half-amide) or polyimide comprising the reaction product of a dianhydride component with an amine component, the dianhydride component comprising a dianhydride of formula

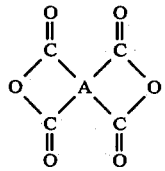

where A is a tetravalent benzene or naphthalene nucleus or a tetravalent group of formula

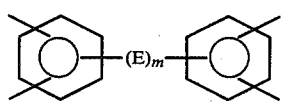

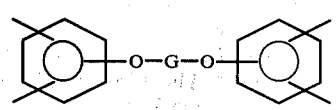

wherein G is phenylene or a group of formula

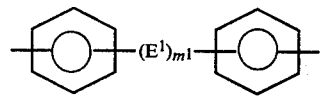

and where m and $m^1$ is each 0 or 1 and E and $E^1$ is each

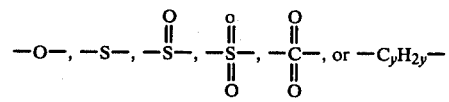

where y is an integer from 1 to 8; the amine component comprising a bis(amino)polysiloxane and, optionally, an organic diamine, the bis(amino)polysiloxane having the formula

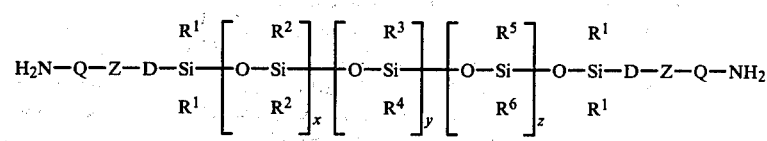

where
Q is a substituted or unsubstituted aromatic group;
Z is

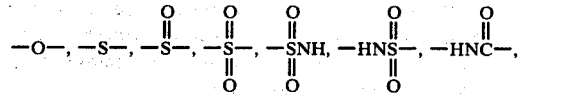

D is substituted or unsubstituted hydrocarbylene of 1 or 3 to 18 carbon atoms;
$R^1$, $R^2$, $R^3$, $R^4$, $R^5$ and $R^6$ each independently is unsubstituted or substituted hydrocarbyl; and
x, y and z, each independently, has a value from 0 to 100;
the organic diamine having the formula $H_2N-Y-NH_2$ where Y is phenylene, diphenylene, naphthylene or a group of formula

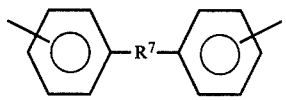

where $R^7$ is branched or linear alkylene of 1 to 20 carbon atoms,

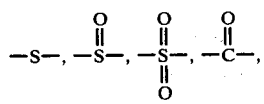

or —O—, or $R^7$ is —O—G'—O—, where G' is phenylene or group of formula

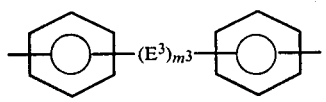

where $m^3$ is 0 or 1 and $E^3$ is

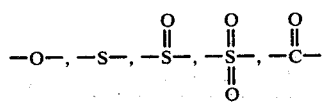

or linear or branched alkylene of 1 to 8 carbon atoms.

20. The article of manufacture according to claim 19 in which
 Q is substituted or unsubstituted carbocyclic aromatic of 6 to 18 ring carbon atoms or substituted or unsubstituted heterocyclic aromatic of 5 to 18 ring carbon atoms where the hetero atoms are selected from N, O and S, and where the substituents are alkyl of 1 to 12 carbon atoms, alkenyl of 2 to 12 carbon atoms, alkynyl of 2 to 12 carbon atoms, cycloalkyl of 4 to 8 carbon atoms, alkoxy of 1 to 12 carbon atoms, alkylthio of 1 to 12 carbon atoms, phenyl, alkylphenylene having 1 to 12 carbon atoms in the alkyl group, phenoxy, phenylthio, alkylcarbonyloxy of 2 to 12 carbon atoms, phenylalkylene of 1 to 12 carbon atoms in the alkylene group, alkylcarbonyl of 2 to 12 carbon atoms, alkoxycarbonyl of 2 to 12 carbon atoms, bromo, chloro, fluoro, iodo, nitro, cyano, cyanothio, carboxy, carbonyl, hydroxy, mercapto, formyl, thioformyl and mercaptocarbonyl;
 D is substituted or unsubstituted hydrocarbylene of 1 or 3 to 18 carbon atoms;
 $R^1$, $R^2$, $R^3$, $R^4$, $R^5$ and $R^6$, each independently, is an unsubstituted or substituted alkyl of 1 to 12 carbon atoms, alkenyl of 2 to 12 carbon atoms, alkynyl of 2 to 12 carbon atoms, cycloalkyl of 4 to 8 carbon atoms, phenyl, alkylphenylene where the alkyl group contains 1 to 12 carbon atoms, phenylalkylene where the alkylene group contains 1 to 12 carbon atoms, or alkenylphenylene with 2 to 12 carbon atoms in the alkenyl group and when substituted, these hydrocarbyl groups are substituted by Br, Cl, I, F, —NC, —NO₂, —OCN, alkoxy of 1 to 8 carbon atoms, —S—(C₁-C₈)alkyl,

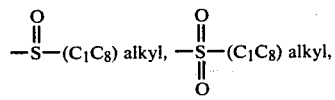

—S—S(C₁-C₈)alkyl, —COOH, —COSH, —C-SOH, —CONH₂, —CN, —CHO, —CHS, —OH, —SH, —NCO and —NR₇R₈ where $R_7$ and $R_8$ independently are hydrogen and lower alkyl.

21. The article of manufacture according to claim 20 in which
 Q is unsubstituted or substituted carbocyclic aromatic of 6 to 18 ring carbon atoms;
 D is branched or linear alkylene of 1 or 3 to 12 carbon atoms;
 x has a value from 0 to 100;
 y has a value from 0 to 20;
 z has a value from 0 to 20.

22. The article of manufacture according to claim 21 in which
 $R^1$ is hydrocarbyl of 1 to 18 carbon atoms;
 $R^2$ is alkyl of 1 to 12 carbon atoms;
 $R^3$ is phenyl, alkyl phenylene of 7 to 18 carbon atoms or alkyl of 1 to 12 carbon atoms;
 $R^4$ is alkyl of 1 to 12 carbon atoms, phenyl, alkylphenylene of 7 to 18 carbon atoms, alkenyl of 2 to 12 carbon atoms;
 $R^5$ is alkenyl of 2 to 12 carbon atoms or substituted alkyl of 1 to 12 carbon atoms;
 $R^6$ is alkyl of 1 to 12 carbon atoms, phenyl, alkylphenylene of 7 to 18 carbon atoms, alkenyl of 2 to 12 carbon atoms.

23. The article of manufacture according to claim 22 in which
 Q is carbocyclic aromatic of 6 to 18 ring carbon atoms that is unsubstituted or substituted by from 1 to 4 alkyl groups of 1 to 12 carbon atoms, alkenyl of 2 to 12 carbon atoms, alkynyl of 2 to 12 carbon atoms, cycloalkyl of 4 to 8 carbon atoms, alkoxy of 1 to 12 carbon atoms, alkylthio of 1 to 12 carbon atoms, phenyl, alkylphenylene having 1 to 12 carbon atoms in the alkyl group, phenoxy, phenylthio, alkyl carbonyl of 2 to 12 carbon atoms, phenylalkylene of 1 to 12 carbon atoms in the alkylene group, alkylcarbonyl of 2 to 12 carbon atoms, alkoxycarbonyl of 2 to 12 carbon atoms, bromo, chloro, fluoro, iodo, nitro, cyano, cyanothio, carboxy, carbonyl, hydroxy, mercapto, formyl, thioformyl and mercaptocarbonyl.

24. The article of manufacture according to claim 23 in which
 Q is carbocyclic aromatic of 6 to 18 ring carbon atoms that is unsubstituted or is substituted by from 1 to 4 of lower alkyl, lower alkenyl, lower alkynyl, cycloalkyl of 4 to 8 carbon atoms, lower alkoxy, lower alkylthio, phenyl, loweralkylphenylene, phenylloweralkylene, loweralkenylphenylene, phenoxy, phenylthio, loweralkylcarbonyl, loweralkylcarbonyloxy, loweralkoxycarbonyl, bromo, chloro, fluoro, iodo, nitro, cyano, cyanothio, carboxyl, carbonyl, hydroxyl, mercapto and mercaptocarbonyl;
 D is methylene or alkylene of 3 to 8 carbon atoms.

25. The article of manufacture according to claim 24 in which
 Q contains up to one substituent,
 $R^1$ is lower alkyl;
 $R^2$ is lower alkyl;
 $R^3$ is lower alkyl or phenyl;
 $R^4$ is lower alkyl, phenyl, or lower alkenyl;
 $R^5$ is lower alkenyl or substituted lower alkyl;
 $R^6$ is lower alkyl or lower alkenyl, the substituents on $R^4$, $R^5$ and $R^6$ lower alkyl being independently selected from halogen, amino, cyano, —CONH₂, hydroxyl and mercapto.

26. The article of manufacture according to claim 25 in which Z is

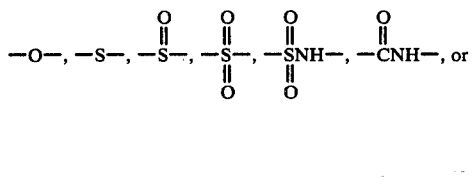, 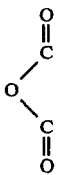

$$-\overset{\text{O}}{\underset{\text{||}}{\text{C}}}-\text{O}-.$$

27. The article of manufacture according to claim 26 in which

Z is —O— or —S—;
D is methylene, propylene or butylene;
$R^1$ is alkyl of 1 to 3 carbon atoms;
$R^2$ is alkyl of 1 to 3 carbon atoms;
$R^3$ is alkyl of 1 to 3 carbon atoms or phenyl;
$R^4$ is alkyl of 1 to 3 carbon atoms, alkenyl of 2 to 4 carbon atoms, phenyl or said alkyl substituted by amino, chloro, hydroxyl or —CONH$_2$;
$R^5$ is alkenyl of 2 to 4 carbon atoms or alkyl of 1 to 3 carbon atoms optionally substituted by amino, cyano, hydroxyl or —CONH$_2$;
$R^6$ is alkyl of 1 to 3 carbon atoms, alkenyl of 2 to 4 carbon atoms or alkyl of 1 to 3 carbon atoms optionally substituted by amino, cyano, hydroxyl or —CONH$_2$;
x has a value from 0 to 100;
y has a value from 0 to 20; and
z has a value from 0 to 20.

28. The article of manufacture according to claim 27 in which

Q is unsubstituted
Z is —O—;
D is methylene or butylene;
$R^1$ is methyl;
$R^2$ is methyl;
$R^3$ is methyl or phenyl;
$R^4$ is methyl, vinyl or phenyl;
$R^5$ is vinyl or methyl, ethyl or propyl optionally substituted by amino, cyano, hydroxyl or —CONH$_2$;
$R^6$ is methyl, vinyl or methyl, ethyl or propyl optionally substituted by amino, cyano, hydrogen or —CONH$_2$;
x has a value from 0 to 100;
y has a value from 0 to 20; and
z has a value from 0 to 10.

29. The article of manufacture according to claim 1 in which said polymer comprises the reaction product of an organic diamine with a dianhydride or acid-anhydride of formula

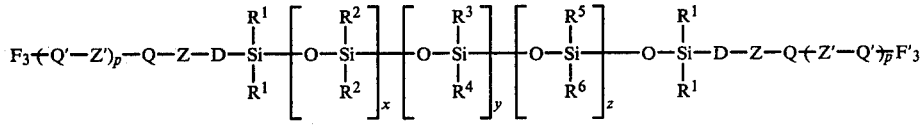

where
$F_3$ and $F'_3$ each, independently, is COOH or

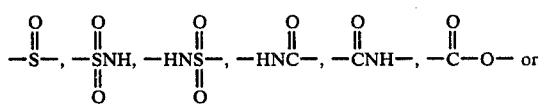

where the carbonyl groups are located ortho to each other on Q' or Q;
Q' and Q are carbocyclic aromatic of 6 to 18 ring carbon atoms;
Z' and Z are independently selected from —O—, —S—,

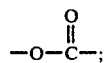

p is 0 or 1;
D is substituted or unsubstituted hydrocarbylene of 1 or 3 to 18 carbon atoms;
$R^1$, $R^2$, $R^3$, $R^4$, $R^5$ and $R^6$, each independently, is unsubstituted or substituted alkyl of 1 to 12 carbon atoms, alkynyl of 2 to 12 carbon atoms, cycloalkyl of 4 to 8 carbon atoms, phenyl, alkylphenylene where the alkyl group contains 1 to 12 carbon atoms, phenylalkylene where the alkylene group contains 1 to 12 carbon atoms, alkenylphenylene with 2 to 12 carbon atoms, alkenylphenylene with 2 to 12 carbon atoms in the alkenyl group and when substituted, these hydrocarbyl groups are substituted by Br, Cl, I, F, —NC, —NO$_2$, —OCN, alkoxy of 1 to 8 carbon atoms, —S—(C$_1$-C$_8$)alkyl,

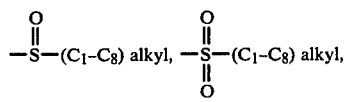

—S—S—(C$_1$-C$_8$)alkyl, —COOH, —COSH, —CSOH, —CONH$_2$, —CN, —CHO, —CHS, —OH, —SH, —NCO and —NR$_7$R$_8$ where R$_7$ and R$_8$ independently are hydrogen or lower alkyl;
x, y and z each independently has a value from 0 to 100.

30. The article of manufacture according to claim 1 in which said polymer composition contains particles of an electrically conductive material.

31. The article of manufacture according to claim 1 in which said substrate comprises conductive wire.

32. The article of manufacture according to claim 1 in which said substrate comprises fibers or filaments of carbon, glass, metal, ceramic, polyimide and fabrics woven therefrom.

* * * * *